United States Patent [19]

Damon, II

[11] Patent Number: 4,876,280
[45] Date of Patent: Oct. 24, 1989

[54] ARYLCYCLOHEXANE AND ARYLCYCLOHEXENE ANALOGS OF MEVALONOLACTONE DERIVATIVES AND THEIR USE

[75] Inventor: Robert E. Damon, II, Wharton, N.J.

[73] Assignee: Sandoz Pharm. Corp., E. Hanover, N.J.

[21] Appl. No.: 166,356

[22] Filed: Mar. 10, 1988

[51] Int. Cl.[4] .................... A61K 31/19; A61K 31/215
[52] U.S. Cl. .................................... 514/510; 549/292; 514/460; 514/532; 562/469
[58] Field of Search .......................... 549/292; 562/469

[56] References Cited

U.S. PATENT DOCUMENTS

| 3,983,140 | 9/1976 | Endo et al. | 260/343.5 |
|---|---|---|---|
| 4,248,889 | 2/1981 | Oka et al. | 424/308 |
| 4,375,475 | 3/1983 | Willard et al. | 424/279 |
| 4,474,971 | 10/1984 | Wareing | 549/214 |
| 4,499,289 | 2/1985 | Baran et al. | 549/292 |
| 4,650,890 | 3/1987 | Jewell et al. | 556/446 |
| 4,772,626 | 9/1988 | Smith et al. | 549/292 |

FOREIGN PATENT DOCUMENTS

| 86/03488 | 6/1986 | PCT Int'l Appl. | |
| 1325056 | 8/1973 | United Kingdom | 562/469 |

OTHER PUBLICATIONS

Hulcher, Arch. Biochem. Biophys. 146, 422-427 (1971).
Singer et al., Proc. Soc. Exp. Biol. Med. 102, 370-373 (1959).
Stokker et al., J. Med. Chem. 28, 347-358 (1985).

Primary Examiner—Robert T. Bond
Assistant Examiner—B. A. Trinh
Attorney, Agent, or Firm—Gerald D. Sharkin; Richard E. Vila; Melvyn M. Kassenoff

[57] ABSTRACT

Compounds of the formula

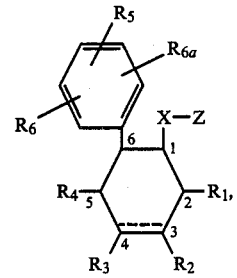

wherein $R_1$ is hydrogen, $C_{1-3}$alkyl, n-butyl, i-butyl or t-butyl,
$R_2$ is hydrogen or $C_{1-3}$alkyl,
$R_3$ is hydrogen or $C_{1-3}$alkyl,
$R_4$ is hydrogen, $C_{1-3}$alkyl, n-butyl, i-butyl or t-butyl,
$R_5$ is hydrogen, $C_{1-3}$alkyl, n-butyl, i-butyl, t-butyl, $C_{1-3}$alkoxy, n-butoxy, i-butoxy, fluoro, chloro, trifluoromethyl, phenoxy or benzyloxy,
$R_6$ is hydrogen, $C_{1-3}$alkyl, $C_{1-3}$alkoxy, fluoro, chloro, trifluoromethyl, phenoxy or benzyloxy, with the provisos that not more than one of $R_5$ and $R_6$ is trifluoromethyl, not more than one of $R_5$ and $R_6$ is phenoxy, and not more than one of $R_5$ and $R_6$ is benzyloxy, or
$R_5$ and $R_6$ are attached to adjacent carbon atoms and taken together form a radical of the formula —CH=CH—CH=CH—,
$R_{6a}$ is hydrogen, $C_{1-2}$alkyl, fluoro or chloro,
X is —CH$_2$CH$_2$— or

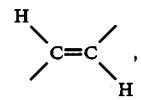

Z is 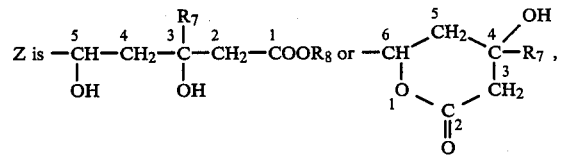

wherein $R_7$ is hydrogen or $C_{1-3}$alkyl, and
$R_8$ is hydrogen, $R_9$ or M, wherein $R_9$ is a physiologically acceptable ester group, and M is a pharmaceutically acceptable cation, and the broken line represents a double ($\pi$) bond or two hydrogen atoms (one on each carbon atom), the use thereof for inhibiting cholesterol biosynthesis and lowering the blood cholesterol level and, therefore, in the treatment of hyperlipoproteinemia and atherosclerosis, pharmaceutical compositions comprising such compounds and processes for and intermediates in the synthesis of such compounds.

13 Claims, No Drawings

ARYLCYCLOHEXANE AND ARYLCYCLOHEXENE ANALOGS OF MEVALONOLACTONE DERIVATIVES AND THEIR USE

This invention relates to compounds of the formula

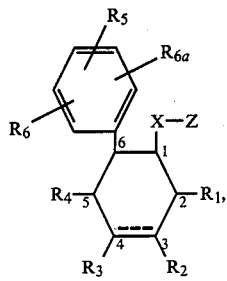

(I)

wherein $R_1$ is hydrogen, $C_{1-3}$alkyl, n-butyl, i-butyl or t-butyl,
$R_2$ is hydrogen or $C_{1-3}$alkyl,
$R_3$ is hydrogen or $C_{1-3}$alkyl,
$R_4$ is hydrogen, $C_{1-3}$alkyl, n-butyl, i-butyl or t-butyl,
$R_5$ is hydrogen, $C_{1-3}$alkyl, n-butyl, i-butyl, t-butyl, $C_{1-3}$alkoxy, n-butoxy, i-butoxy, fluoro, chloro, trifluoromethyl, phenoxy or benzyloxy,
$R_6$ is hydrogen, $C_{1-3}$alkyl, $C_{1-3}$alkoxy, fluoro, chloro, trifluoromethyl, phenoxy or benzyloxy, with the provisos that not more than one of $R_5$ and $R_6$ is trifluoromethyl, not more than one of $R_5$ and $R_6$ is phenoxy, and not more than one of $R_5$ and $R_6$ is benzyloxy, or
$R_5$ and $R_6$ are attached to adjacent carbon atoms and taken together form a radical of the formula —CH=CH—CH=CH—,
$R_{6a}$ is hydrogen, $C_{1-2}$alkyl, fluoro or chloro,
X is —$CH_2CH_2$— or

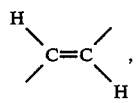

Z is

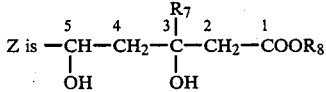

(a)

or

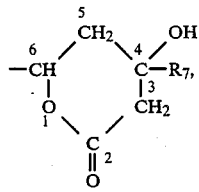

(b)

wherein $R_7$ is hydrogen or $C_{1-3}$alkyl, and
$R_8$ is hydrogen, $R_9$ or M,
wherein $R_9$ is a physiologically acceptable ester group, and
M is a pharmaceutically acceptable cation, and
the broken line represents a double ($\pi$) bond or two hydrogen atoms (one on each carbon atom), processes for and intermediates in the synthesis thereof, pharmaceutical compositions comprising a compound of Formula I and the use of the compounds of Formula I for inhibiting cholesterol biosynthesis and lowering the blood cholesterol level and, therefore, in the treatment of hyperlipoproteinemia and atherosclerosis.

By the term "physiologically acceptable ester group" is meant a group which, together with the —COO— radical to which it is attached, forms an ester group which is physiologically acceptable. The preferred such groups are physiologically acceptable and hydrolyzable ester groups. By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein $R_8$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R_9'$.

Preferably, when both $R_2$ and $R_3$ are $C_{1-3}$alkyl, and the broken line represents two hydrogen atoms, $R_2$ and $R_3$ are cis to each other.

The compounds of Formula I may be divided into two groups, viz., the compounds of Formula IA and those of Formula IB,

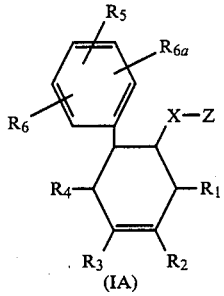 and 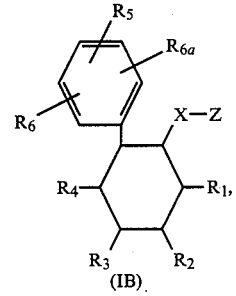

(IA)    (IB)

each of which may be divided into two subgroups based upon the significance of Z, viz., Group IAa (the compounds of Group IA wherein Z is a group of Formula a), Group IAb (the compounds of Group IA wherein Z is a group of Formula b), Group IBa (the compounds of Group IB wherein Z is a group of Formula a) and Group IBb (the compounds of Group IB wherein Z is a group of Formula b). In the compounds of Groups IBa and IBb, when both $R_2$ and $R_3$ are $C_{1-3}$alkyl, they are preferably cis to each other.

$R_1$ is preferably $R_1'$, where $R_1'$ is hydrogen or $C_{1-3}$alkyl, and more preferably $R_1''$, where $R_1''$ is $C_{1-3}$alkyl.
$R_2$ is preferably $R_2'$, where $R_2'$ is hydrogen or methyl, and more preferably hydrogen.
$R_3$ is preferably $R_3'$, where $R_3'$ is hydrogen or methyl, and more preferably hydrogen.
$R_4$ is preferably $R_4'$, where $R_4'$ is hydrogen or $C_{1-3}$alkyl, and more preferably $R_4''$, where $R_4''$ is $C_{1-3}$alkyl.
When $R_5$ and $R_6$ together do not form a radical of the formula —CH=CH—CH=CH—:

(1) $R_5$ is preferably $R_5'$, where $R_5'$ is hydrogen, $C_{1-3}$alkyl, trifluoromethyl, fluoro or chloro, more preferably $R_5''$, where $R_5''$ is hydrogen, methyl, fluoro or chloro, and most preferably $R_5'''$, where $R_5'''$ is hydrogen or fluoro, especially hydrogen or 4-fluoro and most especially 4-fluoro.

(2) $R_6$ is preferably $R_6'$, where $R_6'$ is hydrogen, $C_{1-2}$alkyl, fluoro or chloro, more preferably $R_6''$, where $R_6''$ is hydrogen, methyl, fluoro or chloro, and most preferably hydrogen.

(3) $R_{6a}$ is preferably $R_{6a}'$, where $R_{6a}'$ is hydrogen or methyl, and more preferably hydrogen.

(4) Preferably, when two of $R_5$ ($R_5'$, etc.), $R_6$ ($R_6'$, etc.) and $R_{6a}$ are other than hydrogen and one is hydrogen, at least one of the two that are other than hydrogen is in a meta or para position and not more than one of them is a member of the group consisting of t-butyl, trifluoromethyl, phenoxy and benzyloxy; more preferably, the two that are other than hydrogen are not ortho to each other when neither of them is a member of the group consisting of methyl, methoxy, fluoro and chloro.

(5) Preferably, when each of $R_5$ ($R_5'$, etc.), $R_6$ ($R_6'$, etc.) and $R_{6a}$ ($R_{6a}'$) is other than hydrogen, at least two of them are in meta or para positions and not more than one of them is a member of the group consisting of t-butyl, trifluoromethyl, phenoxy and benzyloxy; more preferably, no two of them are ortho to each other unless at least one member of each pair of substituents that are ortho to each other is a member of the group consisting of methyl, methoxy, fluoro and chloro.

When $R_5$ and $R_6$ together form a radical of the formula —CH=CH—CH=CH—:

$R_{6a}$ is preferably $R_{6a}''$, where $R_{6a}''$ is hydrogen, methyl or fluoro, and more preferably hydrogen.

$R_7$ is preferably $R_7'$, where $R_7'$ is hydrogen or methyl, and most preferably hydrogen.

$R_8$ is preferably $R_8'$, where $R_8'$ is hydrogen, $R_9'$ or M, more preferably $R_8''$, where $R_8''$ is hydrogen, $C_{1-2}$alkyl or M, and most preferably M. M is preferably M' and most preferably sodium.

$R_9$ is preferably $R_9'$, where $R_9'$ is $C_{1-3}$alkyl, n-butyl, i-butyl, t-butyl or benzyl, more preferably $C_{1-3}$alkyl and most preferably $C_{1-2}$alkyl.

X is preferably

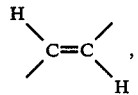

i.e., (E)—CH=CH—.

Z is preferably a group of Formula a wherein $R_7$ is $R_7'$ and $R_8$ is $R_8'$ or a group of Formula b wherein $R_7$ is $R_7'$, more preferably a group of Formula a wherein $R_7$ is hydrogen and $R_8$ is $R_8''$ or a group of Formula b wherein $R_7$ is hydrogen and most preferably a group of Formula a wherein $R_7$ is hydrogen and $R_8$ is M, especially a group of Formula a wherein $R_7$ is hydrogen and $R_8$ is M'.

M is preferably free from centers of asymmetry and is more preferably M', where M' is sodium, potassium or ammonium, and most preferably sodium. For simplicity, each of the formulae in which M appears has been written as if M were monovalent and, preferably, it is. However, it may also be divalent or trivalent and, when it is, it balances the charge of two or three carboxy groups, respectively.

Preferably, the $R_5$-bearing phenyl (or naphthyl) group and the —X—Z group are trans to each other.

Preferably, when $R_1$ and $R_4$ are alkyl, they are cis to each other and more preferably they are also cis to the $R_5$-bearing phenyl (or naphthyl) group and trans to the —X—Z group. When only one of $R_1$ and $R_4$ is alkyl, the one that is alkyl is preferably cis to the $R_5$-bearing phenyl (or naphthyl) group and trans to the —X—Z group.

As set forth above, when both $R_2$ and $R_3$ are $C_{1-3}$alkyl and the broken line represents two hydrogen atoms, $R_2$ and $R_3$ are preferably cis to each other.

Insofar as the compounds of Groups IAa and IBa and each of the subgroups thereof are concerned, the erythro isomers are generally preferred over the threo isomers, erythro and threo referring to the relative positions of the hydroxy groups in the 3- and 5-positions (of the group of Formula a).

Insofar as the compounds of Groups IAb and IBb and each of the subgroups thereof are concerned, the trans lactones are generally preferred over the cis lactones, cis and trans referring to the relative orientations of $R_7$ and the hydrogen atom in the 6-position of the group of Formula b.

As between otherwise identical compounds of Formula I, those wherein Z is a group of Formula a, especially a group of Formula a wherein $R_8$ is M, are generally preferred over those wherein Z is a group of Formula b.

As is self-evident, each compound of Formula I (and every subscope and species thereof) has at least four centers of asymmetry, the two carbon atoms bearing the hydroxy groups in the group of Formula a and the carbon atom bearing the hydroxy group and the carbon atom having the free valence in the group of Formula b and the carbon atoms of the cyclohexane or cyclohexene ring to which the —X—Z and $R_5$-bearing phenyl (or naphthyl) groups are attached. In addition, when $R_1$ is alkyl, the ring carbon atom to which it is attached is a center of asymmetry, when $R_2$ is $C_{1-3}$alkyl and the broken line represents two hydrogen atoms, the ring carbon atom to which it is attached is a center of asymmetry, when $R_3$ is $C_{1-3}$alkyl and the broken line represents two hydrogen atoms, the ring carbon atom to which it is attached is a center of asymmetry, and when $R_4$ is alkyl, the ring carbon atom to which it is attached is a center of asymmetry. Consequently, when $R_8$ does not contain a center of asymmetry, there are at least sixteen (and as many as two hundred and fifty-six) geometric and stereoisomeric forms (enantiomers) of each compound. When $R_8$ contains one or more centers of asymmetry, the number of enantiomers is at least doubled. Since it is preferred that $R_8$ not contain a center of asymmetry and for reasons of simplicity any additional stereoisomers resulting from the presence of one or more centers of asymmetry in $R_8$ will be ignored, it being assumed that $R_8$ is free of centers of asymmetry.

All such geometric and stereoisomers are within the scope of this invention.

Insofar as the —X—Z moiety is concerned, when Z is a group of Formula a, the 3R,5R and 3R,5S isomers are preferred, with the former being particularly preferred when X is —CH$_2$CH$_2$— and the latter being particularly preferred when X is

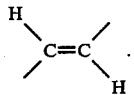

When Z is a group of Formula b, the 4R,6R and 4R,6S isomers are preferred, with the former being particularly preferred when X is —CH$_2$CH$_2$— and the latter being particularly preferred when X is

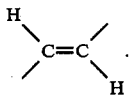

Insofar as the 1-, 2- and 6-positions of the cyclohexene ring are concerned, the preferred isomers are those whose absolute configuration about each of these centers of asymmetry is the same as the compounds of Examples 1-9, the R$_5$-bearing phenyl (or naphthyl) group and the —X—Z group being trans to each other.

Each of the preferences set forth above, independently of each of the others, applies, not only to the compounds of Formula I, but also to the compounds of Groups IA and IB and those of Groups IAa, IAb, IBa and IBb as well as to every other subgroup thereof set forth infra. When any preference contains a variable, the preferred significances of that variable apply to the preference in question, unless otherwise indicated. Likewise, they apply to each occurrence of a variable in the intermediates set forth in Reaction Schemes I-VIII, unless otherwise indicated.

Preferred groups of compounds of Formula I include the compounds (i) of Group IAa wherein R$_1$ is R$_1'$, R$_2$ is R$_2'$, R$_3$ is R$_3'$, R$_4$ is R$_4'$, R$_7$ is R$_7'$, R$_8$ is R$_8'$, and either R$_5$ is R$_5'$, R$_6$ is R$_6'$, and R$_{6a}$ is R$_{6a}'$ or R$_5$ and R$_6$ are attached to adjacent carbon atoms and taken together form a radical of the formula —CH=CH—CH=CH—, and R$_{6a}$ is R$_{6a}''$, (ii) of (i) wherein R$_2$ is hydrogen, R$_3$ is hydrogen, R$_7$ is hydrogen, R$_8$ is R$_8''$, especially M, X is

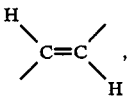

and either R$_5$ is R$_5''$, R$_6$ is R$_6''$, and R$_{6a}$ is hydrogen or R$_5$ and R$_6$ are attached to adjacent carbon atoms and taken together form a radical of the formula —CH=CH—CH=CH—, and R$_{6a}$ is hydrogen, (iii) of (ii) wherein R$_1$ is R$_1''$, R$_4$ is R$_4''$, and either R$_5$ is R$_5'''$, R$_6$ is hydrogen, and R$_{6a}$ is hydrogen or R$_5$ and R$_6$ are attached to adjacent carbon atoms and taken together form a radical of the formula —CH=CH—CH=CH—, and R$_{6a}$ is hydrogen, (iv)-(vi) of (i)-(iii) wherein any M is M', (vii) of Group IAb wherein R$_1$ is R$_1'$, R$_2$ is R$_2'$, R$_3$ is R$_3'$, R$_4$ is R$_4'$, R$_7$ is R$_7'$, and either R$_5$ is R$_5'$, R$_6$ is R$_6'$, and R$_{6a}$ is R$_{6a}'$ or R$_5$ and R$_6$ are attached to adjacent carbon atoms and taken together form a radical of the formula —CH=CH—CH=CH—, and R$_{6a}$ is R$_{6a}''$, (viii) of (vii) wherein R$_2$ is hydrogen, R$_3$ is hydrogen, R$_7$ is hydrogen, X is

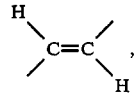

and either R$_5$ is R$_5''$, R$_6$ is R$_6''$, and R$_{6a}$ is hydrogen or R$_5$ and R$_6$ are attached to adjacent carbon atoms and taken together form a radical of the formula —CH=CH—CH=CH—, and R$_{6a}$ is hydrogen, (ix) of (viii) wherein R$_1$ is R$_1''$, R$_4$ is R$_4''$, and either R$_5$ is R$_5'''$, R$_6$ is hydrogen, and R$_{6a}$ is hydrogen or R$_5$ and R$_6$ are attached to adjacent carbon atoms and taken together form a radical of the formula —CH=CH—CH=CH—, and R$_{6a}$ is hydrogen, (x) of Group IBa wherein R$_1$ is R$_1'$, R$_2$ is R$_2'$, R$_3$ is R$_3'$, R$_4$ is R$_4'$, R$_7$ is R$_7'$, R$_8$ is R$_8'$, and either R$_5$ is R$_5'$, R$_6$ is R$_6'$, and R$_{6a}$ is R$_{6a}'$ or R$_5$ and R$_6$ are attached to adjacent carbon atoms and taken together form a radical of the formula —CH=CH—CH=CH—, and R$_{6a}$ is R$_{6a}''$, (xi) of (x) wherein R$_2$ is hydrogen, R$_3$ is hydrogen, R$_7$ is hydrogen, R$_8$ is R$_8''$, especially M, X is

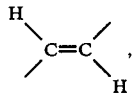

and either R$_5$ is R$_5''$, R$_6$ is R$_6''$, and R$_{6a}$ is hydrogen or R$_5$ and R$_6$ are attached to adjacent carbon atoms and taken together form a radical of the formula —CH=CH—CH=CH—, and R$_{6a}$ is hydrogen, (xii) of (xi) wherein R$_1$ is R$_1''$, R$_4$ is R$_4''$, and either R$_5$ is R$_5'''$, R$_6$ is hydrogen, and R$_{6a}$ is hydrogen or R$_5$ and R$_6$ are attached to adjacent carbon atoms and taken together form a radical of the formula —CH=CH—CH=CH—, and R$_{6a}$ is hydrogen, (xiii)-(xv) of (x)-(xii) wherein any M is M', (xvi) of Group IBb wherein R$_1$ is R$_1'$, R$_2$ is R$_2'$, R$_3$ is R$_3'$, R$_4$ is R$_4'$, R$_7$ is R$_7'$, and either R$_5$ is R$_5'$, R$_6$ is R$_6'$, and R$_{6a}$ is R$_{6a}'$ or R$_5$ and R$_6$ are attached to adjacent carbon atoms and taken together form a radical of the formula —CH=CH—CH=CH—, and R$_{6a}$ is R$_{6a}''$, (xvii) of (xvi) wherein R$_2$ is hydrogen, R$_3$ is hydrogen, R$_7$ is hydrogen, X is

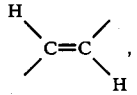

and either $R_5$ is $R_5''$, $R_6$ is $R_6''$, and $R_{6a}$ is hydrogen or $R_5$ and $R_6$ are attached to adjacent carbon atoms and taken together form a radical of the formula —CH=CH—CH=CH—, and $R_{6a}$ is hydrogen, and (xviii) of (xvii) wherein $R_1$ is $R_1''$, $R_4$ is $R_4''$, and either $R_5$ is $R_5'''$, $R_6$ is hydrogen, and $R_{6a}$ is hydrogen or $R_5$ and $R_6$ are attached to adjacent carbon atoms and taken together form a radical of the formula —CH=CH—CH=CH—, and $R_{6a}$ is hydrogen.

The preferred compounds of each of Groups (i)-(xviii) are those wherein (a) the $R_5$-bearing phenyl (or naphthyl) group and the —X—Z group are trans to each other, (b) when $R_1$ is alkyl, it is cis to the $R_5$-bearing phenyl (or naphthyl) group and trans to the —X—Z group and having (c) in the —X—Z group, the 3R,5R or 3R,5S configuration, especially the former when X is —CH$_2$CH$_2$— and especially the latter when X is

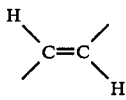

(Groups (i)-(vi) and (x)-(xv) only) and the 4R,6R or 4R,6S configuration, especially the former when X is —CH$_2$CH$_2$— and especially the latter when X is

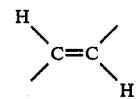

(Groups (vii)-(ix) and (xvi)-(xviii) only) and (d) in the 1-, 2- and 6-positions of the cyclohexane or cyclohexene ring, the same absolute configuration as that of Examples 1-9.

The compounds of Formula I may be synthesized as follows:

Reaction Scheme I

The compounds of Formula I wherein $R_7$ is hydrogen may be synthesized by the following series of reactions:

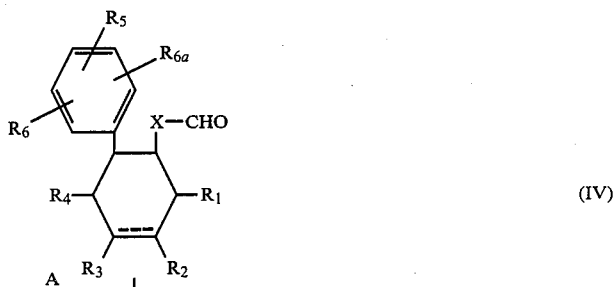

(IV)

(1) Strong base + CH$_3$—CO—CH$_2$—COOR$_9'$ (V)
(2) Aldehyde of Formula IV

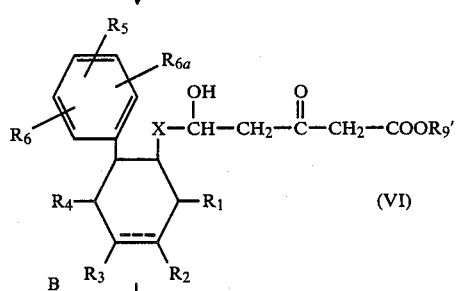

(VI)

Mild reducing agent

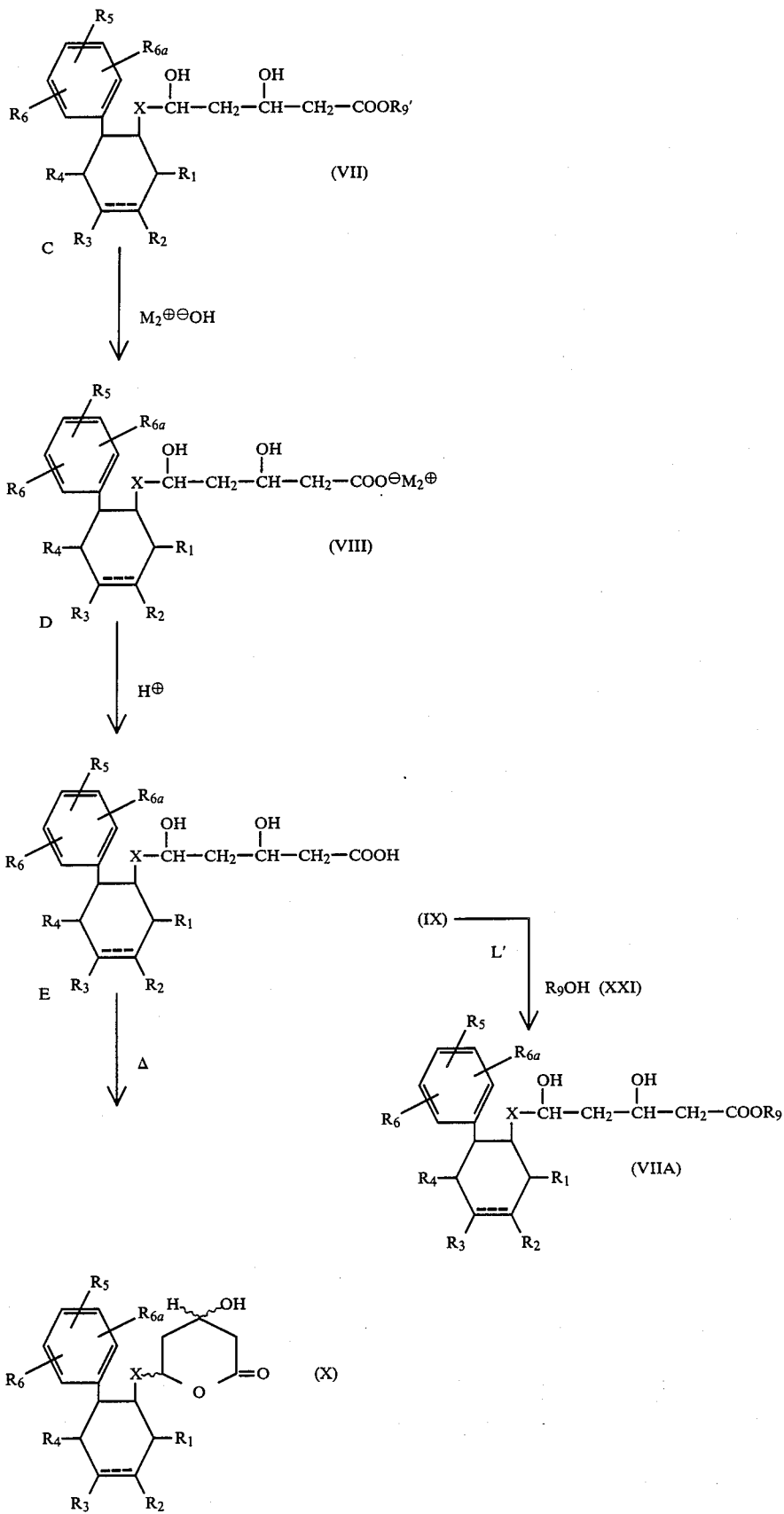

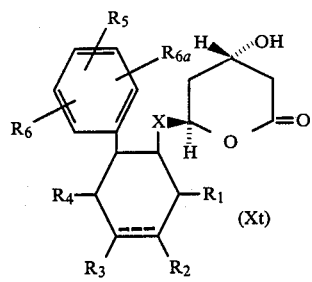
(Xt)
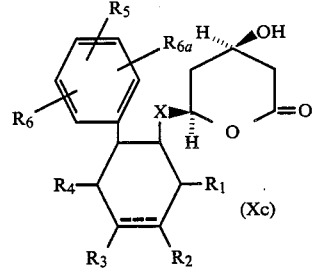
(Xc)
Reaction Scheme II
The compounds of Formula I wherein $R_7$ is $C_{1-3}$alkyl may be synthesized by the following series of reactions:
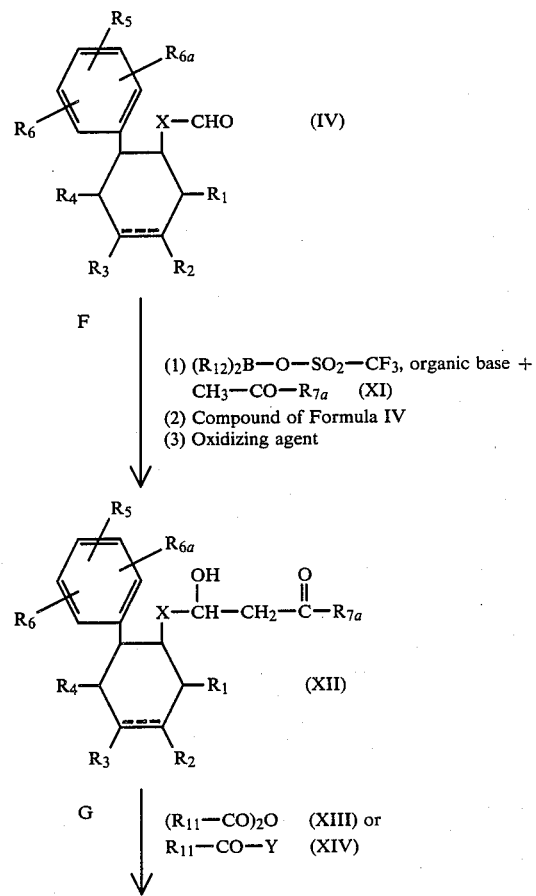

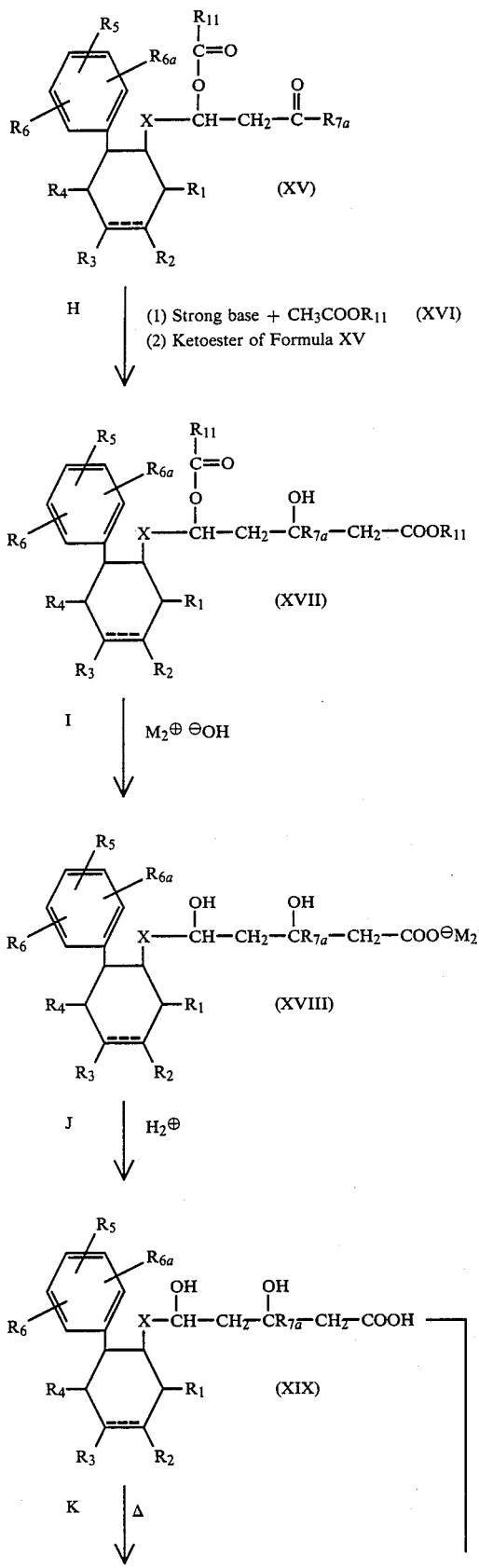

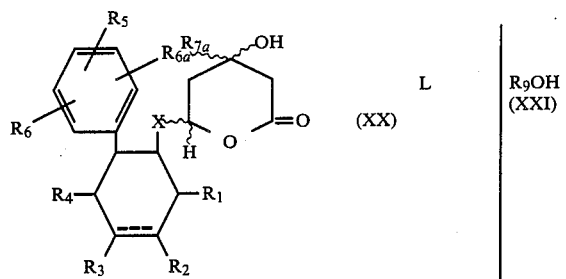
(XX)
R₉OH
(XXI)
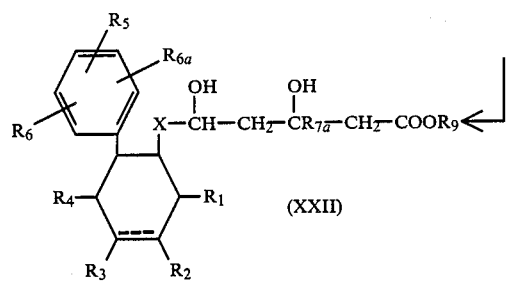
(XXII)
Reaction Scheme III
The compounds of Formula IV wherein X is
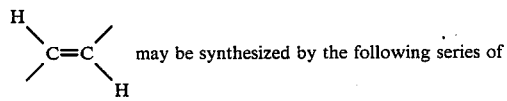
may be synthesized by the following series of reactions.
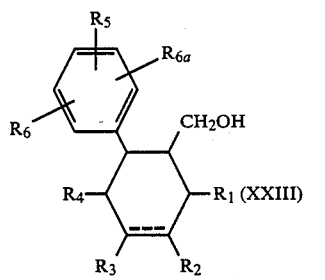
(XXIII)
M | Mild oxidizing agent -continued
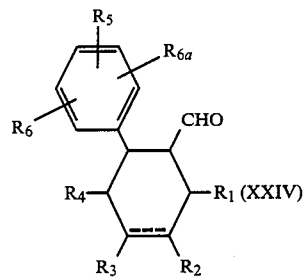
N | (1) LiC≡C—O—C$_2$H$_5$
(2) H$^⊕$
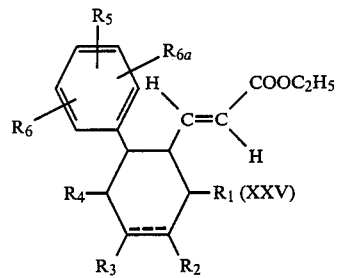
O | (1) $^⊖$OH
(2) H$^⊕$
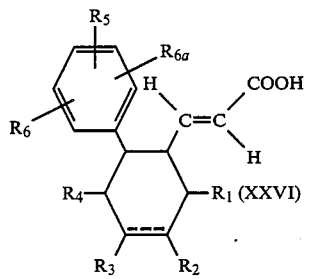
P | SOY$_2$ (XXVII)
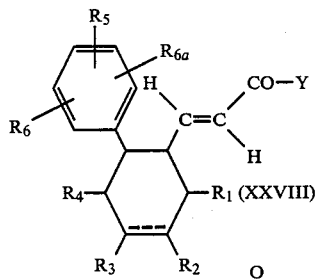
Q | Li$^⊕$ $^⊖$N ... CH$_3$ C$_6$H$_5$ (XXIX)

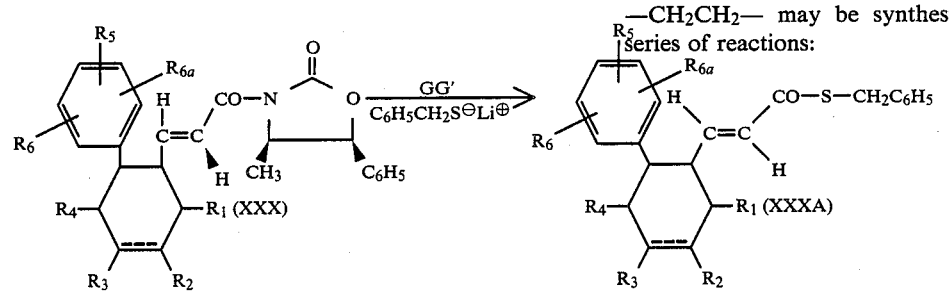
-continued    Reaction Scheme IV
The compounds of Formula IV wherein X is —CH₂CH₂— may be synthesized by the following series of reactions:
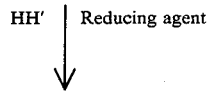
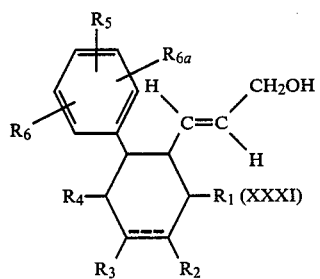
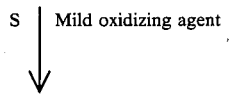
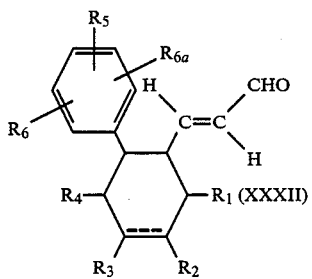

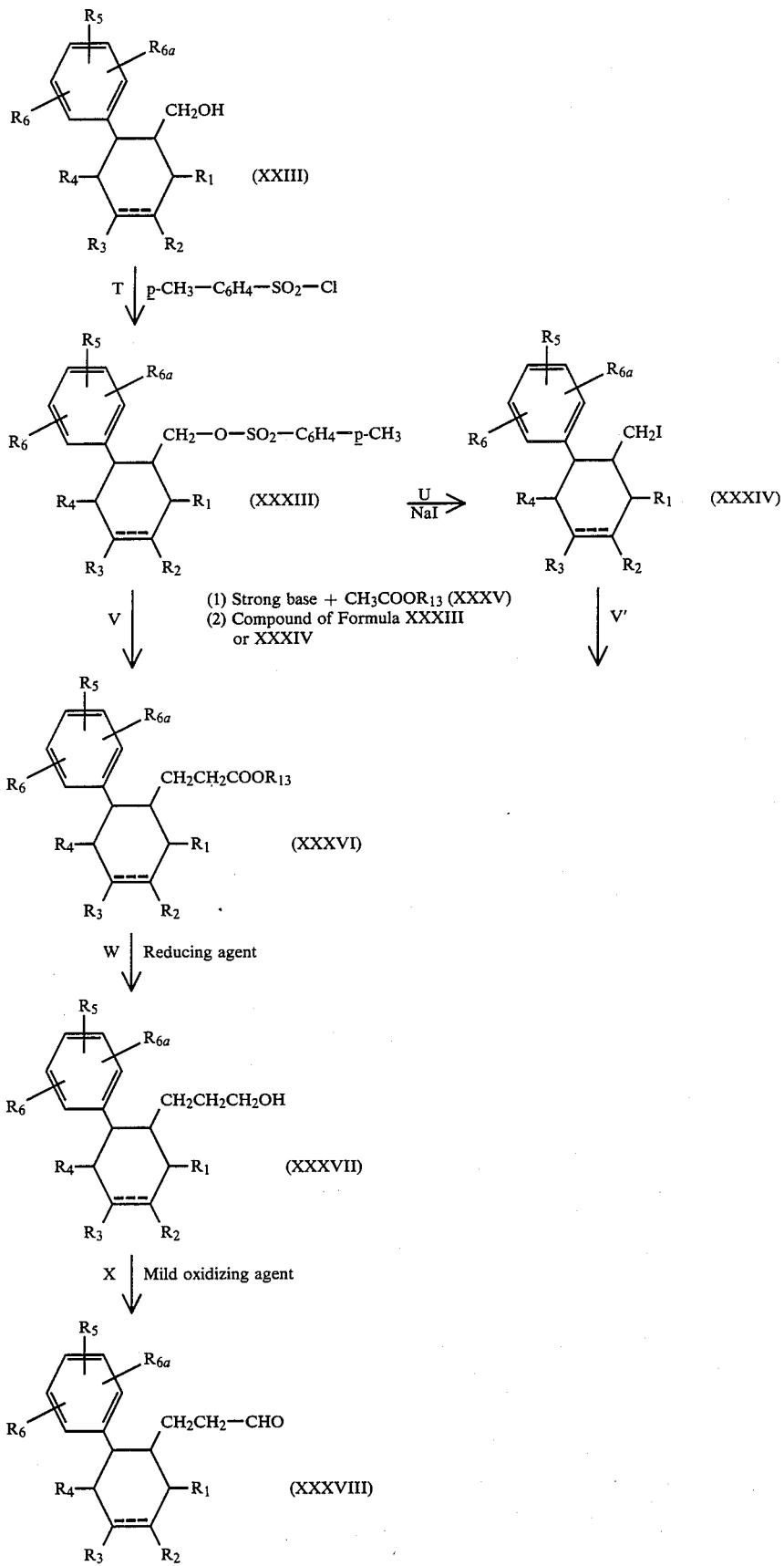

Reaction Scheme V
The compounds of Formula IV wherein X is
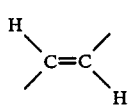
may be synthesized by the following series of reactions:
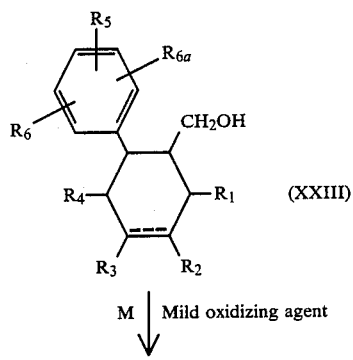
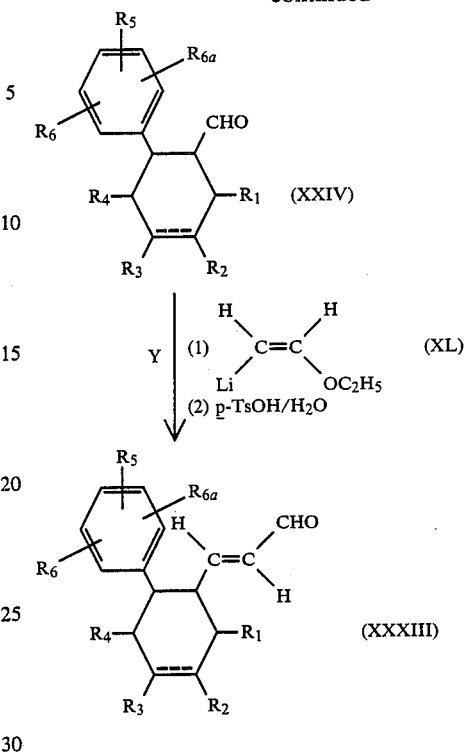
Reaction Scheme VI
The compounds of Formula XXXIII may be synthesized by the following series of reactions:
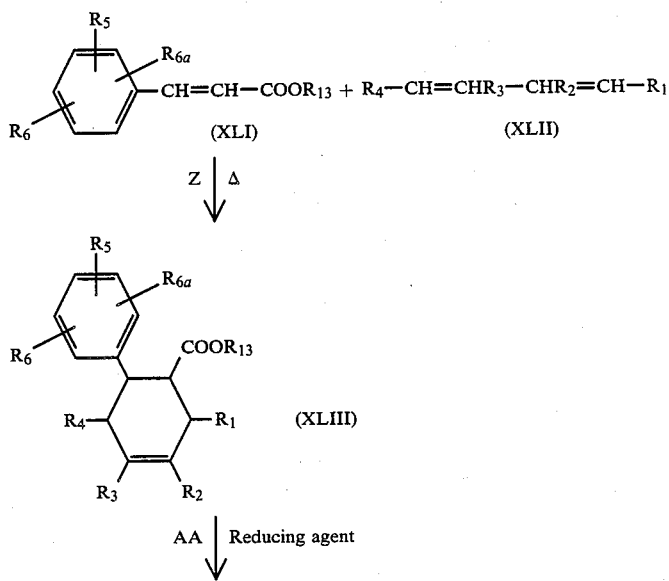

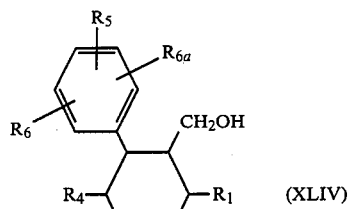
(XLIV)
BB ↓ H₂
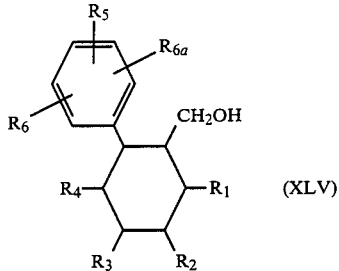
(XLV)
Reaction Scheme VII
The compounds of Formula XLIV are preferably synthesized by the following series of reactions:
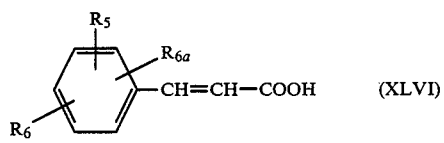
(XLVI)
CC ↓ SOY₂   (XXVII)
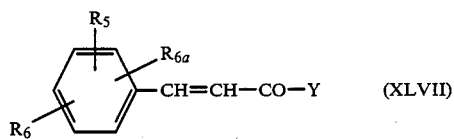
(XLVII)
DD ↓ 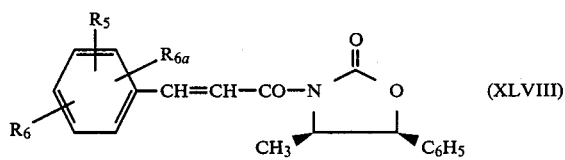 (XXIX)
EE ↓ R₄—CH=CR₃—CR₂=CH—R₁   (XLII)

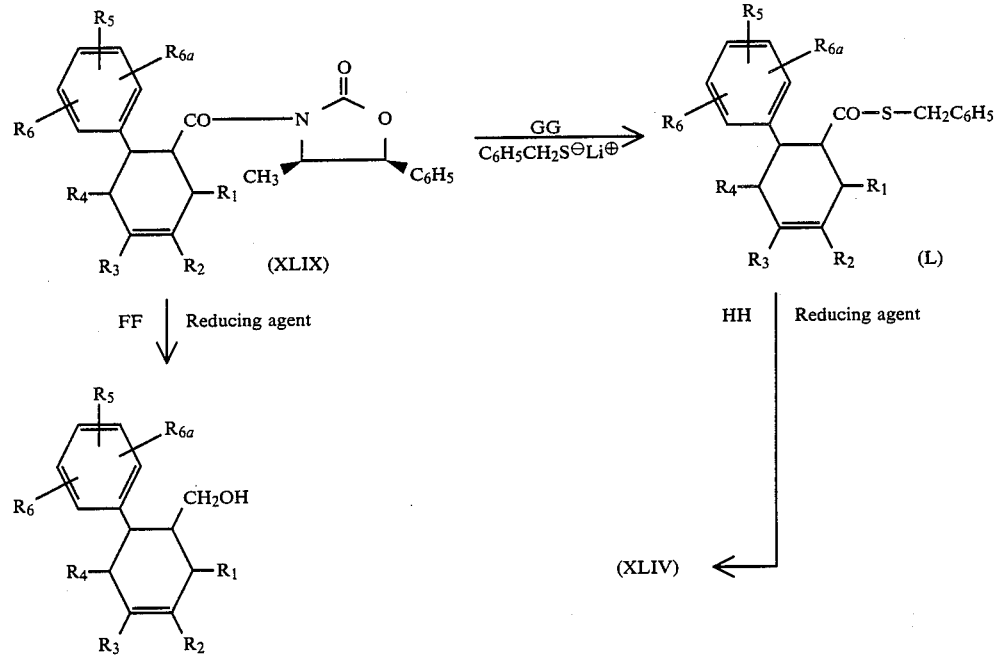
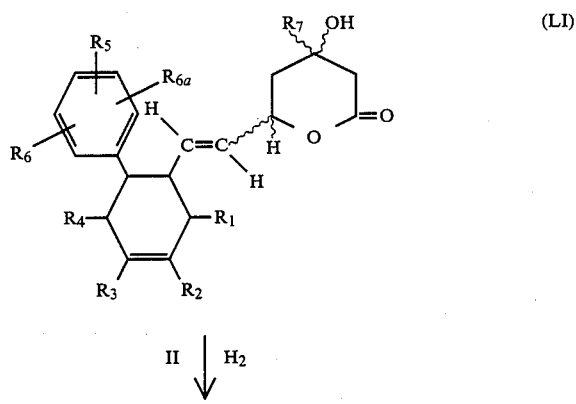
Reaction Scheme VIII
The compounds of Formula I wherein X is —CH$_2$CH$_2$—, Z is a group of Formula b, and the broken line represents two hydrogen atoms are preferably synthesized as follows:
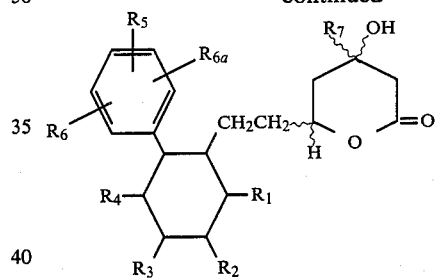
Reaction Scheme IX
The compounds of Formula I wherein Z is a group of Formula a wherein R$_8$ is R$_9$ or M may also be synthesized as follows:
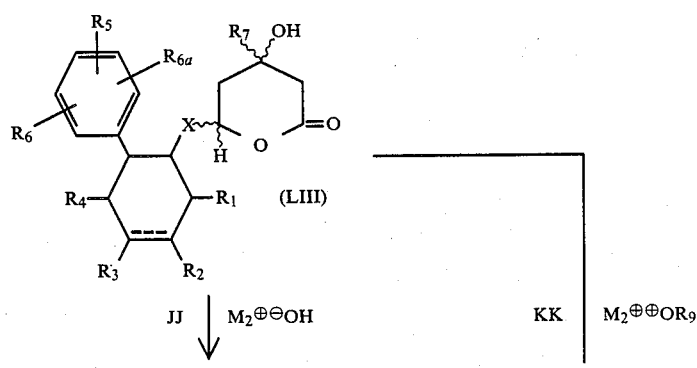

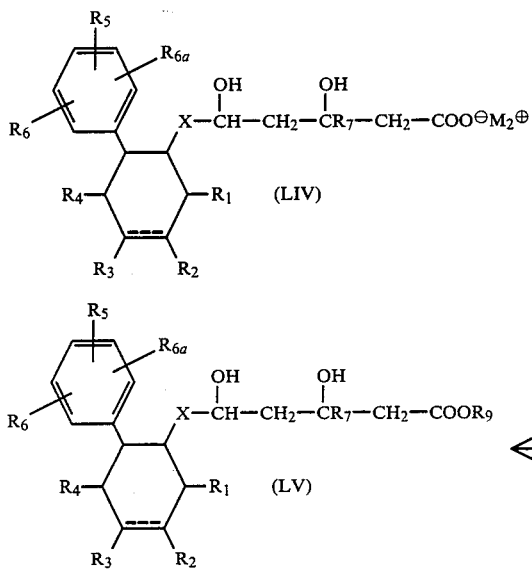

In the above formulae, $R_{7a}$ is $C_{1-3}$alkyl, preferably $C_{1-2}$alkyl and most preferably methyl, each $R_{11}$ is independently $C_{1-2}$alkyl, preferably methyl, each $R_{12}$ is independently n-$C_{1-4}$alkyl, preferably n-butyl, $R_{13}$ is $C_{1-3}$alkyl, preferably $C_{1-2}$alkyl, Y is chloro or bromo, preferably chloro, $M_2$ is M, preferably sodium or potassium, and each of the other variables is as defined above.

As utilized herein, terms such as "solvent" and "solvent system" embrace mixtures of solvents and imply that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "an inert atmosphere", as utilized herein, means an atmosphere that does not react with any of the reactants, intermediates or end products or otherwise interfere with the reaction. While a carbon dioxide atmosphere is suitable for some reactions, the inert atmosphere is usually nitrogen, helium, neon, argon or krypton, or a mixture thereof, and preferably is dry nitrogen. Most reactions, including those where the use of an inert atmosphere is not specified, are carried out under such an atmosphere for convenience.

In Reaction A, the dianion of the acetoacetic acid ester of Formula V is generated with 2-2.2 equivalents of a strong base per mole of said ester, and the resulting dianion is reacted with the aldehyde of Formula IV.

Among the strong bases that may be employed in Reaction A are n-butyllithium, lithium diisopropylamide and sodium hydride. However, sodium hydride can be used only to generate a monoanion; it cannot be used to generate a dianion. Consequently, when sodium hydride is used to generate the monoanion, 1-1.1 equivalents thereof are utilized, and then 1-1.1 equivalents of n-butyllithium or lithium diisopropylamide are utilized to generate the dianion from the monoanion. When lithium diisopropylamide is utilized, it is usually produced in situ prior to the addition of the acetoacetic acid ester of Formula V by reacting n-butyllitium and diisopropylamine in a 1:1 molar ratio at $-20°-10°$ C. for 10-60 minutes in the solvent to be used for the reaction. Lithium diisopropylamide is the preferred strong base.

In Reaction A the molar ratio of the acetoacetic acid ester of Formula V to the aldehyde of Formula IV is preferably 1-2.5:1, more preferably 1.2-2.2:1 and most preferably 1.3-1.7:1. The first step of the reaction, i.e., the generation of the dianion of the acetoacetic acid ester of Formula V, is conveniently carried out at $-50°-10°$ C., preferably $-5°-5°$ C., and the second step of the reaction, i.e., the reaction of the dianion with the aldehyde of Formula IV is conveniently carried out at $-80°-0°$ C., preferably $-50°--15°$ C. and most preferably $-30°--15°$ C. Both steps of the reaction are relatively rapid; the dianion is typically generated over the course of 20-80 minutes while the reaction of the dianion with the aldehyde of Formula IV is generally run for 20-240 minutes, preferably 20-60 minutes. Both steps of the reaction are carried out under an inert atmosphere in an anhydrous inert organic solvent, for example an ether such as tetrahydrofuran, diethyl ether, 1,2-dimethoxyethane or 1,2-di-ethoxyethane, particularly tetrahydrofuran. The resulting compound of Formula VI is a mixture of stereoisomers.

In Reaction B, the keto group of the ketoester of Formula VI is reduced to a hydroxy group with a mild reducing agent such as sodium borohydride or a complex of t-butylamine and borane in an inert organic solvent such as a lower alkanol, preferably ethanol, conveniently at a temperature of $-10°-30°$ C., utilizing at least 1, for example 2-4, equivalents of transferable hydride per mole of compound of Formula VI, under an inert atmosphere. The reaction time is suitably 1-8 hours. The dihydroxyesters of Formula VII exist in numerous stereoisomeric forms; however, if an optically pure starting material of Formula VI is utilized, only two optical isomers (diastereoisomers) of the resulting dihydroxyester of Formula VII are obtained.

However, it is preferred to utilize a stereoselective reducing agent in Reaction B to maximize production of a mixture of the erythro stereoisomers of which the preferred stereoisomer (as set forth above) is a constituent. Reaction B is preferably carried out in three steps. In the first step, the ketoester of Formula VI is treated with a tri-(primary or secondary $C_{2-4}$alkyl)borane, preferably triethylborane or tri-n-butylborane, and air to form a complex. The molar ratio of the trialkylborane to the ketoester of Formula VI is preferably 1–1.2:1, more preferably 1.02–1.1:1, and 0.5–8 liters, preferably 0.75–6.5 liters, of air (at 25° C. and 760 mm. Hg) per mole of the ketoester are used. The reaction temperature is suitably 0°–50° C., preferably 20°–30° C., and the reaction time is suitably 1–6 hours, preferably 1.5–3.5 hours. Step one is carried out in an anhydrous inert organic solvent, preferably an ether solvent such as tetrahydrofuran, diethyl ether, 1,2-dimethoxyethane or 1,2-diethoxyethane, with tetrahydrofuran and mixtures thereof with methanol being most preferred. When a mixture of tetrahydrofuran and methanol wherein the ratio of the former to the latter is 3–4:1 (by volume) is used, the ratio of the erythro isomers to the threo isomers may be as high as 20–100:1. In the second step, the complex is reduced with sodium borohydride, preferably in the same solvent as utilized for the first step, at $-100°--40°$ C., preferably $-90°--70°$ C., for 1–24 hours, preferably 2.5–18 hours. Preferably, 0.4–1.5, more preferably 1.0–1.05, moles of sodium borohydride per mole of the ketoester of Formula VI are utilized. In the third step, the product of the second step is treated with aqueous, e.g., 30%, hydrogen peroxide, an aqueous buffer, preferably a phosphate buffer, having a pH of 7.0–7.2 (e.g., a 0.047M. sodium phosphate/0.024M. potassium phosphate/0.054M. sodium hydroxide buffer or a 0.039M. sodium dihydrogen phosphate/0.061M. disodium hydrogen phosphate buffer) and a lower alkanol, preferably methanol, to obtain the dihydroxyester of Formula VII. A large molar excess of hydrogen peroxide, e.g., 30–100, more typically 50–70, moles per mole of the ketoester of Formula VI, is employed. Thus, when 30% aqueous hydrogen peroxide is employed, 2.6–8.6 liters, more typically 4.3–6.0 liters, preferably 5.5–5.9 liters, per mole of the ketoester of Formula VI are usually employed. Sufficient buffer to maintain the desired pH (7.0–7.2) must be utilized; when 30% aqueous hydrogen peroxide and either aforementioned phosphate buffer are utilized, 1–2 liters of said buffer per liter of 30% aqueous hydrogen peroxide are used. As for the lower alkanol, it is preferable to employ 1–3 liters, more preferably 1.5–2.5 liters, per liter of 30% aqueous hydrogen peroxide. The third step may be carried out by slowly adding a solution of the hydrogen peroxide, buffer and lower alkanol to the reaction mixture obtained from the second step, stirred at $-80°--40°$ C., preferably $-80°--70°$ C., allowing the reaction mixture to warm to 20°–30° C. and stirring for 3–16, preferably 12–16, hours. It may also be carried out by isolating the crude product of the second step, dissolving it in methanol, adding thereto at $-20°-10°$ C., preferably $-10°-5°$ C., the phosphate buffer followed by the hydrogen peroxide and stirring at 20°–30° C., preferably 20°–25° C., for 2–4, preferably 2–3, hours. Alternatively, the product of the second step may be treated with a large excess of methanol, e.g., 50–100 moles per mole of the ketoester of Formula VI, at 20°–60° C. for 0.75–5 hours, perferably 2–4 hours.

Reactions C and I are conventional basic hydrolyses of esters. The dihydroxyester of Formula VII or diester of Formula XVII is treated with at least one equivalent of an inorganic hydroxide per mole of ester group to be hydrolyzed. Preferably, each mole of dihydroxyester of Formula VII is treated with 1–1.3, preferably 1–1.2, and each mole of diester of Formula XVII is treated with 2–2.6, preferably 2–2.4, equivalents of sodium hydroxide or potassium hydroxide in a mixture of water and a water-miscible organic solvent such as a lower alkanol, preferably methanol or ethanol, at a temperature of 20° C. to reflux, preferably not in excess of 80° C., most preferably 20°–70° C. As is well-known, the reaction time is inversely related to the reaction temperature; however, a reaction time of 1–4 hours is generally acceptable. However, when it is desired to isolate the carboxylate salt of Formula VIII or XVIII, it is preferable to employ slightly less than one equivalent of the inorganic hydroxide per mole of ester group, e.g., 0.9–0.98, preferably 0.95, equivalents thereof per mole of dihydroxyester of Formula VII and 1.8–1.95, preferably 1.9, equivalents thereof per mole of diester of Formula XVII.

Reactions D and J are conventional acidifications of a carboxylate salt to the corresponding carboxylic acid. The reactions are effected by treating the salt of Formula VIII or XVIII with a slight (e.g., 10%) molar excess of a dilute aqueous acid, e.g., dilute (1–2N.) hydrochloric acid, the pH of the reaction medium being about 6.

In Reactions E and K, the 3,5-dihydroxypentanoic acid of Formula IX or XIX is cyclized to form the lactone of Formula X or XX, respectively, by heating in an anhydrous inert organic solvent, for example a hydrocarbon such as benzene, toluene or a xylene, or a mixture thereof, preferably at 75° C.-reflux, more preferably not in excess of 150° C., for 3–18 hours, optionally using a Dean-Stark apparatus if the solvent forms an azeotrope with water. The reaction is conveniently run by refluxing the dihydroxypentanoic of Formula IX or XIX in benzene or toluene for 4–8 hours, e.g., for 5–6 hours.

Reaction F is a three-step process for converting the aldehyde of Formula IV to the hydroxyketone of Formula XII. In the first step, the ketone of Formula XI is reacted with a di-n-$C_{1-4}$alkylboryl, preferably di-n-butylboryl, trifluoromethanesulfonate, in the presence of a tertiary amine, for example, a $C_{1-4}$alkyl-di-$C_{1-3}$alkylamine such as triethylamine or, preferably, a hindered amine such as ethyldiisopropylamine, preferably at $-80°--70°$ C., in an anhydrous inert organic solvent, for example, an ether such as tetrahydrofuran or, preferably, diethyl ether, for, preferably, 0.5-4 hours, more preferably 0.5-1 hour, under an inert atmosphere. Preferably 1-1.1 moles, more preferably 1-1.05 moles and most preferably 1 mole, of each of the three reactants per mole of the aldehyde of Formula IV to be used in the second step are employed. The molar quantity of the tertiary amine should not be less than the molar quantity of each of the other two reactants. In the second step, the reaction mixture of the first step is reacted with the aldehyde of Formula IV, preferably at $-80°-0°$ C., in an anhydrous inert organic solvent, preferably the same as utilized in the first step, for, preferably, 1-4 hours, more preferably 1.5-4 hours, preferably under an inert atmosphere. Preferably, the reaction is commenced at $-80°--70°$ C. and, after 0.5-1 hour, the reaction mixture is allowed to warm to 0° C. and maintained at this temperature for the balance of the reaction time. It is preferred to then quench the reaction mixture with an excess of a phosphate buffer having a pH of 7-7.2, e.g., the buffers mentioned in connection with Reaction B, and extract the borate ester intermediate with, for example, diethyl ether. In the third step the borate ester intermediate is oxidized to the hydroxyketone of Formula XII with an oxidizing agent such as hydrogen peroxide, conveniently 30% aqueous hydrogen peroxide, in a lower alkanol, preferably methanol. A large molar excess of hydrogen peroxide, e.g., 5-50 moles per mole of the aldehyde of Formula IV, is usually utilized. When 30% aqueous hydrogen peroxide is utilized, it is preferable to use at least 2 liters, preferably 3-6 liters, of the lower alkanol per liter of the hydrogen peroxide. The reaction time for the third step is suitably 2-16 hours, and the reaction temperature is suitably 0°-30° C. Preferably, the third step is commenced at 0° C. and, after 0.25-1 hour, the reaction mixture is allowed to warm to room temperature and maintained at room temperature for the balance of the reaction time (for at least 1.5 hours).

In Reaction G, the hydroxyketone of Formula XII is esterified with, for example, an acid anhydride of Formula XIII or an acyl halide of Formula XIV in the presence of a base such as pyridine or triethylamine. Conveniently, the hydroxyketone of Formula XII is treated with 1-1.1 moles of said acid anhydride or acyl halide (per mole of the hydroxyketone of Formula XII) in an excess of pyridine at 20°-50° C. for 2-8 hours.

Reaction H is also a two-step reaction. First, the ester of Formula XVI is treated with a strong base such as lithium diisopropylamide to form a monoanion, the molar ratio of the latter to the former being 1-1.1:1. The reaction is carried out in an anhydrous inert organic solvent, for example an ether such as diethyl ether, 1,2-dimethoxyethane, 1,2-diethoxyethane or, preferably, tetrahydrofuran, under an inert atmosphere. The reaction temperature is conveniently $-80°-0°$ C., and the reaction time is usually 15-60 minutes. In the second step, said monoanion is reacted with the ketoester of Formula XV under an inert atmosphere in the same solvent system as utilized for the first step, the molar ratio of the ester of Formula XVI to the ketoester of Formula XV usually being 1-4:1. The reaction temperature is conveniently $-80°--10°$ C., and the reaction time is typically 15-90 minutes. The reaction is usually commenced at $-80°--60°$ C., and the temperature of the reaction mixture is gradually allowed to rise to as high as $-10°$ C. as the reaction proceeds.

Reactants L and L' are conventional acid catalyzed esterifications. Conveniently, the dihydroxypentanoic acid of Formula IX or XIX is treated with a large excess of the alcohol of Formula XXI at 20°-40° C. for 2-12 hours in the presencre of a catalytic amount of an acid such as p-toluenesulfonic acid. The excess alcohol serves as the solvent. The reaction may be run in an inert organic solvent, e.g., an ether such as tetrahydrofuran, and must be run in such a solvent if the alcohol of Formula XXI is not a liquid. When the reaction is run in an inert organic solvent, the molar ratio of the alcohol to the dihydroxypentanoic acid is typically 1-5:1, usually 2-4:1.

In Reactions M, S and X, the alcohol of Formula XXIII, XXXI or XXXVII is oxidized under mild conditions to the aldehyde of Formula XXIV, XXXII or XXXVIII, respectively. Particularly suitable oxidizing agents include pyridinium dichromate, pyridinium chlorochromate and manganese dioxide. The reaction is conveniently run by treating the alcohol of Formula XXIII, XXXI or XXXVII with 1-2 moles, preferably 1.2-1.8 moles, of pyridinium dichromate or pyridinium chlorochromate or 5-50 moles, preferably 10-20 moles, of manganese dioxide per mole of the alcohol in an inert organic solvent such as a halogenated hydrocarbon, e.g., methylene chloride, at 20°-30° C. for 1-5 hours, preferably 2-4 hours, when pyridinium chlorochromate is used, 12-24 hours, preferably 15-18 hours, when pyridinium dichromate is used or 12-72 hours, preferably 16-60 hours, when manganese dioxide is used. Manganese dioxide is only suitable for Reaction S.

In Reaction N, the aldehyde of Formula XXIV is reacted with lithium ethoxyacetylide to obtain, after treatment of the initially obtained acetylenic alcohol with acid, the ester of Formula XXV. The first step of the reaction is conveniently run by reacting the aldehyde of Formula XXIV with 1-1.5, preferably 1.1-1.4, molesof lithium ethoxyacetylide (conveniently obtained by reacting n-butyllithium and ethoxyacetylene in a molar ratio of 1-1.02:1 in a mixture of anhydrous tetrahydrofuran and n-hexane at $-80°--70°$ C. for 1 hour under an inert atmosphere) for 0.5-6 hours, preferably 2-5 hours, under an inert atmosphere in an anhydrous inert organic solvent, e.g., an ether such as diethyl ether, tetrahydrofuran, 1,2-dimethoxyethane or 1,2-diethoxyethane, or a mixture thereof with a hydrocarbon such as n-hexane, preferably mixture of anhydrous tetrahydrofuran and n-hexane, at $-80°--40°$ C., preferably $-80°--70°$ C. In the second step, the obtained acetylenic alcohol is rearranged to obtain the ester of Formula XXV by contact with an acid in the presence of water. While virtually any strong acid may be utilized, the use of p-toluenesulfonic, methanesulfonic or ethanesulfonic acid or, especially, a sulfo group-containing ion exchange resin such as Amberlyst-15 is preferred. It is convenient to utilize 1-2 equivalents of acid per mole of the aldehyde of Formula XXIV. When Amberlyst-15 is utilized, it is convenient to utilize 125-175 g. thereof per mole of the aldehyde of Formula XXIV. The reaction is run in a mixture of water and an inert organic solvent, e.g., an ether solvent such as diethyl ether, 1,2-dimethoxyethane, 1,2-diethoxyethane or, especially, tetrahydrofuran, 5% aqueous tetrahydrofuran being particularly convenient, especially when a sulfo group-containing ion exchange resin is utilized. The reaction temperature is preferably 20°-50° C., more preferably 20°-30° C., and the reaction time is conveniently 3-24 hours, usually 12-24 hours.

Reaction O is a conventional basic hydrolysis of a carboxylic acid ester followed by the acidification of the obtained carboxylate salt to obtain the carboxylic acid. While the reaction conditions set forth above for Reactions C, D, I and J may be utilized, it is particularly convenient to reflux a solution of the ester of Formula XXV in a mixture of water and a lower alkanol such as methanol or ethanol containing an excess of sodium hydroxide or potassium hydroxide (e.g., 1.2-15 equivalents of base per mole of the ester of Formula XXV) for 1-6, preferably 2-4.5 hours. The reaction mixture is then cooled to 10°-30° C., preferably 20°-30° C., and acidified, conveniently with 2-6N. hydrochloric acid, to obtain the carboxylic acid of Formula XXVI.

Reactions P and CC are conveniently run by reacting the carboxylic acid of Formula XXVI or XLVI with a large excess of a thionyl halide of Formula XXVII, preferably thionyl chloride, e.g., 1.5-10, preferably 3-9, moles of the thionyl halide per mole of the carboxylic acid of Formula XXVI or XLVI in an anhydrous inert organic solvent, preferably a hydrocarbon such as benzene, toluene or xylene, or a mixture thereof, at a temperature of 50° C.-reflux, preferably not in excess of 150° C., more preferably 60°-80° C., for, for example, 4-24 hours.

In Reactions Q and DD, the acyl halide of Formula XXVIII or XLVII is reacted with the compound of Formula XXIX to form the compound of Formula XXX or XLVIII. The compound of Formula XXIX is formed by reacting n-butyllithium and cis-4R-methyl-5S-phenyloxazolidin-2-one (compound 2a of Evans et al., J. Am. Chem. Soc. 103, 2127-2129 (1981)), the molar ratio of the former to the latter preferably being 1-1.05:1, in a mixture of tetrahydrofuran and n-hexane at −80°-−20° C., more preferably −70°-−50° C. for, preferably, 10-60 minutes, more preferably 10-20 minutes, under an inert atmosphere. The obtained compound of Formula XXIX is reacted with the acyl halide of Formula XXVIII or XLVII, the molar ratio of the former to the latter preferably being 1-1.05:1, in an anhydrous inert organic solvent, preferably an ether such as tetrahydrofuran, diethyl ether, 1,2-dimethoxyethane or 1,2-diethoxyethane, or a mixture thereof with a hydrocarbon such as n-hexane, more preferably a mixture of tetrahydrofuran and n-hexane, preferably at −80°-−20° C., more preferably −70°-−50° C., for preferably 1-4, more preferably 1.5-2.5, hours. The product of Reaction DD (the compound of Formula XLVIII) is optically pure. However, unless the compound of Formula XXVIII is optically pure, the product of Reaction Q is a mixture of diastereoisomers (two if the compound of Formula XXVIII is a racemate) which may be separated by conventional means such as fractional crystallization, column chromatography and, particularly, high pressure liquid chromatography utilizing, for example, a silica gel column.

In Reaction R, the compound of Formula XXX is reduced to the alcohol of Formula XXXI with a strong reducing agent. Among the reducing agents that may be employed are the aluminum hydride reducing agents such as diisobutylaluminum hydride and lithium aluminum hydride, the latter being preferred. At least two equivalents of transferable hydride per mole of the compound of Formula XXX are required. When lithium aluminum hydride is utilized, typically 0.6-1.5, preferably 0.8-1.2, moles thereof per mole of the compound of Formula XXX are employed. The reaction is run in an anhydrous inert organic solvent, preferably an ether solvent, e.g., diethyl ether, tetrahydrofuran, 1,2-dimethoxyethane or 1,2-diethoxyethane, or a mixture thereof, preferably at a temperature of −50°-0° C., more preferably −40°-−30° C., preferably for 15-60, more preferably 20-40, minutes, in order to minimize formation of an undesired by-product.

The alcohol of Formula XXIII is converted to the tosylate of Formula XXXIII in Reaction T. The tosylate is conveniently synthesized by reacting the alcohol of Formula XXIII with p-toluenesulfonyl chloride, the molar ratio of the latter to the former preferably being 1-1.1:1 in an inert organic solvent, preferably a liquid tertiary amine such as pyridine, at, preferably, 0°-30° C. for, for example, 3-18 hours. When the solvent is not a base, at least 1 mole, e.g., 1-25 moles, of an organic base such as pyridine (per mole of the alcohol of Formula XXIII) should be added to the reaction mixture.

In Reaction U, the iodide of Formula XXXIV is conveniently synthesized by reacting the tosylate of Formula XXXIII with, preferably, 2-5, more preferably 3-4, moles of sodium iodide per mole of the tosylate of Formula XXXIII for, preferably, 18-24 hours at, preferably, 20°-60° C. in an inert solvent, preferably acetone.

The iodide or tosylate of Formula XXXIII or XXXIV is converted to the ester of Formula XXXVI by reaction with the anion of the ester of Formula XXXV in Reactions V and V'. In the first step, the ester of Formula XXXV is reacted with a strong base such as lithium diisopropylamide, the molar ratio of the strong base to the ester preferably being 1-1.02:1, in an anhydrous inert organic solvent, preferably an ether solvent, e.g., diethyl ether, 1,2-dimethoxyethane or, preferably, tetrahydrofuran, under an inert atmosphere, preferably at −80°-−70° C. for 30-60 minutes, to obtain the anion of the ester. In the second step, the obtained anion is reacted with the compound of Formula XXXIII or XXXIV, the molar ratio of the latter to the former preferably being 1-1.02:1, in an anhydrous inert organic solvent such as the solvents utilizable for the first step, preferably the same solvent, under an inert atmosphere, preferably at −80°-−20° C., for, for example, 3-5 hours. The reaction is usually commenced at −80°-−70° C. and the reaction mixture is gradually allowed to warm to −30°-−20° C. as the reaction proceeds.

In Reactions W, AA, FF, HH and HH′, the compound of Formula XXXVI, XLIII, XLIX, L or XXXA is reduced to the alcohol of Formula XXXVII (Reaction W), XLIV (Reactions AA, FF and HH) or XXXI (Reaction HH′) with a strong reducing agent. Among the reducing agents that may be employed are the aluminum hydride reducing agents such as diisobutylaluminum hydride and lithium aluminum hydride, the latter being preferred. At least two equivalents of transferable hydride per mole of the compound of Formula XXXVI, XLIII, XLIX, L or XXXA are required. When lithium aluminum hydride is utilized, one usually employs 0.6-1.5, preferably 0.8-1.2, moles thereof per mole of the compound to be reduced. The reaction is run in an anhydrous inert organic solvent such as those utilizable in Reaction R. The reaction temperature is conveniently 0°-40° C., preferably 20°-30° C., and the reaction time is usually 1-4 hours (3-4 hours for Reactions HH and HH′). When $R_1$ is alkyl, Reaction FF does not give an acceptable yield of the compound of Formula XLIV and, therefore, Reactions GG and HH must be used. In most other cases, the yield of the desired product is better when Reactions GG and HH or Reactions GG′ and HH′ are utilized than when Reaction F or Reaction R, respectively, is utilized. When Reactions GG and HH or Reactions GG′ and HH′ are utilized, it is often preferable to run them without isolating the compound of Formula L, i.e., as a one-pot reaction sequence.

Reaction Y is a three-step reaction. In the first step, cis-1-ethoxy-2-tri-n-butylstannylethylene (prepared by adding 1 equivalent of ethoxyacetylene to tri-n-butyltin hydride at 50° C. over a period of 1 hour and heating under an inert atmosphere at 50°-55° C. for 3 hours and at 60°-70° C. for 1 hour) is reacted for 1-3, preferably 2, hours with 1-1.05 equivalents of n-butyllithium per mole of the tin compound at −78° C. in anhydrous tetrahydrofuran under an inert atmosphere, the n-butyllithium/n-hexane solution being added dropwise, to form cis-1-lithium-2-ethoxyethylene. In the second step, said lithium compound is reacted with the aldehyde of Formula XXIV in the same solvent at −80°-−40° C., preferably at −80°-−70° C., under an inert atmosphere for 1-8, preferably 1.5-5, hours to form an enol ether intermediate. The molar ratio of the starting ethoxyethenyltin compound to the aldehyde of Formula XXIV is 1-1.15:1. The crude enol ether intermediate may be utilized in the third step. However, the yield and purity of the α,β-unsaturated aldehyde of Formula XXXII is often improved if the enol ether intermediate is isolated prior to use in the third step. In the third step, the enol ether intermediate is treated with a catalytic amount of p-toluenesulfonic acid (e.g., 0.5-2 g., preferably 1.2-1.8 g., of said acid per mole of the aldehyde of Formula XXIV) in an inert aqueous organic solvent, e.g., a mixture of water and tetrahydrofuran, for 1-5, preferably 2-4.5, hours, at 20°-40° C., preferably 20°-30° C.

Reactions Z and EE are Diels-Alder reactions. The dienophile of Formula XLI or XLVIII is reacted with the diene of Formula XLII, preferably at 180°-220° C., especially 190°-210° C., for, for example, 2-5 days and, preferably, in the presence of a catalytic amount (e.g., 0.5-3 g. per mole of the diene) of hydroquinone (to minimize polymerization of the diene). If necessary, a pressure vessel is utilized. The reaction may be run neat when at least one of the reactants is a liquid under the reaction conditions; in such a situation, an excess of such reactant(s) serves as the solvent. An inert organic solvent may, however, be utilized (and must be utilized when neither reactant is a liquid under the reaction conditions). Suitable solvents include the hydrocarbons, e.g., mono-, di- and tri-alkylbenzenes having a boiling point of at least 125° C., e.g., the xylenes. When a solvent is utilized, the molar ratio of the reactants may be 1:1. However, an excess of one reactant, usually the cheaper one, e.g., 1.1-5 moles of one reactant per mole of the other, is usually utilized.

The configuration about the double bonds of the dienophile of Formula XLI or XLVIII and the diene of Formula XLII determines the geometric relationship of the substituents on the cyclohexene ring of the obtained compound of Formula XLIII or XLIX as set forth in the following table:

| Dienophile of Formula XLI or XLVIII | Diene | | $R_1$ | $R_4$ | $\phi$ | CO |
|---|---|---|---|---|---|---|
| trans | trans, trans | (1) | α | α | α | β |
|  |  | (2) | α | α | β | α |
| trans | cis, trans | (1) | α | β | α | β |
|  |  | (2) | α | β | β | α |
| cis | trans, trans | (1) | α | α | α | α |
|  |  | (2) | α | α | β | β |
| cis | cis, trans | (1) | α | β | α | α |
|  |  | (2) | β | α | α | α |

$\phi$ = the $R_5$-bearing phenyl (or naphthyl) group CO = the —COOR$_{13}$ group of the compound of Formula XLIII and the 4R-methyl-5S-phenyloxazolidin-2-one-3-carbonyl group of the compound of Formula XLIX α and β denote the relative positions of the substituents in question The Diels-Alder reaction results in mixtures of the possible geometric (and optical) isomers. Such mixtures (other than racemates from Reaction Z) may be separated by conventional means such as fractional crystallization, column chromatography, thin layer preparative chromatography and, especially, high pressure liquid chromatography utilizing, for example, a silica gel column. Alternatively, the mixture may be used in one or more of the following reactions with separation of the isomers after one or more additional reactions. For example, it is usually easier to separate compounds of Formula XLIV than compounds of Formula XLIII. Consequently, the mixture of products from Reaction Z is usually utilized in Reaction AA.

Reactions BB and II are conventional metal-catalyzed hydrogenation reactions. They are conveniently run by contacting a solution of the compound of Formula XLIV or LI with an excess of hydrogen (more than one mole per mole of the compound of Formula XLIV and more than two moles per mole of the compound of Formula LI) in the presence of a catalyst such as platinum oxide, palladium/carbon (e.g., 5%) or Raney nickel (e.g., 10-50, preferably 20-40, g. of the catalyst per mole of the compound of Formula XLIV or LI) until one mole of hydrogen per mole of the compound of Formula XLIV or two moles of hydrogen per mole of the compound of Formula LI are taken up. The reaction is run in an inert organic solvent such as a lower alkanol (e.g., methanol and ethanol) or a lower alkyl ester of a lower alkanoic acid (e.g., methyl acetate and ethyl acetate), preferably at 20°-30° C. The initial hydrogen pressure is conveniently 20-30 p.s.i.

Reactions GG and GG' are two-step processes for converting the compound of Formula XLIX or XXX to the thioester of Formula L or XXXA. In the first step, benzyl mercaptan is reacted with n-butyllithium to form lithium benzylmercaptide. It is conveniently carried out by reacting n-butyllithium (conveniently 1.6M. n-butyllithium/n-hexane) with benzyl mercaptan, the molar ratio of the latter to the former preferably being 1.01-1.3:1, more preferably 1.2-1.3:1, in an anhydrous inert organic solvent, preferably an ether solvent such as diethyl ether, 1,2-dimethoxyethane, 1,2-diethoxyethane or, especially, tetrahydrofuran, or a mixture thereof with a liquid hydrocarbon such as n-hexane, under an inert atmosphere for, preferably, 10-30 minutes, more preferably 10-15 minutes, at, preferably, $-20°-5°$ C., more preferably 0° C. In the second step, the lithium benzylmercaptide is reacted with the compound of Formula XLIX or XXX to form the thioester of Formula L or XXXA in an anhydrous inert organic solvent such as those utilized in the first step, preferably the same solvent, under an inert atmosphere. The molar ratio of lithium benzylmercaptide (calculated from the amount of n-butyllithium) to the compound of Formula XLIX or XXX is preferably 1-3:1, more preferably 1.1-1.5:1, when the starting material is relatively sterically non-hindered (e.g., a compound of Formula XXX) and 1.5-2.5:1 when the starting material is relatively sterically hindered (e.g., a compound of Formula XLIX) and most preferably 2-2.5:1 when the starting material is relatively sterically hindered. When the starting material is relatively sterically non-hindered, the reaction time is conveniently 1-12 hours, preferably 2-4 hours, and when it is relatively sterically hindered, the reaction time is conveniently 12-24 hours, more preferably 12-18 hours. The reaction temperature is preferably 0°-30° C. It is convenient to commence the reaction at 0° C. and to allow the reaction mixture to slowly warm to room temperature as the reaction proceeds.

In Reaction JJ the lactone of Formula LIII is hydrolyzed to the carboxylate salt of Formula LIV. It is convenient to react the lactone of Formula LIII with 1 equivalent of an inorganic base such as sodium hydroxide or potassium hydroxide per mole of the lactone in an inert aqueous organic solvent, preferably a mixture of water and a lower alkanol, e.g., methanol or, preferably, ethanol, at, preferably, 20°-75° C., more preferably 40°-70° C., for, preferably, 1-6 hours, more preferably 2-4 hours, to obtain the carboxylate salt. When it is desired to isolate the carboxylate salt, it is often advantageous to employ slightly less than 1 equivalent, e.g., 0.95-0.99 equivalent, per mole of the lactone.

In Reaction KK the lactone of Formula LIII is reacted with at least 2 moles, e.g., 2-10 moles, preferably 2.05-2.5 moles, of the compound of the formula $M_2^{\oplus \ominus}OR_9$ per mole of the lactone at 0°-70° C., preferably 20°-25° C., for 2-12 hours in an inert anhydrous organic solvent, e.g., an ether such as tetrahydrofuran or, if a liquid, an alcohol of the formula $R_9OH$, $R_9$ being the same as in the compound of the formula $M_2^{\oplus \ominus}OR_9$.

As is evident to those in the art, a cis lactone of Formula LIII yields a threo carboxylate salt of Formula LIV or ester of Formula LV, and a trans lactone of Formula LIII yields an erythro carboxylate salt of Formula LIV or ester of Formula LV. A mixture of two diastereoisomeric cis lactones of Formula LIII yields a mixture of two diastereoisomeric threo carboxylate salts of Formula LIV or esters of Formula LV, a single enantiomer of a trans lactone of Formula LIII (e.g., the 4R,6S enantiomer) yields a single enantiomer of the corresponding erythro carboxylate salt of Formula LIV or ester of Formula LV (e.g., the 3R,5S enantiomer), etc. The reverse is true in Reactions E and K, i.e., a threo carboxylic acid yields a cis lactone and an erythro carboxylic acid yields a trans lactone, the enantiomeric composition of the product corresponding to the enantiomeric composition of the starting material.

The compounds of Formulae V, XI, XIII, XIV, XVI, XXI, XXVII, XXIX, XXXV, XL-XLII and XLVI are known or, if unknown, may be synthesized by processes analogous to those described in the literature for similar known compounds.

The product of each reaction may, if desired, be purified by conventional tecuhniques such as recrystallization (if a solid), column chromatography, preparative thin layer chromatography, gas chromatography (if sufficiently volatile) or fractional distillation under high vacuum (if sufficiently volatile). Often, however, the crude product of one reaction may be employed in the following reaction without purification.

As is evident to those in the art, each of the compounds of Formulae IV, XXIII-XXVI, XXVIII, XXXII-XXXIV, XXXVI-XXXVIII and XLIII-XLV may exist in two or more geometric isomeric forms (the $R_5$-bearing phenyl (or naphthyl) group and the $-CH_2OH$, $-X-CHO$, etc. group may be cis or trans to each other), more than two geometric isomeric forms when at least one of $R_1$ and $R_4$ is alkyl and/or when the broken line represents two hydrogen atoms and at least one of $R_2$ and $R_3$ is $C_{1-3}$alkyl. Each such geometric isomeric form may exist in two stereosiomeric forms, i.e., as a racemate. However, the number of isomeric forms in which any particular compound actually exists is determined by the compound from which it was synthesized and the reaction by which it was synthesized, i.e., whether the reaction produces a mixture of isomers (geometric and/or optical) even when the starting material is a single isomer. For example, when a diene of Formula XLII wherein $R_1$ and $R_4$ are identical and $R_2$ and $R_3$ are identical is utilized in Reaction Z, the product of Formula XLIII is a mixture of two geometric isomers which may be separated, each of which is a racemate. When just one of the racemates is utilized in Reaction AA, the resulting compound of Formula XLIV is also a racemate which may be resolved into its two enantiomeric forms. Similarly, when an optically pure single isomer of Formula XXXI is utilized in Reaction S, the resulting compound of Formula XXXII is also an optically pure single isomer.

The compounds of Formulae XXX-XXXI, XLIX and L also may exist in two or more geometric isomer forms. However, since an optically pure compound of Formula XXIX is utilized in the synthesis, no such geometric isomeric form may exist as a racemate; rather, they may exist in two diastereoisomeric forms which, as set forth above, may be separated. The same is true for the compounds of Formulae XXXII and XLIV if synthesized from a compound of Formula XXXI, XLIX or L.

Reactions A and F result in the formation of an additional center of asymmetry as do Reactions B (unless a stereospecific process is utilized) and H. Consequently, if an optically pure single compound of Formula IV is utilized in Reaction A or Reaction F, the resulting compound of Formula VI or XII is a mixture of two diastereoisomers which may be separated as set forth infra. If, however, a racemic single compound of Formula IV is utilized in either reaction, the resulting compound is a mixture of four stereoisomers (two pairs of diastereoisomers) which may be separated into two racemates, each of which may be resolved as set forth infra. Likewise, if an optically pure single isomer of Formula VI or XV is used in Reaction B or Reaction H, respectively, the resulting product of Formula VII or XVII is a mixture of two diastereoisomers (unless a stereospecific reducing agent is utilized in Reaction B in which event an optically pure compound of Formula VII is obtained). If, however, a racemic single isomer is utilized, the resulting compound is a mixture of four stereoisomers (two pairs of diastereoisomers) (unless a stereospecific reducing agent is utilized in Reaction B in which event only two diastereoisomers are obtained).

The obtained mixtures of stereoisomers may be separated by conventional means. For example, diastereoisomers may be separated by fractional crystallization (if a solid), column chromatography, preparative thin layer chromatography and high pressure (performance) liquid chromatography (HPLC).

Techniques for resolving a racemate into its two optically active enantiomers are known. For example, a racemic compound having a carboxylic acid group may be reacted with an optically pure organic base having at least one center of asymmetry to form a mixture of diastereoisomer salts that may be separated by fractional crystallization, column chromatography, etc. or it may be reacted with an optically pure alcohol having at least one center of asymmetry to form a mixture of diastereoisomeric esters which may be separated by conventional techniques such as those set forth above or below. Likewise, a racemic compound having a carboxylic acid, acyl halide, ester or lactone group may be reacted with an optically pure organic base, i.e., an amine, to form a mixture of diastereoisomeric amides that may be separated by conventional means, e.g., fractional crystallization, column chromatography and-/or HPLC. For example, a racemic lactone of Formula LIII may be reacted with an excess of R-(+)-$\alpha$-methylbenzylamine (or the corresponding S-(−) compound) to form a mixture of two diastereoisomeric $\alpha$-methylbenzylamides which may be separated by, for example, column chromatography on a silica gel column and/or by HPLC using a Partisil column. Often it is desirable to utilize both techniques, i.e., to partially separate the diastereoisomers by column chromatography and to purify each fraction by HPLC. Typically, the $\alpha$-methylbenzylamides are synthesized by reacting the racemic lactone with a large molar excess of the amine at 20°-25° C. for 16-24 hours. The reaction is run neat, with the excess amine serving as the solvent. After the reaction, the excess amine is removed by vacuum distillation at 25°-35° C. After separation, each chiral amide may be hydrolyzed to the corresponding, for example, sodium, salt by, for example, refluxing with 1.5-3, preferably 2-2.2, equivalents of a base such as sodium hydroxide for 5-25 hours in a mixture of water and ethanol. The resulting salts may be converted to the corresponding free acids, esters, lactones and other salts by conventional means such as the reactions set forth in Reaction Schemes V and VIII. On the other hand, a racemic compound having at least one hydroxy group may be esterified with an opically pure carboxylic acid having at least one center ofasymmetry to form a mixture of diastereoisomeric esters or it may be reacted with an equimolar amount of an optically pure trisubstituted silyl halide having an asymmetric silicon atom, e.g., (−)-$\alpha$-naphthylphenylmethylchlorosilane (Sommer et al., J. Am. Chem. SOc. 80, 3271 (1958).), in, for example, the presence of 2 moles of imidazole per mole of the silyl halide in dry dimethylformamide at 20°-32° C. for 12-24 hours to form a mixture of two diastereoisomeric silyloxy compounds, which mixture may be separated by conventional techniques. For example, diastereoisomeric (−)-$\alpha$-naphthylphenylmethylsilyl derivatives of a lactone of Formula LIII may be separated on a silica column having covalently bound L-phenylglycine. After separation, the optically pure salts, amides, esters or silyloxy compounds are reconverted to the corresponding carboxy group- or hydroxy group-containing compounds with retention of optical purity. For example, (−)-$\alpha$-naphthylphenylmethylsilyl and other silyl groups may be cleaved by treatment with, for example, 1-4 moles of tetra-n-butylammonium fluoride per mole of the silyloxy compound and 1-2 moles, preferably 1.2-1.5 moles, of glacial acetic acid per mole of tetra-n-butylammonium fluoride at 20°-60° C., preferably 20°-25° C., for 2-30 hours, preferably 3-8 hours, in an anhydrous ether solvent, preferably tetrahydrofuran, the silyloxy compound being added to a solution of the other reactants.

The compounds of Formula I (and each and every subscope thereof) wherein Z is a group of Formula a and $R_8$ is hydrogen may be converted into the corresponding compounds wherein $R_8$ is a cation, e.g., M, or $R_9$ by conventional means, e.g., Reaction L or by treatment with a base having M as its cation, e.g., a base of the formula $M^{+q}(OH)_q$, wherein q is 1, 2 or 3. Likewise, those wherein Z is a group of Formula a and $R_8$ is a cation, e.g., M, may be converted into the corresponding compounds wherein $R_8$ is hydrogen or any other cation, e.g., M, by conventional means, e.g., Reactions D and J and ion exchange.

Since any compound of Formula I wherein Z is a group of Formula a wherein $R_8$ is a cation other than M may be converted into the corresponding compound wherein $R_8$ is hydrogen, M or $R_9$, the compounds of Formula I wherein Z is a group of Formula a and $R_8$ is a pharmaceutically unacceptable cation are also within the scope of this invention since they are useful as intermediates. However, such compounds are not compounds of Formula I as utilized in this application, except where indicated to the contrary.

Besides having the utility set forth below, every compound of Formula I is useful as an intermediate in the synthesis of one or more other compounds of Formula I utilizing the reactions set forth above. Reactions C-E, L' and I-L may be utilized to convert compounds of Formula I wherein Z is a group of Formula a into the corresponding compounds wherein Z is a group of Formula b and, as set forth above, into the corresponding compounds wherein Z is a group of Formula a having a different $R_8$ group, and Reactions JJ and KK may be utilized to convert compounds of Formula I wherein Z is a group of Formula b into the corresponding compounds wherein Z is a group of Formula a.

Also within the scope of this invention are the intermediates of Formulae IV, VI, XII, XV, XVII, XXIII-XXVI, XXVIII, XXX-XXXIV, XXXVI-XXXVIII, XLIII-XLV and XLVIII-L. The preferences for each variable and for the positions of the substituents on the cyclohexane or cyclohexane ring (i.e., the positions of the substituents on the ring ($\alpha$ or $\beta$) relative to each other) are the same as those set forth for the compounds of Formula I, with the preferred groups of such compounds including those that correspond to Groups (i)-(vi) and (x)-(xv) and, preferably, have the preferences set forth in the paragraph following Group (xviii).

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates, and, therefore, as hypolipoproteinemic and anti-atherosclerotic agents. The biological activity of the compounds of Formula I is demonstrated in the following three tests:

Test A. In Vitro Microsomal Assay of HMG-CoA Reductase Inhibition:

200 µl. aliquots (1.08-1.50 mg./ml.) of rat liver microsomal suspensions, freshly prepared from male Sprague-Dawley rats (150-225 g. body weight), in Buffer A with 10 mmol. dithiothreitol are incubated with 10 µl. of a solution of the test substance dissolved in dimethylacetamide and assayed for HMG-CoA reductase activity as described by Ackerman et al., J. Lipid Res. 18, 408-413 (1977), the concentration of the test substance in the assay system being 0.01-2,000 µmolar. In the assay the microsomes are the source of the HMG-CoA reductase enzyme which catalyzes the reduction of HMG-CoA to mevalonate. The assay employs a chloroform extraction to separate the product, [$^{14}$C]-mevalonolactone, formed by the HMG-CoA reductase reaction from the substrate, [$^{14}$C]HMG-CoA. [$^{3}$H]mevalonolactone is added as an internal reference. Inhibition of HMG-CoA reductase is calculated from the decrease in specific activity [$^{14}$C/$^{3}$H]mevalonate) of test groups compared to controls.

Test B. In Vitro Cell Culture Cholesterol Biosynthesis Screen:

The cell culture is prepared as follows: Stock monolayer cultures of the Fu5AH rat hepatoma cell line (originally obtained from G. Rothblat; see Rothblat, Lipids 9, 526-535 (1974) are routinely maintained in Eagle's Minimum Essential Medium (EMEM) supplemented with 10% fetal bovine serum (FBS) in 75 cm$^2$. tissue culture flasks. For these studies, when the cultures reach confluence, they are removed by mild enzymatic treatment with 0.25% trypsin in Hank's balanced salt solution (without calcium and magnesium). After centrifugation of the cell suspension and aspiration of the enzymatic solution, the cell pellet is resuspended in an appropriate volume of media for seeding into 60 mm. tissue culture dishes. The cultures are incubated at 37° C. in an atmosphere of high humidity and 5% carbon dioxide. When the cultures are confluent (approximately 5 days), they are ready for use. The culture media is aspirated from the dishes and replaced with 3 ml. of EMEM supplemented with 5 mg./ml. of delipidized serum protein (DLSP) prepared by the method of Rothblat et al., In Vitro 12, 554-447 (1976). Replacement of the FBS with DLSP has been shown to stimulate the incorporation of [$^{14}$C]acetate into sterol by removing the exogenous sterol supplied by the FBS, thereby requiring the cells to synthesize sterol. Enhanced 3-hydroxy-3-methylglutaryl Coenzyme A reductase (HMG-CoA reductase) activity is measurable in the cells in response to the lack of exogenous sterol. Following approximately 24 hours incubation at 37° C. in the DLSP supplemented media, the assay is initiated by the addition of 3 µCi of [$^{14}$C]acetate and the test substances solubilized in dimethylsulfoxide (DMSO) or distilled water. Solvent controls and compactin-treated controls are always prepared. Triplicate 60 mm. tissue culture dishes are run for each group. After 3 hours incubation at 37° C., the cultures are examined microscopically using an inverted phase contrast microscope. Notations are made of any morphological changes which may have occurred in the cultures. The media is aspirated and the cell layer is gently washed twice with 0.9% sodium chloride solution (saline). The cell layer is then harvested in 3 ml. of 0.9% saline by gentle scraping with a rubber policeman and transferred to a clean glass tube with Teflon lined cap. The dishes are rinsed with 3 ml. of 0.9% saline and rescraped, and the cells are combined with the first harvest. The tubes are centrifuged at 1500 r.p.m. for 10 minutes in an IEC PR-J centrifuge, and the supernatant is aspirated.

The cells are then extracted as follows: One ml. of 100% ethanol is added to the cell pellet followed by sonication for 10 seconds with a "LO" setting of 50 on a Bronwell Biosonik IV. One hundred $\mu$l. are taken for protein determination. One ml. of 15% potassium hydroxide (KOH) is added, and the samples are thoroughly vortexed. Saponification is accomplished by heating the ethanol-KOH treated samples at 60° C. for 60 minutes in a water bath. Following dilution of the samples with 2 ml. of distilled water, they are extracted three times with 7 ml. of petroleum ether. The petroleum ether extracts are then washed three times with 2 ml. of distilled water and finally taken to dryness under a stream of nitrogen.

The obtained samples are then analyzed by thin layer chromatography (TLC) as follows: Residues from the petroleum ether extraction are taken up in a small volume of hexane and spotted on silica gel 60 TLC plates (E. Merck). Development of the plates is carried out in a three phase solvent system consisting of 150 parts by volume hexane: 50 parts by volume diethyl ether: 5 parts by volume glacial acetic acid. Visualization is accomplished in an iodine vapor chamber. The plates are divided into five sections such that each section contains the molecules having the following approximate Rf value: section 1-0-0.4, section 12-0.4-0.55, section 3-0.55-0.7, section 4-0.7-0.9 and section 5-0.9-1.0. Section 2 contains the non-saponifiable sterols. The five sections of the TLC plates are scraped into scintillation vials. Blanks are also prepared from scraping of chromatographed non-labelled standards. ACS ® scintillation cocktail is added, and the radioactivity is determined in a liquid scintillation spectrometer. [$^{14}$C]hexadecane standards are used to determine counting efficiencies. The total protein content of the samples is determined employing the Bio-Rad Protein Assay System.

The results are reported as disintegrations per minute per mg. protein (d.p.m./mg. protein) for each of the five TLC sections. Mean d.p.m./mg. protein±standard error of the mean are calculated, and drug treated means are compared for percentage change (%$\Delta$) and statistical significance with solvent control means. TLC section 2 data is taken as a measure of HMG-CoA reductase activity inhibition.

Test C. In Vivo Cholesterol Biosynthesis Inhibition Test:

In vivo studies utilize male Wistar Royal Hart rats weighing 150±20 g. which have been kept for 7–10 days on an altered light cycle (6:30 A.M.–6.30 P.M. dark) housed two per cage and fed powdered Purina Rat Chow and water ad libitum. Three hours before the diurnal maximum of cholesterol synthesis at mid-dark, the rats are administered the test substances dissolved or as a suspension in 0.5% carboxymethylcellulose in a volume of 1 ml./100 g. body weight. Controls receive vehicle alone. One hour after receiving the test substance, the rats are injected intraperitoneally with about 25 $\mu$Ci/100 g. body weight of sodium [1-$^{14}$C]acetate 1–3 mCi/mmol. Two hours after mid-dark, blood samples are obtained under sodium hexobarbitol anesthesia, and the serum separated by centrifugation. (The dosage of the test substance is 0.01–200 mg./kg. body weight.)

Serum samples are saponified and neutralized, and the 3$\beta$-hydroxysterols are precipitated with digitonin basically as described by Sperry et al., J. Biol. Chem. 187, 97 (1950). The [$^{14}$C]digitonides are then counted by liquid scintillation spectrometry. After correcting for efficiencies, the results are calculated in nCi (nanocuries) of sterol formed per 100 ml. of serum. Inhibition of sterol synthesis is calculated from the reduction in the nCi of sterols formed from test groups compared to controls.

The following results were obtained:

| Test A: | Example 3 | $IC_{50}$ = 8.13 $\mu$molar |
|---|---|---|
| | Example 3A | $IC_{50}$ = 3.23 $\mu$molar |
| | Example 5 | $IC_{50}$ = 1.19 $\mu$molar |
| | Example 5A | $IC_{50}$ = 0.54 $\mu$molar |
| | Example 6 | $IC_{50}$ = 5.57 $\mu$molar |
| | Example 67B | $IC_{50}$ = 1369 $\mu$molar |
| | Example 73 | $IC_{50}$ = 450 $\mu$molar |
| | Example 74 | $IC_{50}$ = 116 $\mu$molar |
| | Example 79 | $IC_{50}$ = 29 $\mu$molar |
| | Example 85 | $IC_{50}$ = 7.2 $\mu$molar |
| | Example 86 | $IC_{50}$ = 141 $\mu$molar |
| | Mevinolin | $IC_{50}$ = 0.14 $\mu$molar |
| | Compactin | $IC_{50}$ = 0.94 $\mu$molar |
| Test B: | Example 3 | $IC_{50}$ = 1.2 $\mu$molar |
| | Example 5 | $IC_{50}$ = 0.6 $\mu$molar |
| | Example 74 | $IC_{50}$ = 5.8 $\mu$molar |
| | Example 79 | $IC_{50}$ = 4.8 $\mu$molar |
| | Example 86 | $IC_{50}$ = 5.4 $\mu$molar |
| | Compactin | $IC_{50}$ = 0.08 $\mu$molar |

$IC_{50}$ is the concentration of the test substance in the assay system observed or calculated to produce a 50% inhibition of HMG-CoA reductase activity (Test A) or sterol biosynthesis (Test B).

| Test C: | Example 3 | $ED_{50}$ = 2.4 mg./kg. |
|---|---|---|
| | Example 5 | $ED_{50}$ = 2.07 mg./kg. |
| | Example 74 | $ED_{50}$ = 20 mg./kg. |
| | Example 79 | −62% at 5.9 mg./kg. |
| | Mevinolin | $ED_{50}$ = 0.41 mg./kg. |
| | Compactin | $ED_{50}$ = 3.5 mg./kg. |

The $ED_{50}$ is the dose of the test substances observed or calculated to produce a 50% inhibition of 3$\beta$-hydroxysterol synthesis.

As set forth above, the compounds of Formula I (including each and every subgroup thereof set forth in the specification and/or the claims) inhibit cholesterol biosynthesis and are useful for lowering the blood cholesterol level in animals, particularly mammals and more particularly larger primates and, therefore, as hypolipoproteinemic and anti-atherosclerotic agents.

The compounds of Formula I may be formulated in conventional pharmaceutical compositions and administered by conventional modes of administration. The compounds of each and every subgroup thereof in the specification and/or claims may likewise be formulated into conventional pharmaceutical compositions.

The compounds of Formula I may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspension. The compositions may be prepared by conventional means. The preferred pharmaceutical compositions from the standpoint of ease of preparation and administration are solid compositions, particularly tablets and capsules.

The precise dosage of the compounds of Formula I to be employed for inhibiting cholesterol biosynthesis depends upon several factors including the host, the nature and the severity of the condition being treated, the mode of administration and the particular compound employed. However, in general, satisfactory inhibition or reduction of cholesterol biosynthesis (i.e., satisfactory reduction of the blood cholesterol level and satisfactory treatment of hyperlipoproteinemia and atherosclerosis) is achieved when a compound of Formula I is administered orally at a daily dosage of 0.3–100, e.g, 1–20, mg./kg. body weight or, for most larger primates, a daily dosage of 20–2000 mg., suitably 20–750, e.g., 20–200, mg. for the more active compounds. For the compound of Example 5, the oral dosage is indicated to be 0.3–1.5 mg./kg. body weight or, for most larger primates, it is indicated to be 20–100 mg.

The daily dosage is usually divided into two to four equal portions or administered in sustained release form. A typical oral dosage of the compound of Example 5 is indicated to be 25 mg. three times a day. Usually, a small dosage is administered initially, and the dosage is gradually increased until the optimal dosage for the host under treatment is determined. For administration by injection, a dosage somewhat lower than would be used for oral administration of the same compound to the same host having the same condition is usually employed. However, the above dosages are also typically used for i.v. administration.

A typical dosage unit for oral administration may contain 5 to 500 mg. of a compound of Formula I. Preferred dosage units contain 5 to 50 mg., especially 10 to 50 mg., of a compound of Formula I such as the compound of Example 5.

The compounds of Formula I (include those of each and every subgroup thereof) may be formulated into such pharmaceutical compositions containing an amount of the active substance that is effective for inhibiting cholesterol biosynthesis, such compositions in unit dosage form and such compositions comprising a solid pharmaceutically acceptable carrier.

A representative formulation prepared by conventional techniques for encapsulation in a hard gelatin capsule is:

| Compound of Formula I, e.g., the compound of | |
|---|---|
| Example 5 | 25 mg. |
| Corn starch | 224 mg. |
| Magnesium stearate | 1 mg. |

A representative formulation suitable for preparing tablets by conventional means is:

| Compound of Formula I, e.g., the compound of | |
|---|---|
| Example 5 | 10 mg. |
| Polyvinylpyrrolidone USP | 5 mg. |
| Powdered lactose | 174 mg. |
| Corn starch | 10 mg. |
| Magnesium stearate | 1 mg. |

The following examples show representative compounds encompassed by this invention and their synthesis. However, it should be understood that they are for purposes of illustration only.

EXAMPLE 1

Ethyl (E)-3,5-dihydroxy-7-[2′α,5′α-dimethyl-6′α-(4″-fluorophenyl)cyclohex-3′-en-1′βS-yl]hept-6-enoate

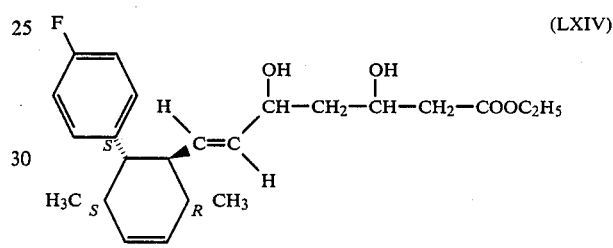
(LXIV)

Step 1

Ethyl trans-4-fluorocinnamate

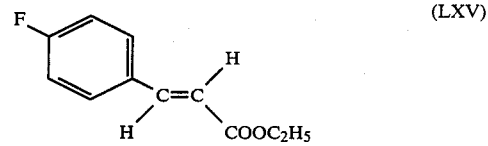
(LXV)

9.6 g. of sodium hydride (50% in mineral oil, pentane washed) is added in small portions to a solution of 45 g. of triethyl phosphonoacetate in 400 ml. of dry tetrahydrofuran stirred at 0° C. under nitrogen. The reaction mixture is allowed to warm to room temperature, stirred at room temperature for 1 hour and cooled to 10° C., a solution of 24.8 g. of 4-fluorobenzaldehyde in 25 ml. of dry tetrahydrofuran is adde dropwise, and the reaction mixture is stirred at room temperature for 18 hours, the reaction mixture being maintained under nitrogen throughout. Water is added to the reaction mixture. The reaction mixture is extracted twice with diethyl ether, and the organic layers are combined, dried over anhydrous sodium sulfate and evaporated at reduced pressure to an oil. The oil is distilled at 15 mm. Hg. to obtain the product (28.3 g. (73%)), b.p. 142° C.

Step 2 (Reaction Z)
Ethyl 2α,5α-dimethyl-6-(4'-fluorophenyl)cyclohex-3-enecarboxylate

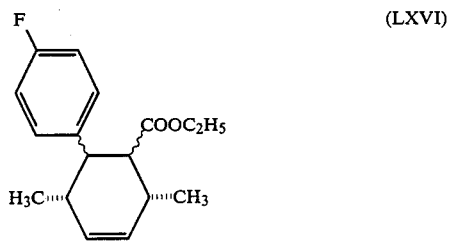
(LXVI)

A mixture of 28.0 g. of ethyl trans-4-fluorocinnamate (Compound LXV), 32.0 g. of E2,E4-hexadiene and 0.6 g. of hydroquinone is heated at 200° C. for 4 days in a steel pressure vessel. The resulting reaction mixture is chromatographed on a Waters Prep-500 high pressure liquid chromatography apparatus having a silica gel column and using 5% ethyl acetate/n-hexane to eluate the product, an oil, a mixture of isomers in a ratio of 76:24 (39.7 g. (99%)). In one racemate the 4-fluorophenyl group is cis to the methyl groups and trans to the ethoxycarbonyl group and in the other it is trans to the methyl groups and the ethoxycarbonyl group.

N.M.R. (CDCl$_3$): 0.63–1.15δ (9H multiplet) 2.12–2.78 (3H multiplet) 3.13 (0.25H doublet of a doublet) 3.32 (0.75H doublet of a doublet) 3.74–4.05 (2H multiplet) 5.45–5.83 (2H multiplet) 6.80–7.25 (4H multiplet)

Step 3 (Reaction AA)
(±)-2α,5α-Dimethyl-6α-(4'-fluorophenyl)cyclohex-3-ene-1β-methanol

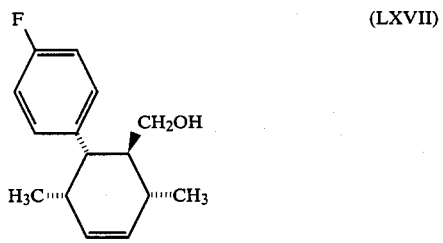
(LXVII)

A solution of 39.5 g. of Compound LXVI (the 76:24 mixture of isomers of Step 2) in 100 ml. of dry tetrahydrofuran is added dropwise to a suspension of 5.5 g. of lithium aluminum hydride in 300 ml. of dry tetrahydrofuran stirred at room temperature under nitrogen. The reaction mixture is stirred at room temperature for 3 hours under nitrogen, and saturated sodium sulfate solution (about 20 ml.) is carefully added until a thick precipitate forms. The precipitate is removed by filtration and washed well with diethyl ether. The filtrate and the diethyl ether washings are combined and evaporated at reduced prssure to an oil (about 30 g.). The oil is chromatographed on a Waters Prep-500 high pressure liquid chromatography apparatus having a silica gel column and using 20% methyl t-butyl ether/n-hexane to elute the racemic product, an oil (21.2 g. (63%)).

I.R. (CHCl$_3$): 3623, 3010, 2965, 2885, 1509 and 1237 cm.$^{-1}$ and others

N.M.R. (CDCl$_3$): 0.76δ (3H doublet) 1.00 (1H singlet) 1.11 (3H doublet) 1.70 (1H multiplet 2.24 (1H multiplet) 2.45 (1H multiplet) 3.12 (1H doublet of a doublet) 3.63 (2H multiplet) 5.52 (1H broad doublet) 5.70–5.80 (1H multiplet 6.96–7.17 (4H multiplet)

The isomeric racemic product, (±)-2α,5α-dimethyl-6β-(4'-fluorophenyl)cyclohex-3-ene-1α-methanol, an oil, is also eluted from the column (4.4 g.).

N.M.R. (CDCl$_3$): 0.76δ (3H doublet) 0.94 (1H singlet) 1.01 (3H doublet) 2.05–2.67 (4H multiplet) 3.22 (2H multiplet) 5.46–5.85 (2H multiplet) 6.85–7.24 (4H multiplet)

Step 4 (Reaction M)
(±)-2α,5α-Dimethyl-6α-(4'-fluorophenyl)cyclohex-3-ene-1β-carboxaldehyde

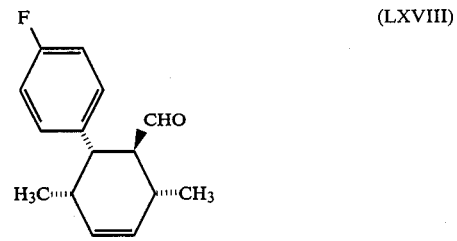
(LXVIII)

A solution of 18.5 g. of racemic Compound LXVII (from Step 3) in 100 ml. of methylene chloride is added dropwise to a suspension of 50.0 g. of pyridinium dichromate in 250 ml. of methylene chloride stirred at room temperature. The reaction mixture is stirred at room temperature for 18 hours and filtered through a pad of silica gel, and the filtrate is evaporated at reduced pressure to obtain the racemic product as an oil (15.2 g. (83%)).

I.R. (CHCl$_3$): 1723, 1512 and 1234 cm.$^{-1}$ and others

N.M.R. (CDCl$_3$): 0.65δ (3H doublet) 1.04 (3H doublet) 2.26–2.68 (3H multiplet) 3.35 (1H doublet of a doublet) 5.52 (1H broad doublet) 5.73–5.83 (1H multiplet) 6.92–7.14 (4H multiplet) 9.33 (1H doublet)

Step 5 (Reaction N)
Ethyl (±)-(E)-3-[2'α,5'α-dimethyl-6'α-(4''-fluorophenyl)cyclohex-3'-en-1'β-yl]propenoate

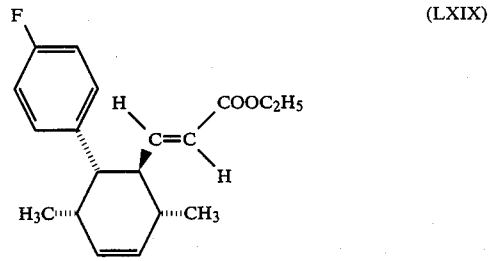
(LXIX)

(a) 5.5 g. of n-butyllithium (55 ml. of a 1.6M. solution in n-hexane) is added dropwise to a solution of 6.0 g. of ethoxyacetylene in 300 ml. of dry tetrahydrofuran stirred at −78° C. under nitrogen. Stirring at −78° C.

under nitrogen is continued for 1 hour. A solution of 15.2 g. of racemic Compound LXVIII (from Step 4) in 20 ml. of dry tetrahydrofuran is added dropwise, and the reaction mixture is stirred at −78° C. under nitrogen for 4 hours. Water is added, and the mixture is extracted once with methyl t-butyl ether and once with methylene chloride. The organic phases are combined, dried over anhydrous sodium sulfate and evaporated at reduced pressure to obtain the intermediate acetylenic alcohol (18.8 g. (95%)).

(b) 9.2 g. of Amberlyst-15 resin is added to a solution of 18.4 g. of the acetylenic alcohol of Part (a) of this step in 250 ml. of 5% aqueous tetrahydrofuran, and the reaction mixture is stirred at room temperature for 24 hours. The resin is removed by filtration, and the solvent is evaporated at reduced pressure to obtain the racemic product as an oil (18.3 g. (99%)).

N.M.R. (CDCl$_3$): 0.70δ (3H doublet) 1.01 (3H doublet 1.23 (3H doublet 2.0–2.62 (3H multiplet) 3.10 (1H doublet of a doublet) 4.10 (2H quarter) 5.40–5.75 (2H multiplet) 5.75 (1H doublet) 6.46 (1H doublet of a doublet) 6.80–7.10 (4H multiplet)

Step 6 (Reactin O)

(±)-(E)-3-[2'α,5'α-Dimethyl-6'α-(4''-fluorophenyl)cyclohex-3'-en-1'β-yl]propenoic acid

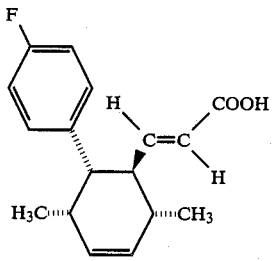

(LXX)

250 ml. of 2N. aqueous sodium hydroxide is added to a solution of 18.3 g. of racemic Compound LXIX (from Step 5) in 1 l. of ethanol, and the reaction mixture is refluxed for 4 hours, allowed to cool and evaporated at reduced pressure. The residue is dissolved in water, and the resulting solution is washed with diethyl ether, acidified with 6N. hydrochloric acid and extracted twice with methylene chloride. The organic phases are combined, dried over anhydrous sodium sulfate and evaporated at reduced pressure to an oil which, upon standing, yields the crystalline racemic product (14.0 g. (84%)), m.p. 162°–165° C.

I.R. (CHCl$_3$): 3016, 2971, 2885, 2676, 2560, 1697, 1649 and 1242 cm.$^{-1}$ and others N.M.R. (CDCl$_3$): 0.72δ (3H doublet) 1.02 (3H doublet) 2.05–2.37 (2H multiplet) 2.45 (1H multiplet) 3.10 (1H doublet of a doublet) 5.52 (1H broad doublet) 5.71–5.81 (1H multiplet) 5.76 (1H doublet) 6.57 (1H doublet of a doublet) 6.85–7.03 (4H multiplet) acid proton not seen Step 7 (Reaction P)

(±)-(E)-3-[2'α,5'α-Dimethyl-6'α-(4''-fluorophenyl)cyclohex-3'-en-1'β-yl]propenoyl chloride

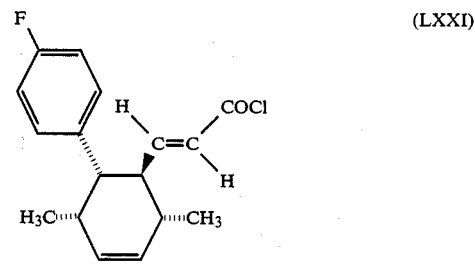

(LXXI)

30 ml. of thionyl chloride is added to a suspension of 14.0 g. of Compound LXX (from Step 6) in 20 ml. of toluene, and the resulting mixture is stirred at 70° C. for 24 hours, allowed to cool and evaporated at reduced pressure to obtain the racemic product as an oil (16 g. (>100%)).

Step 8 (Reaction Q)

3-[(E)-3'-(2''α,5''α-Dimethyl-6''α-(4'''-fluorophenyl)cyclohex-3''-en-1''βS-yl)-1'-oxopropenyl]-cis-4R-methyl-5S-phenyloxazolidin-2-one

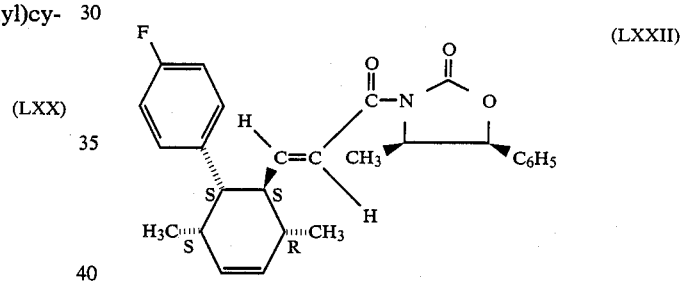

(LXXII)

(a) 3.5 g. of n-butyllithium (35 ml. of a 1.6M. solution in n-hexane) is added dropwise to a solution of 9.7 g. of cis-4R-metyl-5S-phenyloxazolidin-2-one in 250 ml. of dry tetrahydrofuran stirred at −65° C. under nitrogen, and the resulting solution is stirred under the same conditions for an additional 15 min. to obtain a solution of Compound XXIX.

(b) A solution of 16.0 g. of Compound LXXI (from Step 7) in 100 ml. of dry tetrahydrofuran is added dropwise to the solution of Compound XXIX from Part (a) of this step stirred at −65° C. under nitrogen, and the reaction mixture is stirred under the same conditions for an additional 2 hours. Water is added, and the obtained mixture is extracted twice with methyl t-butyl ether and once with methylene chloride. The organic phases are combined, dried over anhydrous sodium sulfate and evaporated at reduced pressure to obtain a mixture of diastereoisomers. The mixture is chromatographed on a Waters Prep-500 high pressure liquid chromatography apparatus having a silica gel column and using 15% ethyl acetate/n-hexane to elute the desired diastereoisomer. Trituration with diethyl ether yields the crystalline product (8.0 g. (35%)), m.p. 169°–171° C., [α]$_D$ = +25.4° (CHCl$_3$).

I.R. (CHCl₃): 1779, 1686, 1636 and 1355 cm.⁻¹ and others

N.M.R. (CDCl₃): 0.71δ (3H doublet) 0.86 (3H doublet) 1.05 (3H doublet) 2.13–2.4 (2H multiplet) 2.59 (1H multiplet) 3.16 (1H doublet of a doublet) 4.72 (1H multiplet) 5.53 (1H doublet) 5.65 (1H doublet) 5.74–5.85 (1H multiplet) 6.70 (1H doublet of a doublet) 6.87–7.50 (10H multiplet)

The absolute sterochemistry of this compound was determined by X-ray crystallography.

(c) The other diastereoisomer, 3-[(E)-3′-(2″β,5″β-dimethyl-6″β-(4‴-fluorophenyl)cyclohex-3″-en-1″αR-yl)-1′-oxopropenyl]cis-4R-methyl-5S-phenyloxazolidin-2-one, an oil, is also eluted from the column (8.4 g.). [α]_D = −22.4° (CHCl₃).

I.R. (CHCl₃): 1779, 1689, 1636 and 1356 cm.⁻¹ and others

N.M.R. (CDCl₃): 0.72δ (3H doublet) 0.87 (3H doublet) 1.06 (3H doublet) 2.1–2.4 (2H multiplet) 2.58 (1H multiplet) 3.13 (1H doublet of a doublet) 4.72 (1H multiplet) 5.54 (1H doublet) 5.66 (1H doublet) 5.75–5.85 (1H multiplet) 6.65 (1H doublet of a doublet) 6.9–7.5 (10H multiplet)

Step 9 (Reaction R)

(E)-3-[2′α,5′α-Dimethyl-6′α-(B 4″-fluorophenyl)cyclohex-3′-en-1′βS-yl]prop-2-en-1-ol

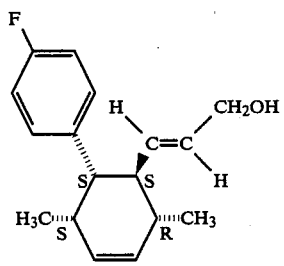
(LXXIII)

A solution of 8.6 g. of the diastereoisomer of compound LXXII of Part (b) of Step 8 ([α]_D = +25.4°) in 60 ml. of dry tetrahydrofuran is added dropwise to a mixture of 20 ml. of a 1M. solution of lithium aluminum hydride in anhydrous diethyl ether and 100 ml. of dry tetrahydrofuran stirred at −35° C. under nitrogen. After the addition, the reaction mixture is stirred at −35° C. under nitrogen for an additional 30 min., and saturated sodium sulfate solution (about 5 ml.) is slowly added at −35° C. until a precipitate forms. The precipitate is removed by filtration, and the filtrate is evaporated at reduced pressure to obtain an oil. The oil is chromatographed on a Waters Prep-500 high pressure liquid chromatography apparatus having a silica gel column and using 30% ethyl acetate/n-hexane to elute the product, an oil (2.3 g. (45%)).

N.M.R. (CDCl₃): 0.71δ (3H doublet) 1.04 (3H doublet) 1.5 (1H singlet) 2.0–2.38 (4H multiplet) 3.93 (2H doublet) 5.06–5.23 (1H multiplet) 5.49–5.68 (2H multiplet) 5.71–5.82 (1H multiplet) 6.88–7.06 (4H multiplet)

Step 10 (Reaction S)

(E)-3-[2′α,5′α-Dimethyl-6′α-(4″-fluorophenyl)cyclohex-3′-en-1′βS-yl]prop-2-enal

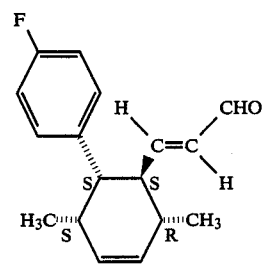
(LXXIV)

A solution of 2.2 g. of Compound LXXIII (from Step 9) in 15 ml. of methylene chloride is added dropwise to a suspension of 5.0 g. of pyridinium dichromate in 40 ml. of methylene chloride stirred at room temperature. The reaction mixture is stirred at room temperature for 18 hours, filtered through a pad of silica gel and evaporated at reduced pressure to obtain the product as an oil (1.6 g. (73%)).

N.M.R. (CDCl₃): 0.72δ (3H doublet) 1.04 (3H doublet) 2.10–2.40 (2H multiplet) 2.60 (1H multiplet) 3.15 (1H doublet of a doublet) 5.54 (1H multiplet) 5.75–5.87 (1H multiplet) 6.08 (1H doublet of a doublet) 6.37 (1H doublet of a doublet) 6.85–7.07 (4H multiplet) 9.28 (1H doublet)

Step 11 (Reaction A)

Ethyl (E)-7-[2′α,5′α-dimethyl-6′α-(4″-fluorophenyl)cyclohex3′-en-1′βS-yl]-5-hydroxy-3-oxohept-6-enoate

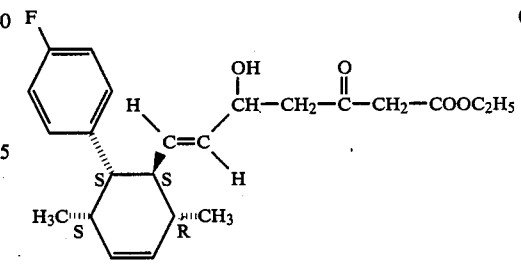
(LXXV)

1.67 g of n-butyllithium (1.6M. in n-hexane) is added to a solution of 2.58 g. of diisopropylamine in 100 ml. of dry tetrahydrofuran stirred at 0° C. under nitrogen. A solution of 1.7 g. of ethyl acetoacetate in 10 ml. of dry tetrahydrofuran is added dropwise, the reaction mixture is stirred at 0° C. for 1 hour and cooled to −20° C., a solution of 2.58 g. of Compound LXXIV (from Step 11) in 25 ml. of dry tetrahydrofuran is added dropwise, and the reaction mixture is stirred at −20° C. for 4 hours, the reaction mixture being maintained under nitrogen throughout. Saturated ammonium chloride solution is added, and the reaction mixture is extracted twice with methyl t-butyl ether. The organic phases are combined, dried over anhydrous sodium sulfate and evaporated at reduced pressure to obtain the crude product, a mixture of two diastereoisomers, as an oil (4.9 g. (100%)).

N.M.R. (CDCl₃): 0.71δ (1.5H doublet) 0.72 (1.5H doublet) 1.01 (1.5H doublet) 1.04 (1.5H doublet) 1.28 (3H triplet) 2.0–2.6 (6H multiplet) 3.0 (1H multiplet) 3.36 (2H doublet) 4.12–4.45 (3H multiplet) 5.0–5.56 (3H multiplet) 5.71–5.81 (1H multiplet) 6.86–7.07 (4H multiplet)

Step 12 (Reaction B)

Ethyl (E)-3,5-dihydroxy-7-[2'α,5'α-dimethyl-6'α-(4''-fluorophenyl)cyclohex-3'-en-1'βS-yl]hept-6-enoate

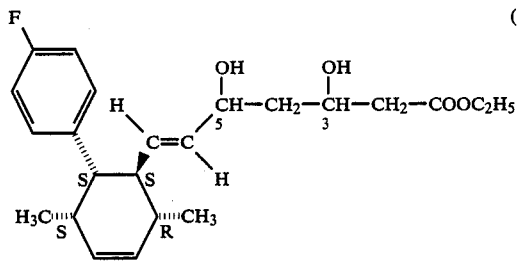

(LXIV)

10.5 ml. of a 1.0M. solution of triethylborane in dry tetrahydrofuran is added to a solution of 4.0 g. of Compound LXXV (from Step 11) in 100 ml. of dry tetrahydrofuran stirred at room temperature under nitrogen, 8.0 ml. of air (at 25° C. and 760 mm. Hg.) is bubbled in, and the reaction mixture is stirred at room temperature under nitrogen for 3 hours and cooled to −78° C. 400 mg. of sodium borohydride is added, and the reaction mixture is stirred at −78° C. under nitrogen for 18 hours. The reaction mixture is carefully quenched with saturated ammonium chloride solution and extracted with methylene chloride. The organic phase is evaporated at reduced pressure, and the residual oil is dissolved in 100 ml. of methanol. The methanolic solution is cooled to 5° C., and 80 ml. of an aqueous phosphate buffer having a pH of 7 (0.039M. sodium dihydrogen phosphate/0.061M. disodium hydrogen phosphate) is added followed by 60 ml. of 30% aqueous hydrogen peroxide. The resulting mixture is stirred at room temperature for 2.5 hours, the methanol is evaporated at reduced pressure, and the residue is extracted with methyl t-butyl ether. The organic phase is washed once with saturated sodium chloride solution, three times with dilute sodium bisulfite solution, once with 10% sodium bicarbonate solution and once with saturated sodium chloride solution and dried over anhydrous sodium sulfate. The solvent is evaporated at reduced pressure to obtain the product, a mixture of four diastereoisomers (the ratio of the erythro isomers to the threo isomers being about 6–7:1), as an oil (3.8 g. (95%)).

N.M.R. (CDCl₃): 0.7δ (3H doublet) 0.99 (1.5H doublet) 1.02 (1.5H doublet) 1.25 (3H triplet) 1.96–2.49 (10H multiplet) 2.9–3.05 (1H multiplet) 4.15 (1H multiplet) 4.15 (2H quartet) 5.0–5.58 (3H multiplet) 5.7–5.8 (1H multiplet) 6.85–7.07 (4H multiplet)

The mixture of four diastereoisomers may be separated by conventional means, the four isomers being the 3R,5R, 3R,5S, 3S,5R and 3S,5S isomers.

Example 1A (+)-2α,5α-Dimethyl-6α-(4'-fluorophenyl)cyclohex-3-ene-1βS-methanol

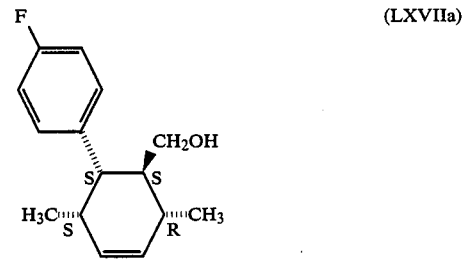

(LXVIIa)

Step 1

Trans-4-fluorocinnamic acid

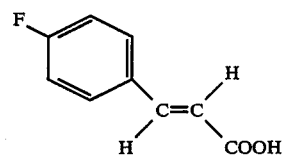

(LXXVI)

A solution of 4 g. of sodium hydroxide in 30 ml. of water is added to a solution of 19.4 g. (0.1 mole) of ethyl trans-4-fluorocinnamate (Compound LXV) in 350 ml. of ethanol, and the reaction mixture is stirred at 70° C. for 18 hours. The solvent is evaporated at reduced pressure, and the residue is dissolved in water. The solution is washed once with methyl t-butyl ether and acidified with 6N. hydrochloric acid. The resulting precipitate is washed twice with water and dried to obtain the product (15.5 g. (93%)). An analytical sample was recrystallized from ethyl acetate, m.p. 204°–206° C.

Step 2 (Reaction CC)

Trans-4-fluorocinnamoyl chloride

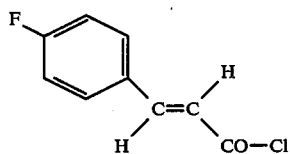

(LXXVII)

A mixture of 15.0 g. (0.09 mole) of trans-4-fluorocinnamic acid (Compound LXXVI) and 30 ml. (0.41 mole) of thionyl chloride in 100 ml. of toluene is stirred at 70° C. for 18 hours, and the solvent is evaporated at reduced pressure to obtain the crude product (17.5 g. (>100%)).

Step 3 (Reaction DD)

3-[(E)-3'-(4"-fluorophenyl)-1'-oxopropen-1'-yl]-cis-4R-methyl-5S-phenyloxazolidin-2-one

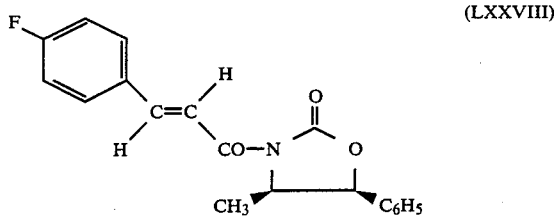

(LXXVIII)

(a) 62 ml. of 1.6M. n-butyllithium/n-hexane (6.2 g. (0.099 mole) of n-butyllithium) is added dropwise to a solution of 17.0 g. (0.096 mole) of the cis-4R-methyl-5S-phenyloxazolidin-2-one in 350 ml. of dry tetrahydrofuran stirred at −65° C. under nitrogen, and the reaction mixture is stirred under the same conditions for 15 min. to obtain a solution of Compound XXIX.

(b) A solution of 17.5 g. (0.095 mole) of crude trans-4-fluorocinnamoyl chloride (from Step 2) in 150 ml. of dry tetrahydrofuran is added dropwise to the solution of Compound XXIX from Part (a) of this step stirred at −65° C. under nitrogen, and the reaction mixture is stirred under the same conditions for an additional 2 hours. Water is added, and the obtained mixture is extracted twice with methyl t-butyl ether. The methyl t-butyl ether extracts are combined, dried over anhydrous sodium sulfate and evaporated at reduced pressure to obtain the crude solid product (31 g.) which is recrystallized from ethanol to obtain the product (22.8 g. (73%)), m.p. 105°–108° C., $[\alpha]_D = +84.789°(CHCl_3)$.

Step 4 (Reaction EE)

3-[2'α,5'α-Dimethyl-6'-(4"-fluorophenyl)cyclohex-3'-en-1'-ylcarbonyl]-cis-4R-methyl-5S-phenyloxazolidin-2-one

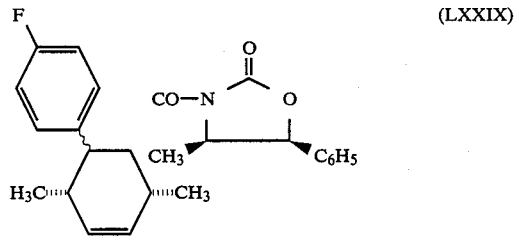

(LXXIX)

A mixture of 22.5 g. (0.069 mole) of Compound LXXVIII (from Step 3), 20 g. (0.25 mole) of E2,E4-hexadiene and 200 mg. of hydroquinone is heated at 200° C. in a steel pressure vessel for three days. The resulting reaction mixture is chromatographed on a Waters Prep-500 high pressure liquid chromatography apparatus having a silica gel column and using 10% methyl t-butyl ether/n-hexane to elute the products. The first fraction to be eluted, an oil (15.0 g.), is a 73:27 mixture of one diastereoisomer of the compound of Formula LXXIX wherein the 4-fluorophenyl group is cis to the two methyl groups and trans to the oxazolidinonecarbonyl group and one diastereoisomer of the compound of Formula LXXIX wherein the 4-fluorophenyl group is trans to the two methyl groups and to the oxazolidonecarbonyl group. The second fraction to be eluted, an oil (10.0 g.), is an about 3:1 mixture of the other diastereoisomer of the same two compounds of Formula LXXIX.

Step 5 (Reaction GG)

Benzyl 2α,5α-dimethyl-6-(4'-fluorophenyl)cyclohex-3-ene-1-thiocarboxylate

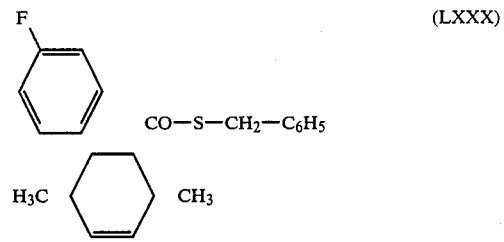

(LXXX)

37.5 ml. of 1.6M. n-butyllithium/n-hexane (4.0 g. (0.06 mole) of n-butyllithium) is added dropwise to a solution of 9.2 g. (0.074 mole) of benzyl mercaptan in 150 ml. of dry tetrahydrofuran stirred at 0° C. under nitrogen. The reaction mixture is stirred under the same conditions for an additional 10 min., a solution of 10.0 g. (0.025 mole) of the second fraction of Compound LXXIX from step 4 in 50 ml. of dry tetrahydrofuran is added dropwise, and the reaction mixture is allowed to warm to room temperature and stirred at room temperature for 18 hours, the reaction mixture being stirred under nitrogen throughout. The reaction mixture is acidified with 1N, hydrochloric acid and extracted twice with methyl t-butyl ether. The methyl t-butyl ether extracts are combined, dried over anhydrous sodium sulfate and evaporated at reduced pressure, and the residue is chromatographed on a Waters Prep-500 high pressure liquid chromatography apparatus having a silica gel column and using 30% ethyl acetate/n-hexane as the eluant to obtain, as an oil, the product contaminated with excess benzyl mercaptan (14.1 g.). The product is an about 3:1 mixture of one diastereoisomer of the compound of Formula LXXX wherein the 4-fluorophenyl group is cis to the two methyl groups and trans to the benzylthiocarbonyl group and one diastereoisomer of the compound of said formula wherein the 4-fluorophenyl group is trans to the two methyl groups and to the benzylthiocarbonyl group.

Step 6 (Reaction HH)

(+)-2α,5α-Dimethyl-6α-(4'-fluorophenyl)cyclohex-3-ene-1βS-methanol

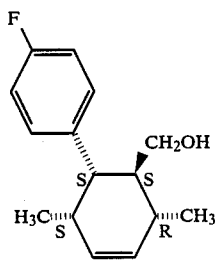
(LXVIIa)

(a) A solution of 14.0 g. of contaminated Compound LXXX (the approximately 3:1 mixture of isomers from Step 5) in 50 ml. of dry tetrahydrofuran is added dropwise to a mixture of 200 ml. of dry tetrahydrofuran and 40 ml. of a 1M. solution of lithium aluminum hydride in dry diethyl ether stirred at room temperature under nitrogen, and the reaction mixture is stirred under the same conditions for an additional 3 hours. Saturated sodium sulfate solution is carefully added until a thick precipitate forms. The solid is removed by filtration and washed well with methyl t-butyl ether. The filtrate and the washings are combined and evaporated at reduced pressure, and the residue is chromatographed on a Waters Prep-500 high pressure liquid chromatography apparatus having a silica gel column and using 30% methyl t-butyl ether/n-hexane as the eluant to obtain the product as an oil (2.5 g.). $[\alpha]_D = +117.82°$ ($CH_3OH$).

N.M.R. ($CDCl_3$): 0.75δ (3H doublet) 0.90 (1H triplet; exchangeable) 1.12 (3H doublet) 1.71 (1H multiplet) 2.24 (1H multiplet) 2.45 (1H multiplet) 3.11 (1H doublet of a doublet) 3.63 (2H multiplet) 5.5 (1H doublet) 5.70-5.80 (1H multiplet 6.93-7.18 (4H multiplet)

(b) Also eluted from the column is (+)-2α,5α-dimethyl-6β-(4'-fluorophenyl)cyclohex-3-ene-1α-methanol, an oil (0.412 g.). $[\alpha]_D = +46.74°$ ($CH_3OH$).

N.M.R. ($CDCl_3$): 0.81δ (3H doublet) 0.93 (1H triplet, exchangeable) 1.04 (3H doublet) 2.16-2.40 (3H multiplet) 2.56 (1H multiplet) 3.28 (2H multiplet) 5.56 (1H multiplet) 5.73-5.83 (1H multiplet) 6.95-7.2 (4H multiplet)

From the first fraction of Compound LXXIX from Step 4 of this example, by utilizing the processes of Step 5 and this Step, one obtains:

(c) (−)-2β,5β-Dimethyl-6β-(4'-fluorophenyl)cyclohex-3-ene-1αR-methanol, an oil (5.6 g.), $[\alpha]_D = -113.98°$ ($CH_3OH$)

N.M.R. ($CDCl_3$): 0.76δ (3H doublet) 0.92 (1H triplet, exchangeable) 1.12 (3H doublet) 1.54-1.76 (1H multiplet) 2.15-2.52 (2H multiplet) 3.1 (1H doublet of a doublet) 3.5-3.7 (2H multiplet) 5.49 (1H doublet) 5.66-5.76 (1H multiplet) 6.91-7.33 (4H multiplet)

(d) (−)-2β,5β-Dimethyl-6α-(4'-fluorophenyl)cyclohex-3-ene-1β-methanol, an oil (0.771 g.) $[\alpha]_D = -49.67°$ ($CH_3OH$)

N.M.R. ($CDCl_3$): 0.75δ (3H doublet) 1.0 (3H doublet) 1.9-2.65 (5H multiplet, 1 exchangeable) 3.25 (2H multiplet) 5.54 (1H multiplet) 5.73-5.83 (1H multiplet) 6.9-7.4 (4H multiplet)

EXAMPLE 2

(E)-3,5-Dihydroxy-7-[2'α,5'α-dimethyl-6'α-(4''-fluorophenyl)cyclohex-3'-en-1'βS-yl]hept-6-enoic acid (Reactions C and D)

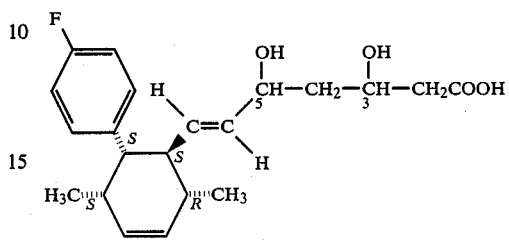
(LXXXI)

10.0 ml. of 1.0N. sodium hydroxide solution is added to a solution of 3.7 g of Compound LXIV (the mixture of four diastereoisomers from Step 12 of Example 1), and the reaction mixture is stirred at 70° C. for 4 hours. The ethanol is evaporated at reduced pressure, water is added to the residue, and the solution is washed once with diethyl ether. The solution of the sodium salt of the compound of Formula LXXXI (a mixture of four diastereoisomers, the 3R,5R, 3R,5S, 3S,5R and 3S,5S isomers) is acidified with 10.0 ml. of 1.0N. hydrochloric acid and extracted three times with methylene chloride. The methylene chloride extracts are combined, dried over anhydrous sodium sulfate and evaporated at reduced pressure to obtain the product, a mixture of four diastereoisomers (with the ratio of the erythro isomers to the threo isomers being about 8-9:1), as an oil (3.3 g. (96%)).

The obtained mixture of four diastereoisomers may be separated by conventional means, the four isomers being the 3R,5R, 3R,5S, 3S,5R and 3S,5S isomers.

EXAMPLE 3

(E)-6-[2'-(2''α,5''α-Dimethyl-6''α-(4'''-fluorophenyl)cyclohex-3''-en-1''βS-yl)ethenyl]-4-hydroxy-3,4,5,6-tetrahydro-2H-pyran-2-one (Reaction E)

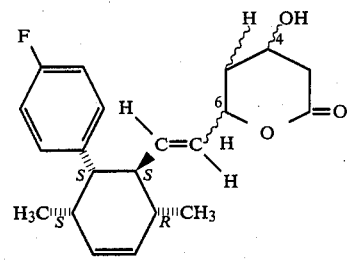
(LXXXII)

A solution of 3.3 g. of Compound LXXXI (the mixture of diastereoisomers from Example 2) in 100 ml. of benzene is refluxed for 5 hours, the water formed being removed by the use of a Dean-Stark apparatus. The solvent is evaporated at reduced pressure, and the residue is flash chromatographed on a silica gel column utilizing 5% methanol/chloroform to elute the product (a mixture of four diastereoisomers wherein the ratio of the trans isomers, i.e., the isomers wherein the hydrogen atoms in the 4- and 6-positions of the lactone ring are trans to each other, to the cis isomers is about 8-9:1, the two trans isomers being present in approximately equal amounts and the two cis isomers also being present in approximately equal amounts), a solid foam (1.8 g. (57%)). [α]$_D$=+84.59° (CHCl$_3$)

I.R. (CHCl$_3$): 3609, 3434, 1726 and 1240 cm.$^{-1}$ and others

N.M.R. (CDCl$_3$): 0.73δ (3H doublet) 1.01 (1.5H doublet) 1.05 (1.5H doublet) 1.55-2.65 (8H multiplet) 2.93-3.05 (1H multiplet) 3.93 (0.5H multiplet) 4.2 (0.5H multiplet) 4.85-5.05 (1H multiplet) 5.1-5.6 (3H multiplet) 5.7-5.8 (1H multiplet) 6.85-7.1 (4H multiplet)

Examples 3A and 3B (E)-Trans-6S-[2'-(2''α,5''α-Dimethyl-6''α-(4'''-fluorophenyl)cyclohex-3''-en-1''βS-yl)ethenyl]-4R-hydroxy-3,4,5,6-tetrahydro-2H-pyran-2-one

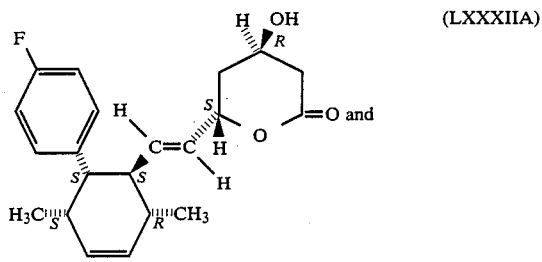

(LXXXIIA)

(E)-Trans-6R-[2'-(2''α,5''α-Dimethyl-6''α-(4'''-fluorophenyl)cyclohex-3''-en-1''βS-yl)ethenyl]-4S-hydroxy-3,4,5,6-tetrahydro-2H-pyran-2-one

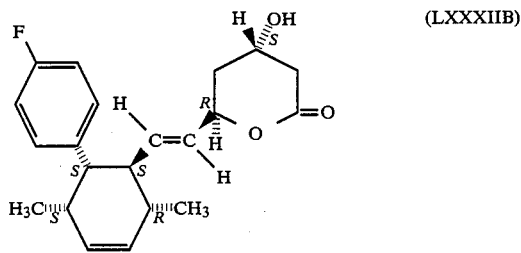

(LXXXIIB)

The mixture of isomers of Example 3 is chromatographed on a Waters Prep-500 high pressure liquid chromatography apparatus having a silica gel column and utilizing 1:1 ethyl acetate/n-hexane as the eluant.

The first major fraction eluted is the trans 4R,6S isomer (Example 3A): [α]$_D$=+104.15° (CH$_3$OH, c=0.0065) m.p. 117°-121° C.

N.M.R. (CDCl$_3$): 0.7δ (3H doublet) 1.05 (3H doublet) 1.4-1.7 (2H multiplet) 2-2.4 (4H multiplet) 2.4-2.75 (2H multiplet) 2.9-3.05 (1H doublet of a doublet) 4.2 (1H multiplet (4-position of lactone ring)) 4.9 (1H multiplet (6-position of lactone ring)) 5.1-5.6 (3H multiplet) 5.75 (1H multiplet) 6.95 (4H multiplet)

The second major fraction eluted is the trans 4S,6R isomer (Example 3B): an oil [α]$_D$=+54.63° (CH$_3$OH, c=0.0108)

N.M.R. (CDCl$_3$): 0.7 (d, 3H), 1.0 (d, 3H), 1.5-1.9 (om's, 3H) 1.9-2.6 (om's, 5H), 3.0 (dd, 1H), 3.93 (m, 1H (4-position of lactone ring)), 5.0 (m, 1H (6-position of lactone ring)), 5.1-5.6 (m, 3H), 5.75 (m, 1H), 6.95 (m, 4H)

Other fractions contain the two cis lactones, i.e., the 4R,6R and 4S,6S lactones, the other two products of the mixture of Example 3.

EXAMPLE 4

6-[2'-(2''α,5''α-Dimethyl-6''α-(4'''-fluorophenyl)cyclohex-1''βS-yl)-ethyl]-4-hydroxy-3,4,5,6-tetrahydro-2H-pyran-2-one (Reaction II)

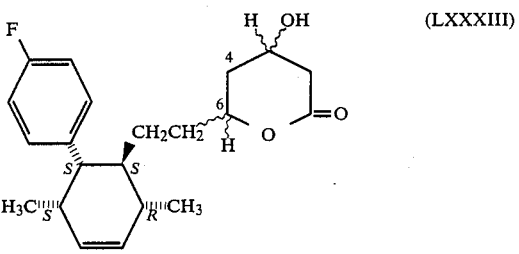

(LXXXIII)

A solution of 0.4 g. of Compound LXXXII (the mixture of four diastereoisomers from Example 3) in 3 ml. of ethyl acetate is contacted with an excess of hydrogen at an initial pressure of 20 p.s.i. in the presence of 35 mg. of platinum dioxide for 18 hours at room temperature. The catalyst is removed by filtration, and the filtrate is evaporated at reduced pressure to obtain the product, a mixture of four diastereoisomers, as an oil (0.4 g. (100%)).

N.M.R. (CDCl$_3$): 3.85δ (1H multiplet) 4.25 (1H multiplet) and others

The obtained mixture of four diastereoisomers may be separated by conventional means, the four isomers being the 4R,6R, 4R,6S, 4S,6R and 4S,6S isomers.

EXAMPLE 5

Sodium (E)-3,5-dihydroxy-7-[2'α,5'α-dimethyl-6'α-(4''-fluorophenyl)cyclohex-3'-en-1'βS-yl]hept-6-enoate (Reaction JJ)

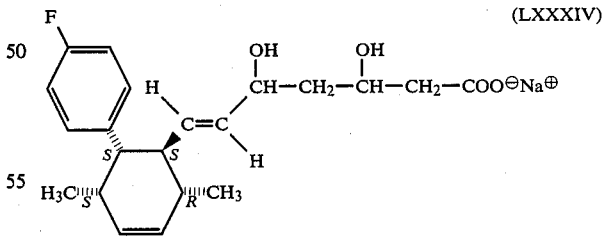

(LXXXIV)

To a solution of 0.2 g. (0.00058 mole) of Compound LXXXII (the mixture of four diastereoisomers from Example 3) in 5 ml. of ethanol is added 0.58 ml. (0.00058 mole) of 1.0N. aqueous sodium hydroxide solution, and the reaction mixture is stirred at 70° C. for 4 hours. The ethanol is evaporated at reduced pressure, and the residue is dissolved in water. The solution is washed once with diethyl ether and lyophilized to obtain the product (0.212 g. (98%)), a solid having no defined melting point and that decomposes over a temperature range in excess of 100 Centigrade degrees.

N.M.R. (D$_2$O): 0.61δ (1.5H doublet) 0.62 (1.5H doublet) 0.95 (3H doublet) 1.2–1.6 (2H multiplet) 1.95–2.4 (5H multiplet) 2.96 (2H multiplet) 3.63 (0.5H multiplet) 3.95 (0.5H multiplet) 5.0–5.83 (4H multiplet) 6.85–7.2 (4H multiplet)

The obtained mixture of four diastereoisomers may be separated by conventional means, the four isomers being the 3R,5R, 3R,5S, 3S,5R and 3S,5S isomers.

EXAMPLE 5A

Sodium (E)-3R,5S-dihydroxy-7-[2'α,5'α-dimethyl-6'α-(4"-fluorophenyl)cyclohex-3'-en-1'βS-yl]hept-6-enoate (Reaction JJ)

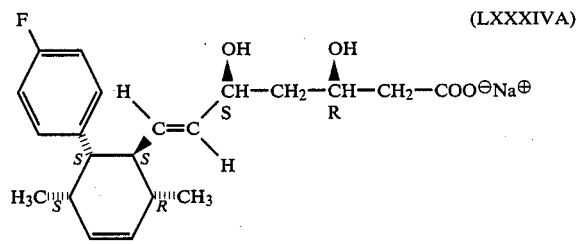

(LXXXIVA)

The product is obtained from Compound LXXXIIA (Example 3A) by the process of Example 5.

EXAMPLE 5B

Sodium (E)-3S,5R-dihydroxy-7-[2'α,5'α-dimethyl-6'α-(4"-fluorophenyl)cyclohex-3'-en-1'βS-yl]hept-6-enoate (Reaction JJ)

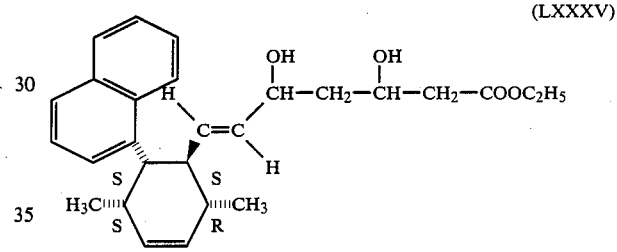

(LXXXIVB)

The product is obtained from Compound LXXXIIB (Example 3B) by the process of Example 5.

EXAMPLE 6

Ethyl (E)-3,5-dihydroxy-7-(2'α,5'α-dimethyl-6'α-naphth-2"-ylcyclohex-3'-en-1'βS-yl)hept-6-enoate

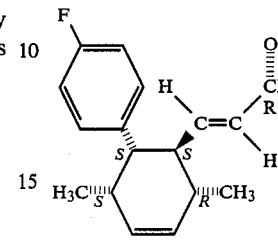

(LXXXV)

3-[(E)-3'-(2"α,5"α-Dimethyl-6"α-naphth-2"'-ylcyclohex-3"-en-1"βS-yl)-1'-oxopropenyl]-cis-4R-methyl-5S-phenyloxazolidin-2-one Steps 1–8 (Reactions Z, AA and M-Q (Steps 2–8))

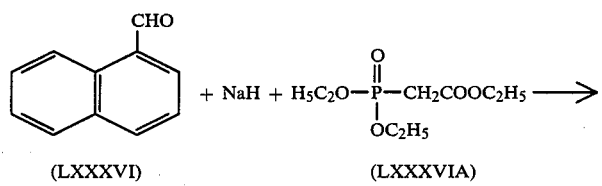

(LXXXVI)   (LXXXVIA)

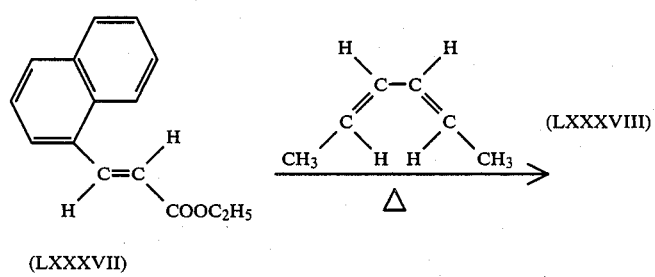

(LXXXVII)

-continued
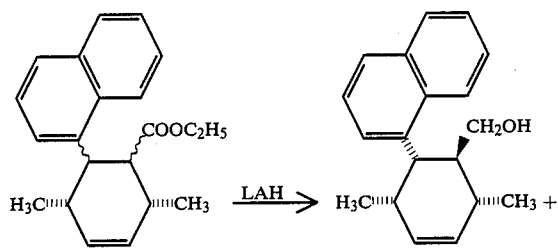
(LXXXIX) → (XC)
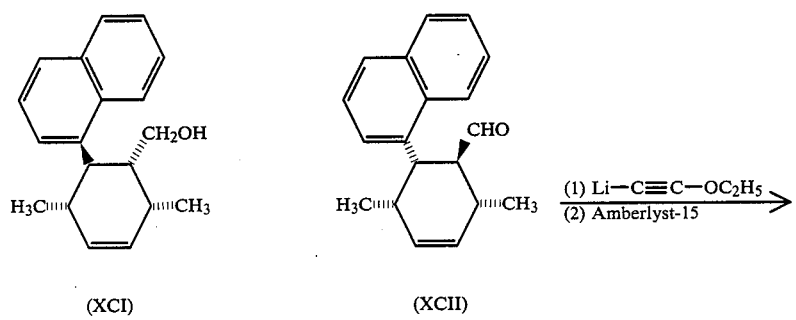
(XCI)    (XCII)
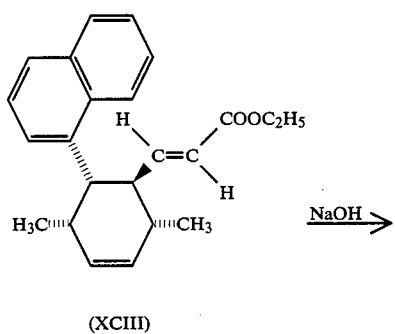
(XCIII)
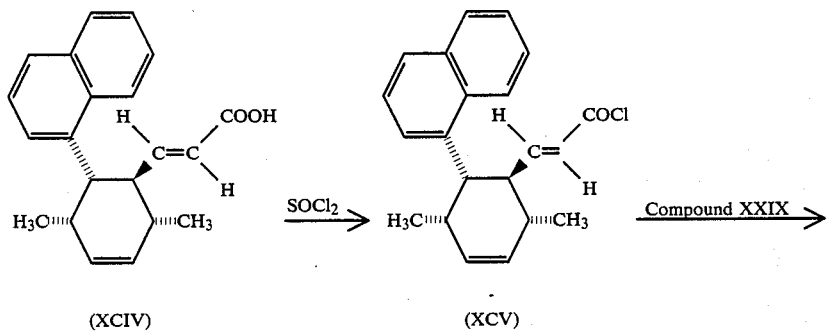
(XCIV)    (XCV)

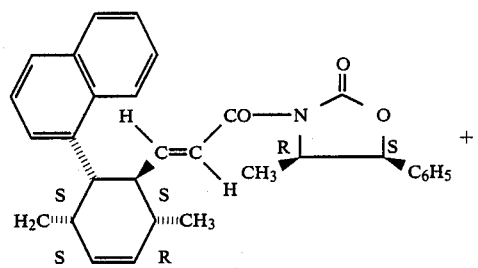

(XCVI)

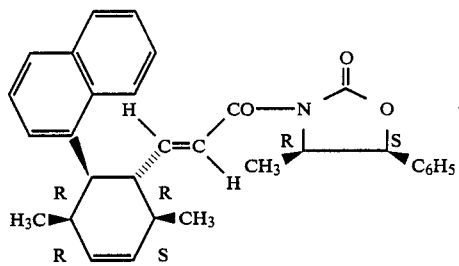

(XCVII)

Compounds XCVI and XCVII are synthesized from 1-naphthaldehyde and triethyl phosphonoacetate substantially in accordance with Steps 1-8 of Example 1 (Steps 2-8 being Reactions Z, AA and M-Q, respectively), the principal differences being that Reaction Z is run at 195° C. for 3 days, the product of Reaction N is purified on a Waters Prep-500 high pressure liquid chromatography apparatus having a silica gel column and utilizing 5% ethyl acetate/n-hexane as the eluant, Reaction O is run at 80° C. for 4½ hours and, after acidification, the product is extracted once with ethyl acetate and once with methylene chloride, Reaction P is run at 70° C. for 12 hours, and the products of Reaction Q are eluted from the Waters Prep-500 high pressure liquid chromatography apparatus having a silica gel column with 1:1 methylene chloride/n-hexane.

Compound LXXXVII—an oil

Compound LXXXIX—an oil, a mixture of two racemates in a ratio of about 70:30. In the principal racemate the 1-naphthyl group is cis to the two methyl groups and trans to the ethoxycarbonyl group and in the minor racemate it is trans to the two methyl groups and to the ethoxycarbonyl group.

Compound XC—an oil (a racemate)

Compound XCI—an oil (a racemate)} Ratio of Compound XC to Compound XCI is about 68:32

Compound XCII—m.p. 107°-109° C. (a racemate)

Compound XCIII—m.p. 89°-92° C. (a racemate)

Compound XCIV—m.p. 210°-213° C. (a racemate)

Compound XCV—an oil (a racemate)

Compound XCVI—[α]$_D$= −77.01° (CHCl₃, c=0.0064) m.p. 108°-113° C.

Compound XCVII—[α]$_D$= +42.40° (CHCl₃, c=0.0106) m.p. 96°-100° C.

Step 9 (Reaction GG')

Benzyl (E)-3-(2'α,5'α-dimethyl-6'α-naphth-1''-ylcyclohex-3'-en-1'βS-yl)thiopropenoate

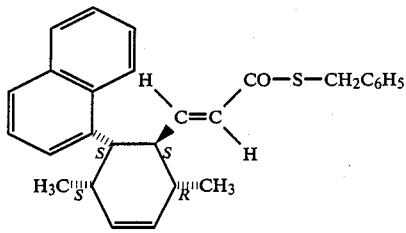

(XCVIII)

236 mg. (3.69 mmoles) of n-butyllithium (as a 1.6M. solution in n-hexane) is added dropwise to 460 mg. (3.71 mmoles) of benzylmercaptan in 30 ml. of dry tetrahydrofuran stirred at 20°-25° C. under nitrogen. The reaction mixture is stirred at 20°-25° C. for 10 minutes and cooled to −25° C., 1.55 g. (3.3 mmoles) of Compound XCVI in 25 ml. of dry tetrahydrofuran is added dropwise with stirring at −25° C., and the reaction mixture is stirred at −25° C. for an additional 30 minutes, the reaction mixture being maintained under nitrogen throughout. Water is added, and the mixture is extracted once with methyl t-butyl ether and twice with methylene chloride. The extracts are combined, dried over anhydrous sodium sulfate and evaporated at reduced pressure to an oil. The oil is dissolved in methylene chloride and chromatographed on a silica gel column utilizing methylene chloride as the first eluant and then 5% methanol/methylene chloride to elute the product. The solvent is evaporated to obtain the product as a glass (1.2 g.). [α]$_D$= −38.57° (CH₃OH, c=0.0133)

Step 10 (Reaction HH')

(E)-3-(2'α,5'α-Dimethyl-6'α-naphth-1''-ylcyclohex-3'-en-1'βS-yl)prop-2-en-1-il

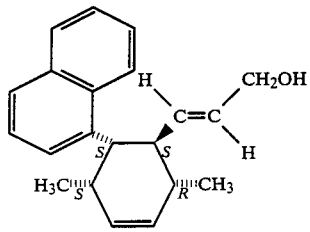

(XCIX)

The product is obtained from 1.1 g. (2.67 mmoles) of Compound XCVIII (Step 9 of this example) substantially in accordance with Step 6 of Example 1A, the principal differences being that 3.0 ml. of a 1M. solution of lithium aluminum hydride in dry tetrahydrofuran is utilized, and the crude product is flash chromatographed on a silica gel column utilizing 2:1 n-hexane/ethyl acetate as the eluant to obtain the product as an oil (746 mg.). $[α]_D = +33.71°$ ($CH_3OH$, c=0.007)

Step 11 (Reaction S)

(E)-3-(2'α,5'α-Dimethyl-6'α-naphth-1''-ylcyclohex-3'-en-1'βS-yl)prop-2-enal

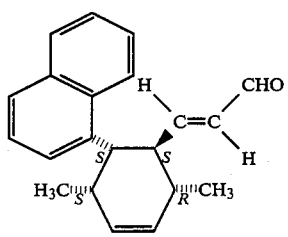

(C)

720 mg. of Compound XCIX and 4 g. of manganese dioxide are stirred in 40 ml. of methylene chloride at 20°–25° C. for 60 hours. The manganese dioxide is removed by filtration and washed with methylene chloride, and the filtrate and washings are combined and evaporated at reduced pressure to obtain the product as an oil (514 mg.) $[α]_D = -41.69°$ ($CH_3OH$, c=0.0071)

Steps 12 and 13 (Reactions A and B)

Ethyl (E)-3,5-dihydroxy-7-(2'α,5'α-dimethyl-6'α-naphth-1''-ylcyclohex-3'-en-1'βS-yl)hept-6-enoate

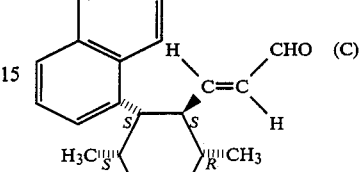

(1) $CH_3COCH_2COOC_2H_5$ + LDA
(2) Compound C

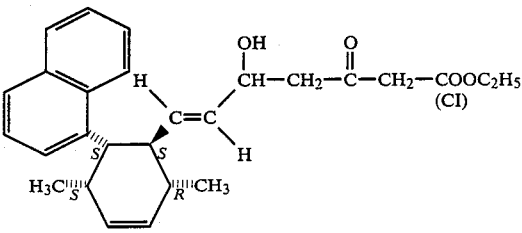
(CI)

(1) $B(C_2H_5)_3$
(2) $NaBH_4$
(3) $H_2O_2/CH_3OH$

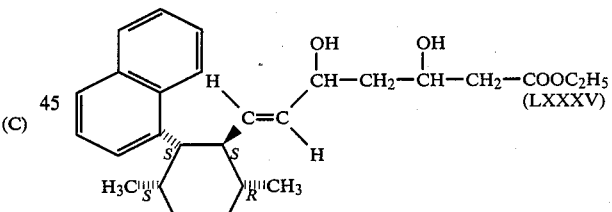
(LXXXV)

The product is obtained as a glass from Compound C substantially in accordance with Steps 11 and 12 of Example 1. It is a mixture of four diastereoisomers wherein the ratio of the erythro isomers to the threo isomers is about 6–9:1.

N.M.R. ($CDCl_3$): 0.65 (3 sets of overlapping doublets, 3H), 1.1 (3 sets of overlapping doublets, 3H), 0.9–1.7 (om's, 8H), 2–2.7 (om's, 5H), 3.85 (m, 1H), 4.15 (m, 3H), 5.1 (m, 1H), 5.65 (m, 2H), 5.8 (m, 1H), 7.15 (m, 1H), 7.4 (m, 3H), 7.65 (m, 1H), 7.8 (m, 1H), 8.05 (m, 1H)

EXAMPLE 7

(E)-3,5-Dihydroxy-7-(2'α,5'α-dimethyl-6'α-naphth-1''-ylcyclohex-3'-en-1'βS-yl)hept-6-enoic acid (Reactions C and D)

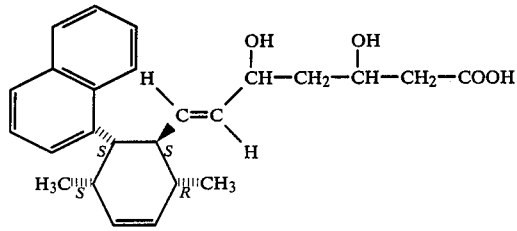
(CII)

The product is obtained from 520 mg. of Compound LXXXV (the mixture of four diastereoisomers of Example 6) and 1.25 ml. of 1N. sodium hydroxide solution substantially in accordance with Example 2, the principal difference being that Reaction C is run at 50°–60° C. The product of Reaction C is a solution of the four diastereoisomeric sodium salts of Compound CII. The product of Reaction D is a mixture of the four diastereoisomeric carboxylic acids of Formula CII. In each case, the ratio of the erythro (3R,5S and 3S,5R) isomers to the threo (3R,5R and 3S,5S) isomers is about 6–9:1.

EXAMPLE 8

(E)-6-[2'-(2''α,5''α-Dimethyl-6''α-naphth-1'''-ylcyclohex-3''-en-1''βS-yl)ethenyl]-4-hydroxy-3,4,5,6-tetrahydro-2H-pyran-2-one (Reaction E)

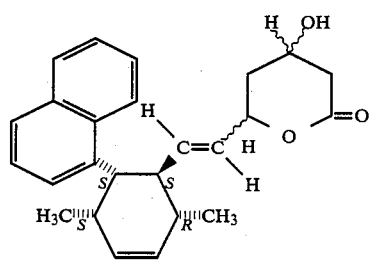
(CIII)

The product is obtained as an oil substantially in accordance with the process of Example 3, the principal difference being that the reaction time is 6 hours. It is a mixture of four diastereoisomers wherein the ratio of the trans (4R,6S and 4S,6R) isomers to the cis (4R,6R and 4S,6S) isomers is about 6–9:1. $[\alpha]_D = +11.64$ (CH$_3$OH, c=0.0055).

EXAMPLES 8A AND 8B (E)-Trans-6S-[2'-(2''α,5''α-Dimethyl-6''α-naphth-1'''-ylcyclohex-3''-en-1''βS-yl)ethenyl]-4R-hydroxy-3,4,5,6-tetrahydro-2H-pyran-2-one

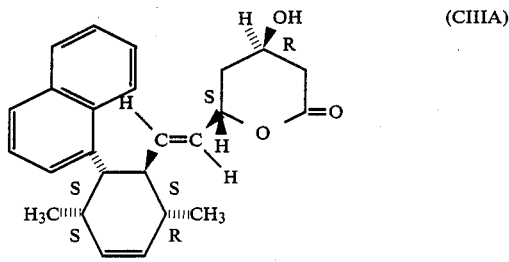
(CIIIA)

(E)-Trans-6R-[2'-(2''α,5''α-Dimethyl-6''α-naphth-1'''-ylcyclohex-3''-en-1''βS-yl)ethenyl]-4S-hydroxy-3,4,5,6-tetrahydro-2H-pyran-2-one

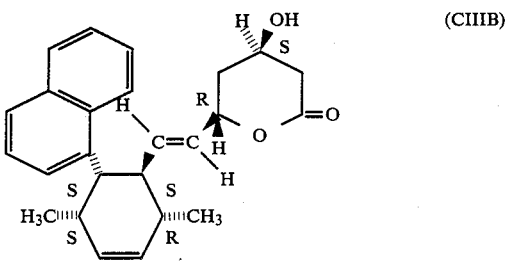
(CIIIB)

The mixture of isomers of Example 8 is chromatographed on a Waters Prep-500 high pressure liquid chromatography apparatus having a silica gel column and utilizing 1:1 ethyl acetate/n-hexane as the eluant.

The first major fraction eluted is the trans 4R,6S isomer (Example 8A): a solid foam $[\alpha]_D = +54.76°$ (CH$_3$OH, c=0.0021).

N.M.R. (CDCl$_3$): 0.65 (d, 3H), 1.1 (d, 3H), 1.35–1.8 (m, 3H), 2.1–2.3 (m, 1H), 2.35–2.7 (m, 4H), 3.87 (dd, 1H), 4.0 (m, 1H (4-position of lactone ring)), 4.85 (m, 1H (6-position of lactone ring)) and others The second major fraction is the trans 4S,6R isomer (Example 8B): an oil $[\alpha]_D = +1.35°$ (CH$_3$OH, c=0.0148)

N.M.R. (CDCl$_3$): 0.65 (d, 3H), 1.1 (d, 3H), 1.4–1.9 (m, 3H), 2.2 (m, 2H), 2.3 (d, 1H), 2.4–2.7 (m, 2H), 3.8 (m, 1H (4-position of lactone ring)), 3.9 (dd, 1H), 4.9 (m, 1H (6-position of lactone ring)), 5.2 (m, 1H), 5.4–5.7 (m, 2H), 5.8 (m, 1H), 7.15 (d, 1H), 7.45 (m, 3H), 7.7 (d, 1H), 7.8 (d, 1H), 8.1 (d, 1H)

Other fractions contain the two cis lactones, i.e., the 4R,6R and 4S,6S lactones, the other two products of the mixture of Example 8.

EXAMPLE 9

Sodium
(E)-3,5-dihydroxy-7-(2'α,5'α-dimethyl-6'α-naphth-1"-ylcyclohex-3'-en-1'βS-yl)hept-6-enoate (Reaction JJ)

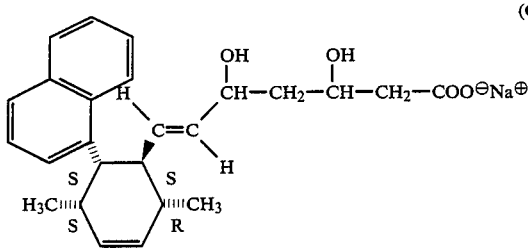
(CIV)

The product is obtained from Compound CIII (the mixture of diastereoisomers of Example 8) by the process of Example 5. It is a mixture of four diastereoisomers wherein the ratio of the erythro isomers to the threo isomers is about 6-9:1.

EXAMPLE 9A

Sodium
(E)-3R,5S-dihydroxy-7-(2'α,5'α-dimethyl-6'α-naphth-1"-ylcyclohex-3'-en-1'βS-yl)hept-6-enoate (Reaction JJ)

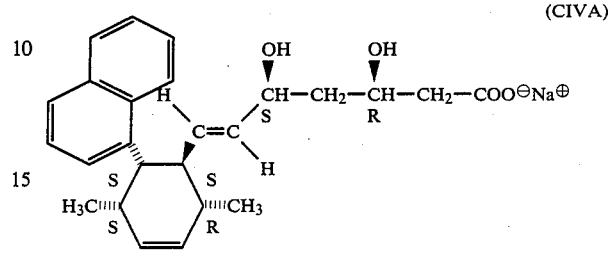
(CIVA)

The product is obtained from Compound CIIA (Example 8A) by the process of Example 5.

EXAMPLE 9B

Sodium
(E)-3S,5R-dihydroxy-7-(2'α,5'α-dimethyl-6'α-naphth-1"-ylcyclohex-3'-en-1'βS-yl)hept-6-enoate (Reaction JJ)

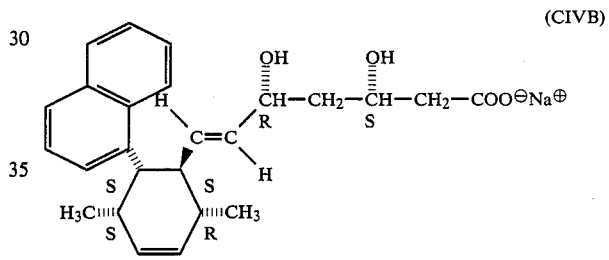
(CIVB)

The product is obtained from Compound CIIIB (Example 8B) by the process of Example 5.

EXAMPLES 10-64

The following compounds of Group IAa may be synthesized by the processes set forth above:

| Example | R₁ | R₂ | R₃ | R₄ | R₅ | R₆ R₆ₐ | R₇ | R₈ | X | R₅-Bearing Phenyl Group | m.p. | |
|---|---|---|---|---|---|---|---|---|---|---|---|---|
| 10 | H | H | H | H | H | H | H | C₂H₅ | H\β−C=C−H | α | yellow oil | Mixture of isomers with respect to the cyclohexane ring and the X-containing side chain I.R.: 3610, 3500 and 1720 cm⁻¹ and others N.M.R.: 3.8–4.2 (4H multiplet) 5.1–5.4 (2H multiplet) 5.85 (2H broad singlet) 7–7.3 (5H multiplet) and others |
| 11 | H | H | H | H | H | H | H | H | H\β−C=C−H | α | yellow oil | Mixture of isomers with respect to the cyclohexane ring and the X-containing side chain synthesized from the mixture of esters of Example 10 via Reactions C and D and from which the mixture of lactones of Example 65 is synthesized via Reaction E |
| 12 | H | H | H | H | H | H | H | Na⊕ | H\β−C=C−H | α | waxy solid | Mixture of isomers with respect to the cyclohexane ring and the X-containing side chain synthesized from the mixture of lactones of Example 65B via Reaction JJ I.R. (KBr): 3400 (broad), 1570 and 1410 cm⁻¹ and others |
| 13 | H | H | H | H | H | H | H | C₂H₅ | H\αR−C=C−H | βR | yellow oil | Mixture of isomers with respect to the X-containing side chain N.M.R.: 3.8–4.2 (4H multiplet) 5.1–5.4 (2H multiplet) 5.8 (2H broad singlet) 7–7.3 (5H multiplet) and others |
| 14 | H | H | H | H | H | H | H | H | H\αR−C=C−H | βR | yellow oil | Mixture of isomers with respect to the X-containing side chain synthesized from the mixture of esters of Example 13 via Reactions C and D and from which the mixture of lactones of Example 66 is synthesized via Reaction E |
| 15 | H | H | H | H | H | H | H | Na⊕ | H\αR−C=C−H | βR | — | Mixture of isomers with respect to the X-containing side chain synthesized from the mixture of lactones of Example 66 via Reaction JJ |
| 16 | H | H | H | H | H | H | H | C₂H₅ | H\βS−C=C−H | βS | yellow oil | Mixture of isomers with respect to the X-containing side chain I.R.: 3520, 2989, 2906, 1723, 1600 (weak) and 1216 cm⁻¹ and others N.M.R.: 3.9–4.3 (4H multiplet) 5.15–5.35 (2H multiplet) |

-continued

| Example | R$_1$ | R$_2$ | R$_3$ | R$_4$ | R$_5$ | R$_6'$/R$_{6a}$ | R$_7$ | R$_8$ | X | R$_5$-Bearing Phenyl Group | m.p. | |
|---|---|---|---|---|---|---|---|---|---|---|---|---|
| 17 | H | H | H | H | H | H | H | Na$^\oplus$ | $\overset{H}{\underset{\beta S}{\diagdown}}C=C\overset{H}{\diagup}$ | αS | — | 5.8 (2H broad singlet)<br>7–7.3 (5H multiplet) and others<br>Mixture of isomers with respect to the X-containing side chain synthesized from the mixture of esters of Example 16 via Reaction C |
| 18 | H | H | H | H | H | H | H | H | $\overset{H}{\underset{\beta S}{\diagdown}}C=C\overset{H}{\diagup}$ | αS | orange oil | Mixture of isomers with respect to the X-containing side chain synthesized from the mixture of carboxylate salts of Example 17 via Reaction D and from which a mixture of lactones is synthesized via Reaction E from which mixture the mixtures of lactones of Examples 67A and 67B are obtained (Contains some lactone)<br>I.R.: 3604, 3445, 3018, 2978, 2906, 2838, 1720, 1601, and 1239 cm.$^{-1}$ and others<br>N.M.R: 4–4.15 (2H multiplet)<br>5.1–5.4 (2H multiplet)<br>5.85 (2H broad singlet)<br>7–7.3 (5H multiplet) and others |
| 19 | H | H | H | H | 4-CH$_3$ | H | H | C$_2$H$_5$ | $\overset{H}{\underset{\beta S}{\diagdown}}C=C\overset{H}{\diagup}$ | αS | pale yellow oil | Mixture of isomers with respect to the X-containing side chain.<br>I.R.: 3604, 3495, 3007, 2907, 2841, 1723, 1610 (weak) and 1192 cm$^{-1}$ and others<br>N.M.R: 3.9–4.3 (4H multiplet)<br>5.15–5.4 (2H multiplet)<br>5.8 (2H broad singlet)<br>6.9–7.2 (4H broad singlet) and others |
| 20 | H | H | H | H | 4-CH$_3$ | H | H | Na$^\oplus$ | $\overset{H}{\underset{\beta S}{\diagdown}}C=C\overset{H}{\diagup}$ | αS | — | Mixture of isomers with respect to the X-containing side chain synthesized from the mixture of esters of Example 19 via Reaction C |
| 21 | H | H | H | H | 4-CH$_3$ | H | H | H | $\overset{H}{\underset{\beta S}{\diagdown}}C=C\overset{H}{\diagup}$ | αS | dark orange oil | Mixture of isomers with respect to the X-containing side chain synthesized from the mixture of carboxylate salts of Example 20 via Reaction D and from which a mixture of lactones is synthesized via Reaction E from which mixture the mixtures of lactones of Examples 68A and 68B are obtained. Contains some lactone.<br>I.R.: 3609, 3493, 3021, 2978, 2906, 2838, 1715, 1610, (weak), 1514, 1429 and 1195 cm.$^{-1}$ and others<br>N.M.R: 4.05–4.2 (2H multiplet)<br>5.1–5.4 (2H multiplet) |

-continued

| Example | $R_1$ | $R_2$ | $R_3$ | $R_4$ | $R_5$ | $R_{6'}$ $R_{6a}$ | $R_7$ | $R_8$ | X | $R_5$-Bearing Phenyl Group | m.p. | |
|---|---|---|---|---|---|---|---|---|---|---|---|---|
| 22 | H | H | H | H | 4-CH$_3$ | H | H | C$_2$H$_5$ | $\underset{\alpha R}{\overset{H}{\diagdown}}C=C\underset{}{\overset{H}{\diagup}}$ | $\beta R$ | orange oil | 5.8 (2H broad singlet) 6.9–7.1 (4H multiplet) and others |
| 23 | H | H | H | H | 4-CH$_3$ | H | H | Na$^\oplus$ | $\underset{\alpha R}{\overset{H}{\diagdown}}C=C\underset{}{\overset{H}{\diagup}}$ | $\beta R$ | — | Mixture of isomers with respect to the X-containing side chain N.M.R: 3.9–4.3 (4H multiplet) 5.1–5.4 (2H multiplet) 5.7 (2H broad singlet) 6.85–7.2 (4H multiplet) and others |
| 24 | H | H | H | H | 4-CH$_3$ | H | H | H | $\underset{\alpha R}{\overset{H}{\diagdown}}C=C\underset{}{\overset{H}{\diagup}}$ | $\beta R$ | yellow foam | Mixture of isomers with respect to the X-containing side chain synthesized from the mixture of esters of Example 22 via Reaction C Mixture of isomers with respect to the X-containing side chain synthesized from the mixture of carboxylate salts of Example 23 via Reaction D and from which a mixture of lactones is synthesized via Reaction E from which mixture the mixtures of lactones of Examples 69A and 69B, are obtained. Contains some lactone. I.R.: 3604, 3498, 3015, 2909, 1715, 1605 (weak), 1514, 1427, 1245 and 1185 cm.$^{-1}$ and others N.M.R.: 3.9–4.2 ($\alpha$1H multiplet) 4.6–5 (3H multiplet) 5.15–5.4 (2H multiplet) 5.7 (2H broad singlet) 6.85–7.15 (4H multiplet) and others |
| 25 | H | H | H | H | 4-CH$_3$ | H | H | Na$^\oplus$ | $\underset{\alpha R}{\overset{H}{\diagdown}}C=C\underset{}{\overset{H}{\diagup}}$ | $\beta R$ | — | Mixture of isomers with respect to the X-containing side chain synthesized from the mixture of lactones of Example 69B via Reaction JJ |
| 26 | H | H | H | H | 4-OCH$_3$ | H | H | C$_2$H$_5$ | $\underset{\beta S}{\overset{H}{\diagdown}}C=C\underset{}{\overset{H}{\diagup}}$ | $\alpha S$ | yellow oil | Mixture of isomers with respect to the X-containing side chain I.R.: 3492, 3010, 2906, 2838, 1725, 1612 (weak), 1512, 1247 and 1184 cm.$^{-1}$ and others N.M.R.: 3.75 (3H singlet) 4–4.3 (4H multiplet) 5.1–5.4 (2H multiplet) 5.8 (2H broad singlet) 6.7–6.8 (2H multiplet) 6.95–7.1 (2H multiplet) and others |

-continued

| Example | R₁ | R₂ | R₃ | R₄ | R₅ | R₆'/R₆ₐ | R₇ | R₈ | X | R₅-Bearing Phenyl Group | m.p. | |
|---|---|---|---|---|---|---|---|---|---|---|---|---|
| 27 | H | H | H | H | 4-OCH₃ | H | H | Na⊕ | H / βS C=C \ / CH₃ H | αS | — | Mixture of isomers with respect to the X-containing side chain synthesized from the mixture of esters of Example 26 via Reaction C |
| 28 | H | H | H | H | 4-OCH₃ | H | H | H | H / βS C=C \ / CH₃ H | αS | orange oil | Mixture of isomers with respect to the X-containing side chain synthesized from the mixture of carboxylate salts of Example 27 via Reaction D and from which the mixture of lactones of Example 70 is synthesized via Reaction E. Contains some lactone. I.R.: 3614, 3490, 3016, 2976, 2904, 2838, 1720, 1609, (weak), 1511, 1245 and 1184 cm.⁻¹ and others N.M.R.: 3.75 (3H singlet) 3.8–4.2 (2H multiplet) 5.15–5.4 (2H multiplet) 5.7 (2H broad singlet) 6.7–7.1 (4H multiplet) and others |
| 29 | H | H | H | H | 4-OCH₃ | H | H | C₂H₅ | H / αR C=C \ / CH₃ H | βR | yellow oil | Mixture of isomers with respect to the X-containing side chain N.M.R.: 3.3–3.6 (1H multiplet) 3.7 (3H singlet) 3.8–4.3 (4H multiplet) 5.1–5.35 (2H multiplet) 5.7 (2H multiplet) 6.6–7.1 (4H multiplet) and others |
| 30 | H | H | H | H | 4-OCH₃ | H | H | Na⊕ | H / αR C=C \ / CH₃ H | βR | — | Mixture of isomers with respect to the X-containing side chain synthesized from the mixture of esters of Example 29 via Reaction C |
| 31 | H | H | H | H | 4-OCH₃ | H | H | H | H / αR C=C \ / CH₃ H | βR | orange oil | Mixture of isomers with respect to the X-containing side chain synthesized from the mixture of carboxylate salts of Example 30 via Reaction D and from which the mixture of lactones of Example 71 is synthesized via Reaction E |
| 32 | H | H | H | H | 4-Cl | H | H | C₂H₅ | H / βS C=C \ / CH₃ H | αS | yellow oil | Mixture of isomers with respect to the X-containing side chain I.R.: 3604, 3500, 3005, 2906, 1721, 1605 (weak), 1195 and 1092 cm.⁻¹ and others NMR.: 2.9–4.3 (4H multiplet) 5.15–5.4 (2H multiplet) 5.8 (2H broad singlet) 6.9–7.3 (4H multiplet) and others |

-continued

| Example | $R_1$ | $R_2$ | $R_3$ | $R_4$ | $R_5$ | $R_{6'}$ $R_{6a}$ | $R_7$ | $R_8$ | X | $R_5$-Bearing Phenyl Group | m.p. | |
|---|---|---|---|---|---|---|---|---|---|---|---|---|
| 33 | H | H | H | H | 4-Cl | H | H | Na⊕ | 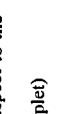 βS | αS | — | Mixture of isomers with respect to the X-containing side chain synthesized from the mixture of esters of Example 32 via Reaction C |
| 34 | H | H | H | H | 4-Cl | H | H | H | 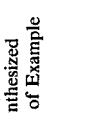 βS | αS | dark oil | Mixture of isomers with respect to the X-containing side chain synthesized from the mixture of carboxylate salts of Example 33 via Reaction D and from which a mixture of lactones is synthesized via Reaction E from which mixture the mixtures of lactones of Examples 72A and 72B are obtained |
| 35 | H | H | H | H | 4-Cl | H | H | $C_2H_5$ | 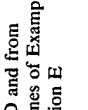 αR | βR | yellow oil | Mixture of isomers with respect to the X-containing side chain N.M.R.: 3.9–4.3 (4H multiplet) 5.1–5.4 (2H multiplet) 5.7 (2H broad singlet) 6.9–7.3 (4H multiplet) and others |
| 36 | H | H | H | H | 4-Cl | H | H | Na⊕ | αR | βR | — | Mixture of isomers with respect to the X-containing side chain synthesized from the mixture of esters of Example 35 via Reaction C |
| 37 | H | H | H | H | 4-Cl | H | H | H | αR | βR | orange oil | Mixture of isomers with respect to the X-containing side chain synthesized from the mixture of carboxylate salts of Example 36 via Reaction D and from which the mixture of lactones of Example 73 is synthesized via Reaction E |
| 38 | βS—$CH_3$ | H | H | βR—$CH_3$ | 4-F | H | H | $C_2H_5$ | 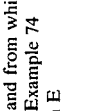 αR | βR | yellow oil | Mixture of isomers with respect to the X-containing side chain N.M.R.: 2.9–3.05 (1H multiplet) 4.05–4.25 (4H multiplet) 4.95–5.55 (3H multiplet) 5.65–5.8 (1H multiplet) 6.8–7.05 (4H multiplet) and others |
| 39 | βS—$CH_3$ | H | H | ↑R—$CH_3$ | 4-F | H | H | H |  αR | βR | orange oil | Mixture of isomers with respect to the X-containing side chain synthesized from the mixture of esters of Example 38 via Reactions C and D and from which the mixture of lactones of Example 74 is synthesized via Reaction E |

-continued

| Example | $R_1$ | $R_2$ | $R_3$ | $R_4$ | $R_5$ | $R_6'$ $R_{6a}$ | $R_7$ | $R_8$ | X | $R_5$-Bearing Phenyl Group | m.p. | |
|---|---|---|---|---|---|---|---|---|---|---|---|---|
| 40 | βS—CH$_3$ | H | H | βR—CH$_3$ | 4-F | H | H | Na⊕ |  αR H C=C H | βR | — | Mixture of isomers with respect to the X-containing side chain synthesized from the mixture of lactones of Example 74 via Reaction JJ |
| 41 | βS—CH$_3$ | H | H | βR—CH$_3$ | 4-F | H | H | Na⊕ |  αR H C=C H | βR | — | The carboxylate salt obtained from the lactone of Example 74A via Reaction JJ (3S,4R isomer) |
| 42 | βS—CH$_3$ | H | H | βR—CH$_3$ | 4-F | H | H | Na⊕ |  αR H C=C H | βR | — | The carboxylate salt obtained from the lactone of Example 74B via Reaction JJ (3R,5S isomer) |
| 43 | α—CH$_3$ | H | H | α—CH$_3$ | 4-F | H | H | C$_2$H$_5$ |  α H C=C H | β | yellow oil | Mixture of isomers with respect to the X-containing side chain N.M.R.: 4.0–4.3 (4H multiplet) 5.1–5.6 (3H multiplet) 5.65–5.8 (1H multiplet) 6.8–7.1 (4H multiplet) and others |
| 44 | α—CH$_3$ | H | H | α—CH$_3$ | 4-F | H | H | Na⊕ |  α H C=C H | β | — | Mixture of isomers with respect to the X-containing side chain synthesized from the mixture of esters of Example 43 via Reaction C |
| 45 | α—CH$_3$ | H | H | α—CH$_3$ | 4-F | H | H | H |  α H C=C H | β | yellow foam | Mixture of isomers with respect to the X-containing side chain synthesized from the mixture of carboxylate salts of Example 44 via Reaction D and from which the mixture of lactones of Example 75 is synthesized via Reaction E |
| 46 | α—CH$_3$ | H | H | α—CH$_3$ | 4-F | H | H | C$_2$H$_5$ |  α H C=C H | β | yellow oil | Mixture of isomers with respect to the X-containing side chain N.M.R.: 4.0–4.3 (4H multiplet) 5.1–5.6 (3H multiplet) 5.65–5.8 (1H multiplet) 6.8–7.1 (4H multiplet) and others |
| 47 | α—CH$_3$ | H | H | α—CH$_3$ | 4-F | H | H | Na⊕ |  α H C=C H | β | — | Mixture of isomers with respect to the X-containing side chain synthesized from the mixture of esters of Example 46 via Reaction C |

-continued

| Example | $R_1$ | $R_2$ | $R_3$ | $R_4$ | $R_5$ | $R_{6'}$ $R_{6a}$ | $R_7$ | $R_8$ | X | $R_5$-Bearing Phenyl Group | m.p. | |
|---|---|---|---|---|---|---|---|---|---|---|---|---|
| 48 | α—CH$_3$ | H | H | α—CH$_3$ | 4-F | H | H | H | $\overset{H}{\underset{\alpha}{\diagup}}C=C\overset{\diagdown}{\underset{\diagup}{H}}$ | β | orange oil | Mixture of isomers with respect to the X-containing side chain synthesized from the mixture of carboxylate salts of Example 47 via Reaction D and from which the mixture of lactones of Example 76 is synthesized via Reaction E |
| 49 | αR—CH$_3$ | CH$_3$ | CH$_3$ | αS—CH$_3$ | 4-F | H | H | C$_2$H$_5$ | $\overset{H}{\underset{\beta S}{\diagup}}C=C\overset{\diagdown}{\underset{\diagup}{H}}$ | αS | — | Mixture of isomers with respect to the X-containing side chain |
| 49A | αR—CH$_3$ | CH$_3$ | CH$_3$ | αS—CH$_3$ | 4-F | H | H | Na$^\oplus$ | $\overset{H}{\underset{\beta S}{\diagup}}C=C\overset{\diagdown}{\underset{\diagup}{H}}$ | αS | — | Mixture of isomers with respect to the X-containing side chain |
| 50 | αR—i—C$_3$H$_7$ | H | H | αS—i—C$_3$H$_7$ | 4-F | H | H | C$_2$H$_5$ | $\overset{H}{\underset{\beta S}{\diagup}}C=C\overset{\diagdown}{\underset{\diagup}{H}}$ | αS | — | Mixture of isomers with respect to the X-containing side chain |
| 50A | αR—i—C$_3$H$_7$ | H | H | αS—i—C$_3$H$_7$ | 4-F | H | H | Na$^\oplus$ | $\overset{H}{\underset{\beta S}{\diagup}}C=C\overset{\diagdown}{\underset{\diagup}{H}}$ | αS | — | Mixture of isomers with respect to the X-containing side chain |
| 51 | αR—CH$_3$ | H | H | αS—CH$_3$ | H | H | H | C$_2$H$_5$ | $\overset{H}{\underset{\beta S}{\diagup}}C=C\overset{\diagdown}{\underset{\diagup}{H}}$ | αS | oil | Mixture of isomers with respect to the X-containing side chain wherein the ratio of erythro to threo isomers is about 6-9:1 |
| 52 | αR—CH$_3$ | H | H | αS—CH$_3$ | H | H | H | H | $\overset{H}{\underset{\beta S}{\diagup}}C=C\overset{\diagdown}{\underset{\diagup}{H}}$ | αS | oil | Mixture of isomers with respect to the X-containing side chain wherein the ratio of erythro to threo isomers is about 6-9:1 synthesized from the mixture of esters of Example 51 via Reactions C and D and from which the mixture of lactones of Example 79 is synthesized via Reaction E |
| 53 | αR—CH$_3$ | H | H | αS—CH$_3$ | H | H | H | Na$^\oplus$ | $\overset{H}{\underset{\beta S}{\diagup}}C=C\overset{\diagdown}{\underset{\diagup}{H}}$ | αS | — | An about 1:1 mixture of the two erythro (3R,5S and 3S,5R) isomers synthesized from the mixture of lactones of Example 79 via Reaction JJ |

-continued

| Example | R$_1$ | R$_2$ | R$_3$ | R$_4$ | R$_5$ | R$_6'$ R$_{6a}$ | R$_7$ | R$_8$ | X | R$_5$-Bearing Phenyl Group | m.p. | |
|---|---|---|---|---|---|---|---|---|---|---|---|---|
| 54 | H | H | H | H | 4-F | H | H | C$_2$H$_5$ | $\beta$S, H, C=C, H, H (trans-CH=CH) | $\alpha$S | oil | Mixture of isomers with respect to the X-containing side chain wherein the ratio of erythro to threo isomers is about 6-9:1 |
| 55 | H | H | H | H | 4-F | H | H | H | $\beta$S, H, C=C, H, H | $\alpha$S | — | Mixture of isomers with respect to the X-containing side chain wherein the ratio of erythro to threo isomers is about 6-9:1 synthesized from the mixture of esters of Example 54 via Reactions C and D and from which the mixture of lactones of Example 80 is synthesized via Reaction E |
| 56 | H | H | H | H | 4-F | H | H | Na⊕ | $\beta$S, H, C=C, H, H | $\alpha$S | — | Mixture of isomers with respect to the X-containing side chain wherein the ratio of erythro to threo isomers is about 6-9:1 and synthesized from the mixture of lactones of Example 80 via Reaction JJ |
| 57 | $\alpha$R—CH$_3$ | H | H | $\alpha$S—CH$_3$ | | naphth-2-yl | H | C$_2$H$_5$ | $\beta$S, H, C=C, H, H | $\alpha$S | oil | Mixture of isomers with respect to the X-containing side chain wherein the ratio of erythro to threo isomers is about 6-9:1 N.M.R.: 0.75$\delta$(3H overlapping doublets) 1.05 (3H overlapping doublets) 4.1 (3H multiplet) 5.1 (1H multiplet) and others |
| 58 | $\alpha$R—CH$_3$ | H | H | $\alpha$S—CH$_3$ | | naphth-2-yl | H | H | $\beta$S, H, C=C, H, H | $\alpha$S | — | Mixture of isomers with respect to the X-containing side chain wherein the ratio of erythro to threo isomers is about 6-9:1 synthesized from the mixture of esters of Example 57 via Reactions C and D and from which the mixture of lactones of Example 81 is synthesized via Reaction E |
| 59 | $\alpha$R—CH$_3$ | H | H | $\alpha$S—CH$_3$ | | naphth-2-yl | H | Na⊕ | $\beta$S, H, C=C, H, H | $\alpha$S | — | Mixture of isomers with respect to the X-containing side chain wherein the ratio of erythro to threo isomers is about 6-9:1 and synthesized from the mixture of lactones of Example 81 via Reaction JJ |
| 60 | $\beta$S—CH$_3$ | H | H | $\beta$R—CH$_3$ | | naphth-1-yl | H | C$_2$H$_5$ | $\alpha$, H, C=C, H, H | $\beta$R | oil | Mixture of isomers with respect to the X-containing side chain wherein the ratio of erythro to threo isomers is about 6-9:1 |

-continued

| Example | R₁ | R₂ | R₃ | R₄ | R₅ | R₆'<br>R₆ₐ | R₇ | R₈ | X | R₅-Bearing<br>Phenyl Group | m.p. | |
|---|---|---|---|---|---|---|---|---|---|---|---|---|
| 61 | βS—CH₃ | H | H | βR—CH₃ | naphth-1-yl | | H | H | H\αR C=C /H (βR) | βR | — | Mixture of isomers with respect to the X-containing side chain wherein the ratio of erythro to threo isomers is about 6-9:1 synthesized from the mixture of esters of Example 60 via Reactions C and D and from which the mixture of lactones of Example 82 is synthesized via Reaction E |
| 62 | βS—CH₃ | H | H | βR—CH₃ | naphth-1-yl | | H | Na⊕ | H\αR C=C /H | βR | — | Mixture of isomers with respect to the X-containing side chain wherein the ratio of erythro to threo isomers is about 6-9:1 and synthesized from the mixture of lactones of Example 82 via Reaction JJ |
| 63 | βS—CH₃ | H | H | βR—CH₃ | naphth-1-yl | | H | Na⊕ | H\α C=C /H | βR | — | The 3R,5S erythro enantiomer containing 10-15% of the threo enantiomers synthesized from Example 82A via Reaction JJ |
| 64 | βS—CH₃ | H | H | βR—CH₃ | naphth-1-yl | | H | Na⊕ | H\αR C=C /H | βR | — | The 3S,5R erythro enantiomer synthesized from Example 82B via Reaction JJ |

EXAMPLES 65–82B

The following compounds of Group IAb may be synthesized by the processes set forth above:

The following compounds of Group IAb may be synthesized by the processes set forth above:

| Example | R₁ | R₂ | R₃ | R₄ | R₅ | R₆, R₆ₐ | R₇ | X | R₅-Bearing Phenyl Group | m.p. | Notes |
|---|---|---|---|---|---|---|---|---|---|---|---|
| 65 | H | H | H | H | H | H | H | $\underset{\beta}{H}\!\!>\!\!C\!=\!C\!<\!\underset{}{\overset{}{H}}$ (CH₃, CH₃) | α | oil | A mixture of a large number of isomers with respect to both the cyclohexene ring and the lactone ring, including cis and trans lactones. The C-4 and C-6 proton N.M.R. peaks are in the following ratio:<br>3.6δ  0.55<br>4.1δ  1.36<br>4.25δ  0.23  } all multiplet<br>4.4δ  0.64<br>4.6δ  0.18<br>4.9δ  1.00<br>Example 65 is synthesized from a mixture of compounds of Formula VI wherein the R₅-bearing phenyl group and the -X- radical are trans to each other by a non-stereoselective Reaction B. |
| 65A | H | H | H | H | H | H | H | $\underset{\beta}{H}\!\!>\!\!C\!=\!C\!<\!\underset{}{\overset{}{H}}$ | α | oil | A mixture of isomers, nearly pure trans lactones<br>C-4 = 4.15δ (1H multiplet)<br>C-6 = 4.85δ (1H quartet) |
| 65B | H | H | H | H | H | H | H | $\underset{\beta}{H}\!\!>\!\!C\!=\!C\!<\!\underset{}{\overset{}{H}}$ | α | 79°–85° C. | A mixture of isomers, including cis and trans lactones in an about 1:1 ratio<br>C-4 = 3.5δ (~0.5H multiplet) trans lactone<br>4.1δ (~0.5H multiplet) cis lactone<br>C-6 = 4.4δ (~0.5H multiplet) cis lactone<br>4.9δ (~0.5H multiplet) trans lactone |
| 65C | H | H | H | H | H | H | H | $\underset{\beta}{H}\!\!>\!\!C\!=\!C\!<\!\underset{}{\overset{}{H}}$ | α | oil | A mixture of isomers, mostly cis lactones<br>C-4 = 4.15δ (multiplet)<br>C-6 = 4.45 (multiplet)<br>Examples 65A-C are obtained by an incomplete separation of the mixture of Example 65 utilizing a Waters Prep-500 high pressure (performance) liquid chromatography apparatus having a silica gel column and 3:2 methyl t-butyl ether/n-hexane as the eluant. |
| 66 | H | H | H | H | H | H | H | $\underset{\alpha R}{H}\!\!>\!\!C\!=\!C\!<\!\underset{}{\overset{}{H}}$ | βR | oil | An about 1:1 mixture of two diastereoisomeric trans lactones<br>C-4 = 3.5–3.65δ (~0.5H multiplet) one trans lactone<br>C-4 = 4.05–4.2δ (~0.5H multiplet) other trans lactone<br>C-6 = 4.8–5δ (1H multiplet) both |

-continued

| Example | R$_1$ | R$_2$ | R$_3$ | R$_4$ | R$_5$ | R$_6$, R$_{6a}$ | R$_7$ | X | R$_5$-Bearing Phenyl Group | m.p. | |
|---|---|---|---|---|---|---|---|---|---|---|---|
| | | | | | | | | | | | trans lactones Example 66 is synthesized from an alcohol of Formula XLIV whose $[\alpha]_D = -60.15°$ (CH$_3$OH), an aldehyde of Formula XXIV whose $[\alpha]_D = -58.91°$ (CH$_3$OH) and an aldehyde of Formula XXXII whose $[\alpha]_D = -47.61°$ (CH$_3$OH). |
| 67A | H | H | H | H | H | H | H | $\beta S$ $\overset{H}{\underset{}{\diagdown}}$C=C$\overset{H}{\underset{}{\diagup}}$ $\alpha S$ | | 65°–90° C. waxy solid | An about 3:1 mixture of two diastereoisomeric trans lactones C-4 = 3.5δ (~0.25H multiplet) minor trans lactone C-4 = 4.1δ (~0.75H multiplet) major trans lactone C-6 = 4.8–5δ (1H multiplet) both trans lactones |
| 67B | H | H | H | H | H | H | H | $\beta S$ $\overset{H}{\underset{}{\diagdown}}$C=C$\overset{H}{\underset{}{\diagup}}$ $\alpha S$ | | 68°–110° C. waxy solid | An about 1:3 mixture of the two diastereoisomeric trans lactones of Example 67A C-4 = 3.45δ (~0.75H multiplet) major trans lactone C-4 = 4.1δ 4.1δ (~0.25H multiplet) minor C-6 = 4.8–4.95δ (1H multiplet) both trans lactones Examples 67A and 67B are obtained by an incomplete separation of the two diastereoisomeric trans lactones that are synthesized from an alcohol of Formula XLIV whose $[\alpha]_D = +66.8°$ (CH$_3$OH) by means of medium pressure (~5 p.s.i.) liquid chromatography utilizing a silica gel column and 9:1 methyl t-butyl ether/n-hexane as the eluant. |
| 68A | H | H | H | H | 4-CH$_3$ | H | H | $\beta S$ $\overset{H}{\underset{}{\diagdown}}$C=C$\overset{H}{\underset{}{\diagup}}$ $\alpha S$ | | 117°–139° C. waxy solid | An about 2:1 mixture of two trans lactones C-4 = 3.6δ (~0.35H multiplet) minor trans lactone C-4 = 4.1δ (~0.65H multiplet) major trans lactone C-6 = 4.85δ (1H multiplet) both trans lactones |
| 68B | H | H | H | H | 4-CH$_3$ | H | H | $\beta S$ $\overset{H}{\underset{}{\diagdown}}$C=C$\overset{H}{\underset{}{\diagup}}$ $\alpha S$ | | 100°–127° C. waxy solid | An about 1:3.5 mixture of the two trans lactones of Example 68A C-4 = 3.6δ (~0.82H multiplet) major trans lactone |

-continued

| Example | R₁ | R₂ | R₃ | R₄ | R₅ | R₆, R₆ₐ | R₇ | X | R₅-Bearing Phenyl Group | m.p. | |
|---|---|---|---|---|---|---|---|---|---|---|---|
| | | | | | | | | | | | C-4 = 4.15δ (~0.18H multiplet) minor trans lactone<br>C-6 = 4.96 (1H multiplet) both trans lactones Examples 68A and 68B are obtained by an in-complete separation of the two trans lactones synthesized from an alcohol of Formula XLIV whose [α]$_D$ = +68.0° (CH₃OH) and an aldehyde of Formula XXXII whose [α]$_D$ = +56.3° (CH₃OH) by means of medium pressure (~5 p.s.i.) liquid chromatography utilizing a silica gel column and 9:1 methyl t-butyl ether/n-hexane as the eluant. |
| 69A | H | H | H | H | 4-CH₃ | H | H | 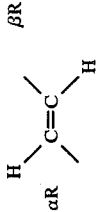 | βR | 104°–115° C. | An about 5:1 mixture of two trans lactones [α]$_D$ = −61.7δ° (CH₃OH)<br>C-4 = 3.6δ (~0.17H multiplet) minor trans lactone<br>C-4 = 4.15δ (~0.83H multiplet) major trans lactone C-6 = 4.85δ (1H multiplet) both trans lactones CH₃(R₅) = 2.3δ (3H singlet) |
| 69B | H | H | H | H | 4-CH₃ | H | H | 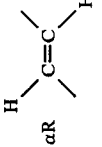 | βR | 106–116° C. | An about 1:4 mixture of the two trans lactones of Example 69A [α]$_D$ = −87.77° (CH₃OH)<br>C-4 = 3.6δ(~0.8H multiplet) major trans lactone<br>C-4 = 4.15δ(~0.2H multiplet) minor trans lactone<br>C-6 = 4.95δ (1H multiplet) both trans lactones CH₃(R₅) = 2.3δ(3H singlet) Examples 69A and 69B are obtained by an incomplete separation of the two trans lactones synthesized from an aldehyde of Formula XXIV whose [α]$_D$ = −39.86° (CH₃OH) and an aldehyde of Formula XXXII whose [α]$_D$ = 57° (CH₃OH) by means of medium pressure (~5 p.s.i.) liquid chromatography utilizing a silica gel column and 9:1 methyl t-butyl ether/n-hexane as the eluant. |

-continued

| Example | R$_1$ | R$_2$ | R$_3$ | R$_4$ | R$_5$ | R$_6$, R$_{6a}$ | R$_7$ | X | R$_5$-Bearing Phenyl Group | m.p. | |
|---|---|---|---|---|---|---|---|---|---|---|---|
| 70 | H | H | H | H | 4-OCH$_3$ | H | H |  | αS | 75°–95° C. waxy solid | An about 1:1 mixture of two trans lactones [α]$_D$ = +65.21° (CH$_3$OH) C-4 = 3.45δ (∼0.5H multiplet) one trans lactone C-4 = 4.1δ (∼0.5H multiplet) other trans lactone C-6 = 4.9δ (1H multiplet) both trans lactones OCH$_3$(R$_5$) = 3.75δ (3H singlet) Example 70 is synthesized from an alcohol of Formula XLIV whose [α]$_D$ = +65.21° (CH$_3$OH) and an aldehyde of Formula XXXII whose [α]$_D$ = +59.95° (CH$_3$OH) |
| 71 | H | H | H | H | 4-OCH$_3$ | H | H | 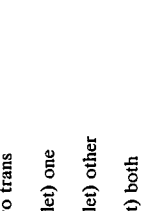 | βR | oil | [α]$_D$ = −47.04° (CH$_3$OH) An about 1:1 mixture of two trans lactones C-4 = 3.5δ (∼0.5H multiplet) one trans lactone C-4 = 4.1δ (∼0.5H multiplet) other trans lactone C-6 = 4.8–5δ (1H multiplet) both trans lactones Example 71 is synthesized from an alcohol of Formula XLIV whose [α]$_D$ = −62.16° (CH$_3$OH) and an aldehyde of Formula XXIV whose [α]$_D$ = −59.37° (CH$_3$OH) |
| 72A | H | H | H | H | 4-Cl | H | H | 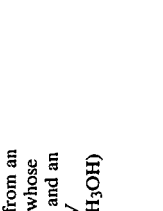 | αS | 135°–147° C. | An about 2.5:1 mixture of two trans lactones C-4 = 3.65δ (∼0.29H multiplet) minor trans lactone C-4 = 4.2δ (∼0.71H multiplet) major trans lactone C-6 = 4.85δ (1H multiplet) both trans lactones |
| 72B | H | H | H | H | 4-Cl | H | H |  | αS | 115°–130° C. | An about 1:3.5 mixture of the two trans lactones of Example 72A C-4 = 3.65δ (∼0.78H multiplet) major trans lactone C-4 = 4.2δ(∼0.22H multiplet) minor trans lactone C-6 = 4.9δ (1H multiplet) both trans lactones Examples 72A and 72B are obtained by an incomplete separation of the two trans lactones synthesized from an alcohol of |

4,876,280

-continued

| Example | R₁ | R₂ | R₃ | R₄ | R₅ | R₆, R₆ₐ | R₇ | X | R₅-Bearing Phenyl Group | m.p. | |
|---|---|---|---|---|---|---|---|---|---|---|---|
| | | | | | | | | | | | Formula XXIII whose $[\alpha]_D = +62.38°$ (CH₃OH) by means of medium pressure (~5 p.s.i.) liquid chromatography using a silica gel column and 9:1 methyl t-butyl ether/n-hexane as the eluant. |
| 73 | H | H | H | H | 4-Cl | H | H | H\C=C/H (αR) (βR) / CH₃ | | 135°–137° C. | An about 1:1 mixture of two trans lactones $[\alpha]_D = -72.03°$ (CH₃OH) C-4 = 3.7δ (~0.5H multiplet) one trans lactone C-4 = 4.26 (~0.5H multiplet) other trans lactone C-6 = 4.85–5.18 (1H multiplet) both trans lactones Example 73 is synthesized from an alcohol of Formula XXIII whose $[\alpha]_D = -60.45°$ (CH₃OH), an aldehyde of Formula XXIV whose $[\alpha]_D = -64.75°$ (CH₃OH) and an aldehyde of Formula XXXII whose $[\alpha]_D = -41.75°$ (CH₃OH). |
| 74 | βS—CH₃ | H | H | βR—CH₃ | 4-F | H | H | H\C=C/H (αR) (βR) / CH₃ | | glassy solid-no discrete m.p. | $[\alpha]_D = 78.25°$ (CHCl₃) A mixture of four diastereoisomers wherein the ratio of the two trans lactones to the two cis lactones is about 8-9:1 with the ratio of one trans lactone to the other being about 1:1 and the ratio of one cis lactone to the other being about 1:1 C-4 = 3.9δ (~0.5H multiplet) C-4 = 4.18δ (~0.5H multiplet) C-6 = 4.95δ (1H multiplet) Example 74 is synthesized from an alcohol of Formula XLIV whose $[\alpha]_D = -113.98°$ (CH₃OH) (i.e., the alcohol of Example 1A, Step 6, part (c) and an oxazolidinone of Formula XXX whose $[\alpha]_D = -22.4°$ (CHCl₃). |
| 74A | βS—CH₃ | H | H | βR—CH₃ | 4-F | H | H | H\C=C/H (αR) (βR) / CH₃ | | glassy solid-no discrete m.p. | One of the trans lactones of Example 74-4S,6R isomer $[\alpha]_D = -105.49°$ (CHCl₃) |

-continued

| Example | R₁ | R₂ | R₃ | R₄ | R₅ | R₆, R₆ₐ | R₇ | X | R₅-Bearing Phenyl Group | m.p. | |
|---|---|---|---|---|---|---|---|---|---|---|---|
| 74B | βS—CH₃ | H | H | βR—CH₃ | 4-F | H | H | H\\_C=C_/H  αR / \\ | βR | foam-no discrete m.p. | The other translactone of Example 74-4R,6S isomer [α]_D = −64.91° (CHCl₃) The trans lactones of Examples 74,A and 74B are obtained from the mixture of Example 74 by means of high pressure liquid chromatography utilizing a Waters Prep-500 apparatus having a silica gel column and 1:1 n-hexane/ethyl acetate as the eluant. |
| 75 | α-CH₃ | H | H | α-CH₃ | 4-F | H | H | H\\_C=C_/H  α / \\ | β | gummy solid no discrete m.p. | An about 1:1 mixture of two diastereoisomeric trans lactones C-4 = 3.65δ (~0.5H multiplet) one trans lactone C-4 = 4.15δ (~0.5H multiplet) other trans lactone C-6 = 4.9δ (1H multiplet) both trans lactones Example 75 is synthesized from an oxazolidinone of Formula XXX whose [α]_D = +7.45 (CHCl₃) |
| 76 | α-CH₃ | H | H | α-CH₃ | 4-F | H | H | H\\_C=C_/H  α / \\ | β | oil | An about 1:1 mixture of two diastereoisomeric trans lactones C-4 = 3.65δ (~0.5H multiplet) other trans lactone C-6 = 4.9δ (1H multiplet) both trans lactones Example 76 is synthesized from an oxazolidinone of Formula XXX whose [α]_D = +19.62° (CHCl₃). |
| 77 | αR—CH₃ | CH₃ | CH₃ | αS—CH₃ | 4-F | H | H | H\\_C=C_/H  βS / \\ | αS | — | Mixture of four diastereoisomeric cis and trans lactones |
| 78 | αR—i-C₃H₇ | H | H | αS—i-C₃H₇ | 4-F | H | H | H\\_C=C_/H  βS / \\ | αS | — | Mixture of four diastereoisomeric cis and trans lactones |
| 79 | αR—CH₃ | H | H | αS—CH₃ | H | H | H | H\\_C=C_/H  βS / \\ | αS | oil | An about 1:1 mixture of the two diastereoisomeric trans lactones [α]_D = +64.3° (CHCl₃), c = 0.00535 C-4 = 3.6δ (~0.5H multiplet) one trans lactone trans lactone (~0.5H multiplet) other |

-continued

| Example | R₁ | R₂ | R₃ | R₄ | R₅ | R₆, R₆ₐ | R₇ | X | R₅-Bearing Phenyl Group | m.p. | |
|---|---|---|---|---|---|---|---|---|---|---|---|
| | | | | | | | | | | | C-6 = 4.96 (1H multiplet) both trans lactones Example 79 is synthesized from an alcohol of Formula XXIII whose [α]_D = +125.9° (CH₃OH), an aldehyd of Formula XXIV whose [α]_D = +136.9° (CH₃OH) and an aldehyde of Formula XXXII whose [δ]_D = +63.42° (CH₃OH) |
| 80 | H | H | H | H | 4-F | H | H | H\C=C/H βS      H | αS | oil | An about 1:1 mixture of the two diastereoisomeric trans lactones containing 10-15% of the diastereo isomeric cis lactones C-4 = 3.856 (~0.5H multiplet) one trans lactone C-4 = 4.26 (~0.5H multiplet) other trans lactones C-6 = 4.96 (1H multiplet) both trans lactones Example 80 is synthesized from an oxazolidinone of Formula XLIX whose [α]_D = +6.42° (CHCl₃), m.p. 128°-130° C., an alcohol of Formula XXIII whose [α]_D = +54.3° (CH₃OH), an aldehyde of Formula XXIV whose [α]_D = +55° (CH₃OH) and an aldehyde of Formula XXXII whose [α]_D = +31.2° (CH₃OH) |
| 81 | αR—CH₃ | H | H | αS—CH₃ | naphth-2-yl | H | H | H\C=C/H βS      H | αS | Solid foam | An about 1:1 mixture of two diastereo-isomeric trans lactones containing 10-15% of the two diastereoisomeric cis lactones [α]_D = +93.41° (CH₃OH, c = 0.00425) C-4 = 3.86 (~0.5H multiplet) one trans lactone C-4 = 4.06 (δ0.5H multiplet) other trans lactones C-6 = 4.96 (1H multiplet) both trans lactones Example 81 is synthesized from an alcohol of Formula XXIII whose [α]_D = +104.2° (CH₃OH), m.p. 73°-76° C. an aldehyde of Formula XXIV whose [α]_D = +76.97° (CH₃OH) and an aldehyde of Formula XXXIL m.p. 116°-119° C. |

-continued

| Example | $R_1$ | $R_2$ | $R_3$ | $R_4$ | $R_5$ | $R_6$, $R_{6a}$ | $R_7$ | X | $R_5$-Bearing Phenyl Group | m.p. | |
|---|---|---|---|---|---|---|---|---|---|---|---|
| 82 | βS—$CH_3$ | H | H | βR—$CH_3$ | naphth-1-yl | | H | H\C=C/ αR \H (with CH_3) | βR | solid foam | An about 1:1 mixture of the two diastereoisomeric trans lactones containing 10–15% of the two diastereoisomeric cis lactones $[\alpha]_D = -25.82°$ ($CH_3OH$, c = 0.009). Example 82 is synthesized from Compound XCVII, an alcohol of Formula XXXI whose $[\alpha]_D = -54°$ ($CH_3OH$) and an aldehyde of Formula XXII whose $[\alpha]_D = +54.62°$ ($CH_3OH$) |
| 82A | βS—$CH_3$ | H | H | βR—$CH_3$ | naphth-1-yl | | H | H\C=C/ αR \H (with CH_3) | βR | glassy solid | The 4R,6S trans lactones containing 10–15% of cis lactone $[\alpha]_D = -10.14°$ ($CH_3OH$, c = 0.0069) C-4³ = 3.98(1H multiplet) C-6 = 4.98(1H multiplet) |
| 82B | βS—$CH_3$ | H | H | βR—$CH_3$ | naphth-1-yl | | H | H\C=C/ αR \H (with CH_3) | βR | glassy solid | The 4S,6R trans lactone $[\alpha]_D = -67.01°$ ($CH_3OH$, c = 0.0087) C-4 = 4.0 (1H multiplet) C-6 = 4.9 (1H multiplet) The lactones of Examples 82A and 82B are obtained from the mixture of Example 82 by means of high pressure liquid chromatography utilizing a Waters Prep-500 apparatus having a silica gel column and methyl t-butyl ether as the eluant. |

EXAMPLES 83-91

The following compounds of Group IBa may be synthesized by the processes set forth above:

The following compounds of Group IBa may be synthesized by the processes set forth above:

| Example | $R_1$ | $R_2$ | $R_3$ | $R_4$ | $R_5$ | $R_6$, $R_{6a}$ | $R_7$ | $R_8$ | X | $R_5$—Bearing Phenyl Group | m.p. | |
|---|---|---|---|---|---|---|---|---|---|---|---|---|
| 83 | βS—CH$_3$ | H | H | βR—CH$_3$ | 4-F | H | H | Na$^⊕$ | αR-CH$_2$CH$_2$— | βR | — | A mixture of isomers synthesized from the mixture of lactones of Example 92 via Reaction JJ |
| 84 | H | H | H | H | 4-Cl | H | H | Na$^⊕$ | αS—CH$_2$CH$_2$— | βR | — | A mixture of isomers synthesized from the mixture of lactones of Example 93 via Reaction JJ |
| 85 | αR—CH$_3$ | H | H | αS—CH$_3$ | 4-F | H | H | Na$^⊕$ | βS—CH$_2$CH$_2$— | αS | — | A mixture of isomers synthesized from the mixture of lactones of Example 4 via Reaction JJ |
| 86 | αS—i-C$_3$H$_7$ | H | H | βR—CH$_3$ | 4-F | H | H | C$_2$H$_5$ | 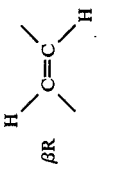 | αS | — | An about 1:1 mixture of the two erythro (3R,5S and 3S,5R) isomers |
| 86A | αS—i-C$_3$H$_7$ | H | H | βR—CH$_3$ | 4-F | H | H | C$_2$H$_5$ | 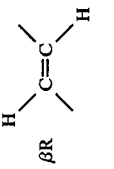 | αS | — | The 3R,5S erythro isomer |
| 87 | αS—i-C$_3$H$_7$ | H | H | βR—CH$_3$ | 4-F | H | H | Na$^⊕$ | 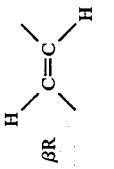 | αS | — | An about 1:1 mixture of the two erythro (3R,5S and 3S,5R) isomers |
| 87A | αS—i-C$_3$H$_7$ | H | H | βR—CH$_3$ | 4-F | H | H | Na$^⊕$ | 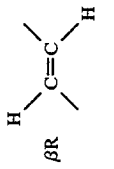 | αS | — | The 3R,5S erythro isomer |
| 88 | αS—i-C$_3$H$_7$ | H | H | βR—CH$_3$ | 4-F | H | H | H | 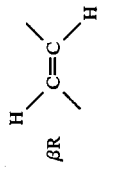 | αS | — | An about 1:1 mixture of the two erythro (3R,5S and 3S,5R) enantiomers |
| 89 | αS—i-C$_3$H$_7$ | H | H | βS—i-C$_3$H$_7$ | 4-F | H | H | C$_2$H$_5$ | 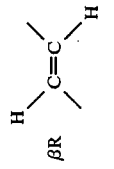 | αS | — | An about 1:1 mixture of the two erythro (3R,5S and 3S,5R) isomers |
| 89A | αS—i-C$_3$H$_7$ | H | H | βS—i-C$_3$H$_7$ | 4-F | H | H | C$_2$H$_5$ | 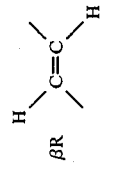 | αS | — | The 3R,5S erythro isomer |

-continued
| Example | $R_1$ | $R_2$ | $R_3$ | $R_4$ | $R_5$ | $R_6$, $R_{6a}$ | $R_7$ | $R_8$ | X | $R_5$—Bearing Phenyl Group | m.p. | |
|---|---|---|---|---|---|---|---|---|---|---|---|---|
| 90 | αS—i-C$_3$H$_7$ | H | H | βS—i-C$_3$H$_7$ | 4-F | H | H | Na$^\oplus$ |  | αS | — | An about 1:1 mixture of the two erythro (3R,5S and 3S,5R) isomers |
| 90A | αS—i-C$_3$H$_7$ | H | H | βS—i-C$_3$H$_7$ | 4-F | H | H | Na$^\oplus$ |  | αS | — | The 3R,5S erythro isomer |
| 91 | αS—i-C$_3$H$_7$ | H | H | βS—i-C$_3$H$_7$ | 4-F | H | H | H |  | αS | — | An about 1:1 mixture of the two erythro (3R,5S and 3S,5R) isomers |

EXAMPLES 92-95A

The following compounds of Group IBb may be synthesized by the processes set forth above:

The following compounds of Group IBb may be synthesized by the processes set forth above:

| Example | $R_1$ | $R_2$ | $R_3$ | $R_4$ | $R_5$ | $R_6, R_{6a}$ | $R_7$ | X | $R_5$—Bearing Phenyl Group | m.p. | |
|---|---|---|---|---|---|---|---|---|---|---|---|
| 92 | βS—CH$_3$ | H | H | βR—CH$_3$ | 4-F | H | H | αR—CH$_2$CH$_2$— | βR | oil | A mixture of Four diastereoisomers wherein the ratio of the two trans lactones to the two cis lactones is about 8-9:1 with the ratio of one trans lactone to the other being about 1:1 and the ratio of one cis lactone to the other also being about 1:1. Example 92 is synthesized from the mixture of Example 74 via Reaction II. |
| 93 | H | H | H | H | 4-Cl | H | H | αS—CH$_2$CH$_2$— | βR | oil | An about 1:1 mixture of two diastereoisomeric trans lactones C—? = 3.9δ (1H multiplet) C—? = 4.3δ (~0.5H multiplet) C—? = 4.45δ (~0.5H multiplet) Example 93 is synthesized from the mixture of Example 73 via Reaction II. |
| 94 | αS—i-C$_3$H$_7$ | H | H | βR—CH$_3$ | 4-F | H | H | H\C=C/CH<br>βR/ \H | αS | — | An about 1:1 mixture of the two trans (4R,6S and 4S,6R) lactones |
| 94A | αS—i-C$_3$H$_7$ | H | H | βR—CH$_3$ | 4-F | H | H | H\C=C/H<br>βR/ \H | αS | — | The 4R,6S trans lactone |
| 95 | αS—i-C$_3$H$_7$ | H | H | βS—i-C$_3$H$_7$ | 4-F | H | H | H\C=C/H<br>βR/ \H | αS | — | An about 1:1 mixture of the two trans (4R,6S and 4S,6R) lactones |
| 95A | αS—i-C$_3$H$_7$ | H | H | βS—i-C$_3$H$_7$ | 4-F | H | H | H\C=C/H<br>βR/ \H | αS | — | The 4R,6S trans lactone |

Insofar as the X-containing side chain is concerned, the components of the mixtures of isomers of Examples 10–40, 43–63 and 83–85 are the 3R,5R (except Examples 53, 86, 87, 88, 89, 90 and 91), 3R,5S, 3S,5R and 3S,5S (except the same six examples) isomers. The mixture of each example may be separated by conventional means, e.g., high pressure (performance) liquid chromatography, to obtain the individual isomers. The preferred isomers are the 3R,5R and 3R,5S isomers, with the former being the particularly preferred isomers of Examples 83–85 and the latter being the particularly preferred isomers of each of the others.

Insofar as the X-containing side chain is concerned, the trans lactone components of the mixtures of isomers of Examples 65–74, 75–82A, 92–94 and 95 that contain two trans lcatones are the 4R,6S and 4S,6R isomers and the cis lactone components of the mixtures of these examples that contain two cis lactones are the 4R,6R and 4S,6S isomers. The 4R,6R and 4R,6S isomers are preferred, with the former being the preferred cis lactone and the latter being the preferred trans lactone.

Insofar as the X-containing side chain is concerned, the trans lactone components of the mixtures of isomers of Examples 92 and 93 are the 4R,6R and 4S,6S isomers and the cis lactone components of the mixture of isomers of Example 92 are the 4R,6S and 4S,6R isomers. The 4R,6R and 4R,6S isomers are preferred, with the former being the preferred trans lactone and the latter being the preferred cis lactone.

The mixtures of isomers of Examples 65–74, 75–82A, 92–94 and 95 may be separated by conventional means, e.g., high pressure (performance) liquid chromatography, to obtain the individual isomers.

Each of the compounds of Examples 1–95A (including each of the possible optical isomers) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

In all the preceding examples, α and β denote relative stereochemistry, not absolute stereochemistry, whereas R and S denote absolute stereochemistry.

Thoughout the examples, the term "reduced pressure" denotes aspirator pressure, and where no solvent is specified in connection with a solution, the solvent is water. All solvent mixtures are by volume.

In all of the preceding examples, except where indicated to the contrary, all infrared spectra were taken in chloroform and all optical rotations were measured at ambient temperature and the concentrations are given in g.ml.

All nuclear magnetic resonance spectra were taken in deuterochloroform at ambient temperature on a 200 MHz spectrometer. All chemical shifts are given in p.p.m. (δ) relative to tetramethylsilane and where a single δ value is given for anything other than a sharp singlet, it is its center point. In the preceding tables, C-4 and C-6 are the nuclear magnetic resonance spectra peaks attributed to the protons attached to the carbon atoms in the 4- and 6-positions, respectively, of the lactone ring and the use of C-? means that it was not possible to determine to which of these two protons the peak in question belongs. In the N.M.R. data in the examples:

d = doublet
dd = doublet of doublet
m = multiplet
om's = overlapping multiplets

What is claimed is:

1. A compound of the formula

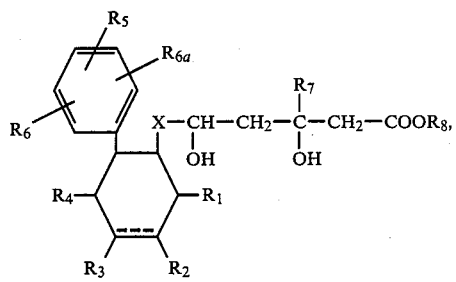

wherein
$R_1$ is hydrogen, $C_{1-3}$alkyl, n-butyl, i-butyl or t-butyl,
$R_2$ is hydrogen or $C_{1-3}$alkyl,
$R_3$ is hydrogen or $C_{1-3}$alkyl,
$R_4$ is hydrogen, $C_{1-3}$alkyl, n-butyl, i-butyl or t-butyl,
$R_5$ is hydrogen, $C_{1-3}$alkyl, n-butyl, i-butyl, t-butyl, $C_{1-3}$alkoxy, n-butoxy, i-butoxy, fluoro, chloro, trifluoromethyl, phenoxy or benzyloxy,
$R_6$ is hydrogen, $C_{1-3}$alkyl, $C_{1-3}$alko; fluoro, chloro, trifluoromethy, phenoxy or benzyloxy, with the provisos that not more than one of $R_5$ and $R_6$ is trifluoromethyl, not more than one of $R_5$ and $R_6$ is phenoxy, and not more than one of $R_5$ and $R_6$ is benzyloxy, or
$R_5$ and $R_6$ are attached to adjacent carbon atoms and taken together form a radical of the formula —CH=CH—CH=CH—,
$R_{6a}$ is hydrogen, $C_{1-2}$alkyl, fluoro or chloro,
$R_7$ is hydrogen or $C_{1-3}$alkyl,
$R_8$ is hydrogen, $R_9$ or M, wherein $R_9$ is a physiologically acceptable ester group, and
M is a cation,
X is —CH$_2$CH$_2$— or

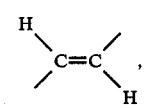

and the broken line represents a double (π) bond or two hydrogen atoms (one on each carbon atom).

2. A compound according to claim 1 wherein M is a pharmaceutically acceptable cation.

3. A compound according to claim 2 having the formula

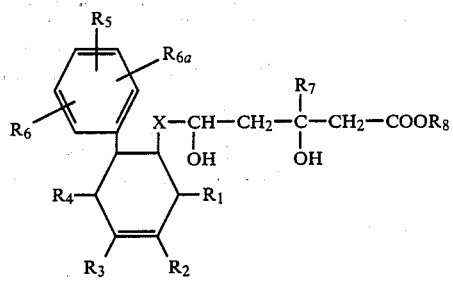

4. A compound according to claim 3 wherein

R₁ is hydrogen or C₁₋₃alkyl,

R₂ is hydrogen,

R₃ is hydrogen,

R₄ is hydrogen or C₁₋₃alkyl,

R₅ is hydrogen, methyl, fluoro or chloro,

R₆ is hydrogen, methyl, fluoro or chloro, or

R₅ and R₆ are attached to adjacent carbon atoms and taken together form a radical of the formula —CH=CH—CH=CH—, R₆ₐ is hydrogen, R₇ is hydrogen, R₈ is hydrogen, C₁₋₂alkyl or M, wherein M is a pharmaceutically acceptable cation, and X is

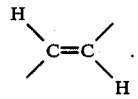

5. A compound according to claim 4 wherein R₁ (when C₁₋₃alkyl) and the R₅-bearing phenyl or naphthyl group in the 6-position of the cyclohexene ring are cis to each other and trans to the

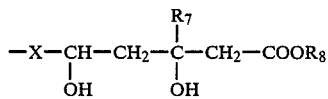

group.

6. A compound according to claim 5 wherein the

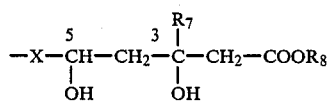

group is in the 3R,5S configuration.

7. A compound according to claim 5 having the formula

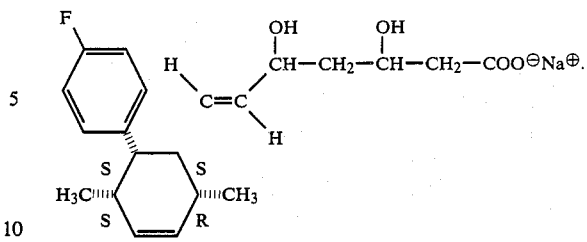

8. The compound according to claim 7 having the formula

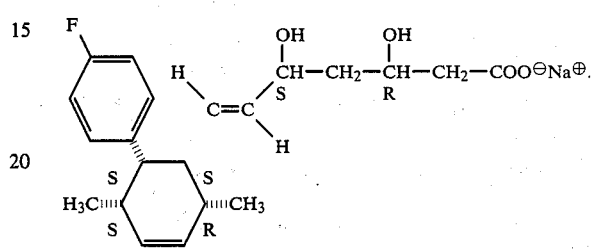

9. A compound according to claim 2 having the formula

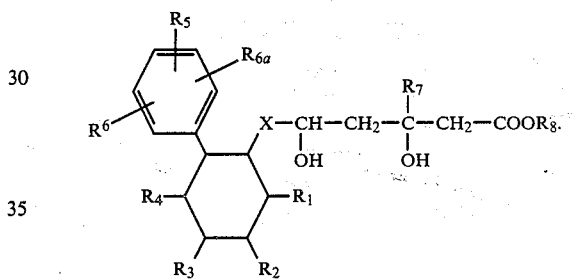

10. A pharmaceutical composition comprising an effective amount of a compound according to claim 2 and a pharmaceutically acceptable carrier, said effective amount being an amount effective for inhibiting cholesterol biosynthesis in a mammal.

11. A method of inhibiting cholesterol biosynthesis comprising administering to a mammal in need of such treatment an effective amount of a compound according to claim 2, said effective amount being an amount effective for inhibiting cholesterol biosynthesis.

12. A method of treating atherosclerosis comprising administering to a mammal in need of such treatment an effective amount of a compound according to claim 2, said effective amount being an amount effective for the treatment of atherosclerosis.

13. A method of treating atherosclerosis according to claim 12 comprising administering to a mammal in need of such treatment an effective amount of a compound of the formula

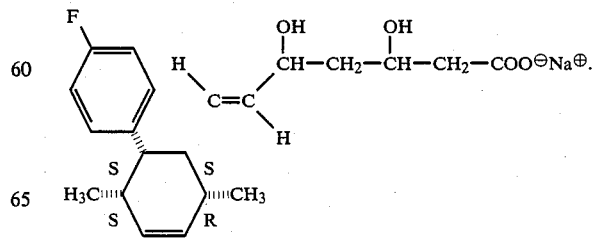

* * * * *